US011365203B2

(12) United States Patent
Zhu et al.

(10) Patent No.: US 11,365,203 B2
(45) Date of Patent: Jun. 21, 2022

(54) FLUORESCENT DYE AND PREPARATION METHOD AND USE THEREOF

(71) Applicant: Fluorescence Diagnosis (shanghai) Biotech Company Ltd., Shanghai (CN)

(72) Inventors: Linyong Zhu, Shanghai (CN); Yi Yang, Shanghai (CN); Dasheng Zhang, Shanghai (CN); Zengmin Du, Shanghai (CN); Bingkun Bao, Shanghai (CN); Qiuning Lin, Shanghai (CN); Yan Li, Shanghai (CN); Xianjun Chen, Shanghai (CN); Lipeng Yang, Shanghai (CN); Chunyan Bao, Shanghai (CN)

(73) Assignee: FLUORESCENCE DIAGNOSIS (SHANGHAI) BIOTECH COMPANY LTD., Shanghai (CN)

( * ) Notice: Subject to any disclaimer, the term of this patent is extended or adjusted under 35 U.S.C. 154(b) by 1 day.

(21) Appl. No.: 16/318,762

(22) PCT Filed: Jul. 18, 2017

(86) PCT No.: PCT/CN2017/093270
§ 371 (c)(1),
(2) Date: Jan. 18, 2019

(87) PCT Pub. No.: WO2018/014820
PCT Pub. Date: Jan. 25, 2018

(65) Prior Publication Data
US 2019/0241584 A1 Aug. 8, 2019

(30) Foreign Application Priority Data
Jul. 20, 2016 (CN) .......................... 201610573970.X

(51) Int. Cl.
| C07D 495/04 | (2006.01) |
| C07D 333/78 | (2006.01) |
| A61K 49/00 | (2006.01) |
| C07D 333/60 | (2006.01) |
| C09K 11/06 | (2006.01) |
| C07D 495/14 | (2006.01) |
| C09B 23/01 | (2006.01) |
| C09B 23/04 | (2006.01) |
| C09B 57/00 | (2006.01) |
| C12Q 1/68 | (2018.01) |
| G01N 33/533 | (2006.01) |
| G01N 33/68 | (2006.01) |

(52) U.S. Cl.
CPC ............ *C07D 495/04* (2013.01); *A61K 49/00* (2013.01); *C07D 333/60* (2013.01); *C07D 333/78* (2013.01); *C07D 495/14* (2013.01); *C09B 23/0058* (2013.01); *C09B 23/0091* (2013.01); *C09B 23/04* (2013.01); *C09B 57/00* (2013.01); *C09K 11/06* (2013.01); *C12Q 1/68* (2013.01); *G01N 33/533* (2013.01); *G01N 33/68* (2013.01)

(58) Field of Classification Search
CPC .................................................... C07D 495/04
See application file for complete search history.

(56) References Cited

U.S. PATENT DOCUMENTS

2010/0029952 A1 2/2010 Tweg et al.

FOREIGN PATENT DOCUMENTS

| CN | 102146215 A | 8/2011 | |
| CN | 102757659 A | 10/2012 | |
| CN | 104610774 A | 5/2015 | |
| CN | 105062465 A | 11/2015 | |
| EP | 0251114 A2 | 1/1988 | |
| ES | 2307462 A1 | 11/2008 | |
| JP | 2013-194039 A | 9/2013 | |
| WO | 2004/020412 A1 | 3/2004 | |
| WO | 2009/152165 A2 | 12/2009 | |
| WO | 2012/102544 A2 | 8/2012 | |
| WO | 2013/142841 A1 | 9/2013 | |
| WO | 2014/103831 A1 | 7/2014 | |
| WO | WO-2018014821 A1 * | 1/2018 | ............ C07F 7/0816 |

OTHER PUBLICATIONS

Doerr, M., et al. "High Tg NLO-polymers by functionalization of reactive precursors." Proceedings of SPIE—The International Society for Optical Engineering. (1995), vol. 2527, pp. 105-115. (Year: 1995).*
Li, Wei, et al. "What Makes Hydroxamate a Promising Anchoring Group in Dye-Sensitized Solar Cells? Insights from Theoretical Investigation." Journal of Physical Chemistry Letters. (2014), vol. 5, pp. 3992-3999. (Year: 2014).*
Arun, K.T. et al., "Near-Infrared Fluorescent Probes: Synthesis and Spectroscopic Investigations of A Few Amphiphilic Squaraine Dyes", J. Phys. Chem. A., 2005, vol. 109, No. 25, pp. 5571-5578.
Huang, H. et al., "Very Large Silacylic Substituent Effects on Response in Silole-Based Polymer Transistors", Chemistry of Materials, 2011, pp. 2185-2200.
Jeong, H. et al, "Synthesis and Characterization of Poly(Dithieno[3,2-b:2',3'-d]pyrrole) Derivatives Containing Thiophene Moieties and Their Application to Organic Devices", Macromolecular Chemistry and Physics, 2011, pp. 2308-2318.
Rieger, R. et al, "Backbone Curvature in Polythiophenes", Chemistry of Materials, 2010, pp. 5314-5318.
Wang, F. et al, "Synthesis, Characterization, and Reactivity of Lanthanide Amides Incorporating Neutral Pyrrole Ligand. Isolation and Characterization of Active Catalyst for Cyanosilylation of Ketones", Organometalics, 2015, pp. 86-93.

(Continued)

*Primary Examiner* — John S Kenyon
(74) *Attorney, Agent, or Firm* — Xsensus LLP

(57) ABSTRACT

Provided are a fluorescent dye and a preparation process and use thereof. The fluorescent dye is able to emit a long wavelength, is sensitive and specific to viscosity, and is used for a wide range of purposes, such as viscosity testing, fluorescent labeling, quantification or detection of proteins, enzymes or nucleic acids. In addition, it can be used as a fluorescent-activated probe.

22 Claims, 4 Drawing Sheets

(56) References Cited

OTHER PUBLICATIONS

Wang, H. et al, "Modifications of DCDHF single molecule fluorophores to impart water solubility", Tetrahedron Letters, 2007, pp. 3471-3474.
Wu, L. et al, "Syntheses of Highly Fluorescent GFP-Chromophore Analogues", J. Am. Chem. Soc., 2008, pp. 4089-4096.
Yan, P. et al, "Amino(oligo)thiophene-Based Environmentally Sensitive Biomembrane Chromophores", J. Org. Chem., 2008, pp. 6587-6594.
Martín-Santamaría et al., "New scaffolds for the design of selective estrogen receptor modulators," Organic & Biomolecular Chemistry 6 (2008), pp. 3486-3487.
Blenkle et al., "Chalcogens as electron donors for selected nonlinear optic phores," Journal of the Chemical Society, Perkin Transactions 2 (1996), pp. 1377-1378, cited in ISR.
Zayed et al., "One Step Synthesis of 3-Cyano-4-(5-nitrobenzothienyl)pyridines and 3-Cyano-4-(5-nitrobenzothienyl)pyridin-2-ones for Biological Evaluation," Journal of Heterocyclic Chemistry 20 (1983), pp. 129-130.
Pal et al., "Synthesis, characterization and laser flash photolysis studies of some naphthothiophenes bearing electron donor and acceptor functional groups," Journal of Photochemistry and Photobiology A: Chemistry 174 (2005), pp. 138-139, cited in ISR.
Ge et al., "Synthesis of new dithieno [3,2-b: 2', 3'-d] pyrrole (DTP) units for photovoltaic cells," Dyes and Pigments 128 (2016), pp. 8-9.
Choi et al., "Direct Evidence of Forster Resonance Energy Transfer for the Enhanced Photocurrent Generation in Dye-Sensitized Solar Cell," The Journal of Physical Chemistry C 118 (2013), pp. 16319-16320.
Li et al., "What Makes Hydroxamate a Promising Anchoring Group in Dye-Sensitized Solar Cells? Insights from Theoretical Investigation," The Journal of Physical Chemistry Letters 5 (2014), pp. 3992-3993, cited in ISR.
Szent-Gyorgyi et al., "Fluorogen-activating single-chain antibodies for imaging cell surface proteins," Nature Biotechnology 26 (2008), pp. 235-240, cited in the specification.
Paige et al., "RNA Mimics of Green Fluorescent Protein," Science 333 (2011), pp. 642-646, cited in the specification.
Echeverry et al., "New organic dyes with high IPCE values containing two triphenylamine units as co-donors for efficient dye-sensitized solar cells," RSC Advances 5 (2015), pp. 60823-60830, cited in ISR.
Gao et al., "Synthesis and photoelectric properties of an organic dye containing benzo [1,2-b: 4,5-b] dithiophene for dye-sensitized solar cells," Chinese Chemical Letters 24 (2013), pp. 149-152, cited in ISR.
Gao et al., "Fine-tuning the Electronic Structure of Organic Dyes for Dye-Sensitized Solar Cells," Organic Letters 14 (2012), pp. 4330-4333, cited in ISR.
Hao et al. "Organic Dyes Incorporating the Benzo [1, 2-b: 4, 5-b'] dithiophene Moiety for Efficient Dye-Sensitized Solar Cells," Organic Letters 13 (2011), S1-S32, cited in ISR.
Liu et al., "A Rapid SNAP-Tag Fluorogenic Probe Based on an Environment-Sensitive Fluorophore for No-Wash Live Cell Imaging," ACS Chemical Biology 9 (2014), pp. 2359-2365.
Zhou et al., "Molecular Rotors as Fluorescent Viscosity Sensors: Molecular Design, Polarity Sensitivity, Dipole Moments Changes, Screening Solvents, and Deactivation Channel of the Excited States," European Journal of Organic Chemistry 2011 (2011), pp. 4773-4787.
Shao et al., "Thiophene-Inserted Aryl-Dicyanovinyl Compounds: The Second Generation of Fluorescent Molecular Rotors with Significantly Redshifted Emission and Large Stokes Shift," European Journal of Organic Chemistry 2011 (2011), pp. 6100-6109.
International Search Report dated Oct. 18, 2017, issued in counterpart International Application No. PCT/CN2017/093270 (3 pages, including annex).

* cited by examiner

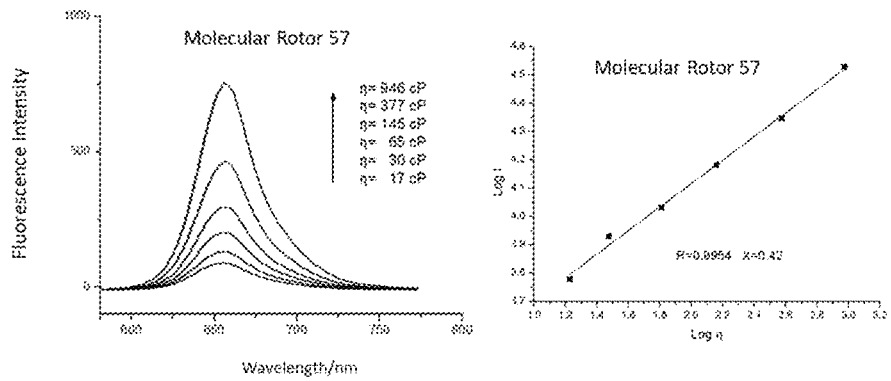
Figure 13
Figure 14
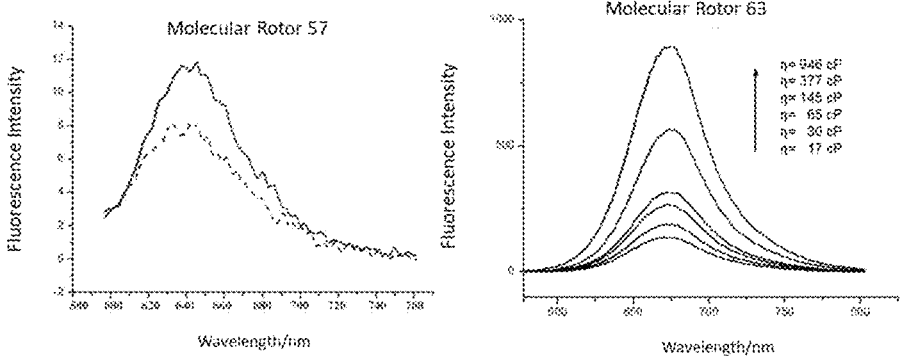
Figure 15
Figure 16
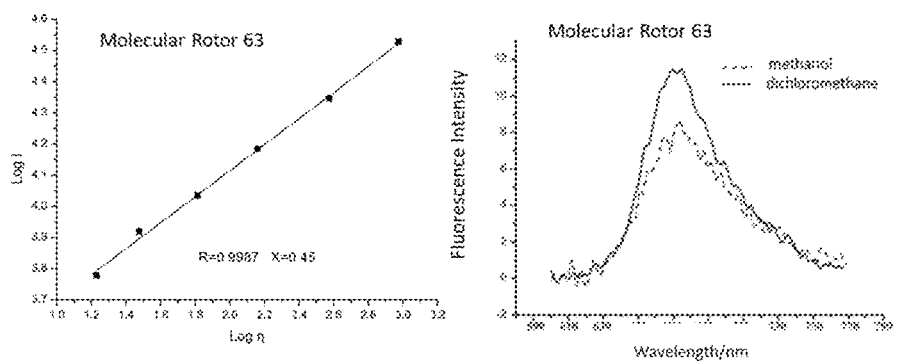
Figure 17
Figure 18

FLUORESCENT DYE AND PREPARATION METHOD AND USE THEREOF

TECHNICAL FIELD

The present invention relates to the technical field of fluorescent dyes, particularly a long-wavelength-emitting viscosity-responsive fluorescent dye and a preparation method and use thereof.

BACKGROUND ART

Recently, a fluorescence method has been developed as an important means to test microscopic viscosity. Compared with other methods, fluorescence detection is unique in its sensitivity, in situ, real-time, visuality and the like. The method effectively utilizes the characteristic that the fluorescence intensity of some dye probes is sensitive to the viscosity of the surrounding medium, and implements effectively monitoring of the viscosity of the medium by observing changes in fluorescence intensity. Currently, such viscosity-responsive fluorescent probes are often named as molecular rotors. They distort the molecules after photoexcitation to form charge transfer states in the TICT molecule, and excited state energy is mainly emitted in the non-radiation form. When the viscosity responsive dye is in a microenvironment with higher viscosity or rigidity, molecular distortion of such viscosity responsive dyes becomes difficult, and molecular conformation is limited; at this time, the excited state energy of the dye is expressed mainly in the form of radiation, in other words, radiation is fluorescence. Therefore, the fluorescence intensity of the molecular rotor directly reflects the viscosity of the surrounding medium.

Importantly, in addition to viscosity detection, molecular rotors are also widely used in the design of fluorogenic probes based on the restriction of molecular conformation to activate fluorescence. For example, a molecular rotor with a thiazole orange structure is a typical nuclear dyeing reagent. After the dye enters the nucleus and binds to DNA, the molecular conformation is limited (equivalent to a sharp increase in viscosity), and the fluorescence is lightened up, but the dye does not have any fluorescence in other parts of the cell, achieving a no-wash, low background nuclear dyeing effect. As another example, bound to the antibody protein, the probe achieves background-free labeling of the cell surface protein (S. G. Christopher et. al. Nat. Biotechnol. 2008, 26, 235-240); bound to the aptamer, the probe lightens up the labeling of the DNA (J. S. Paige et. al. Science. 2011, 333, 642-646); in addition, if bound to amyloid, the probe lightens up the molecular rotor fluorescence to realize the research of Alzheimer's disease; additionally, by binding a ligand or an inhibitor to a protein tag or an enzyme and by introducing a molecular rotor into the lumen of the enzyme, specific fluorescence-activated tags of proteins or recognition, detection and quantification of enzymes can be achieved.

However, viscosity-responsive molecular rotor dyes that are sensitive and responsive to long-wavelength emission such as yellow or red or even near-infrared spectrums are very scarce. Although thiazole orange and analogues thereof have been widely used, these dyes have a dominant cationic structure and are combined easily with negative charged biomacromolecules such as DNA, which may cause false positives in viscosity increase or a high background in imaging applications. In addition, there are few reported long-wavelength viscosity-responsive fluorescent probes, most of which have characteristics of non-specific responses, especially polar responses.

SUMMARY OF THE INVENTION

Provided is a fluorescent dye with a novel structure, having the capability of long wavelength emission.

Therefore, a fluorescent dye is provided, the structure of which is shown in formula (I),

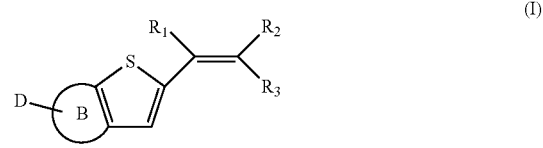

(I)

wherein:

D- is $X_0O-$ or $N(X_1)(X_2)-$; $X_0$, $X_1$, and $X_2$ are each independently selected from the group consisting of hydrogen, an alkyl group and a modified alkyl group; $X_1$ and $X_2$ are optionally linked to each other to form a saturated or unsaturated alicyclic heterocyclic ring;

the ring B is selected from at least one consisting of an aromatic ring and an aromatic heterocyclic ring;

in the structure of the following formula (I-2) formed by condensing the ring B with a thiophene ring, each hydrogen atom contained therein is optionally replaced independently with a substituent selected from the group consisting of a halogen atom, a nitro group, a hydrophilic group, an alkyl group, and a modified alkyl group, the substituents being optionally linked to each other to form a saturated or unsaturated alicyclic or alicyclic heterocyclic ring;

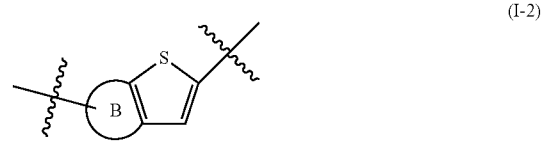

(I-2)

optionally, the structure of the formula (I-2) is interlinked to $X_1$, $X_2$ to form an alicyclic heterocyclic ring;

$R_1$ is selected from the group consisting of hydrogen, a halogen atom, a nitro group, an alkyl group, an aryl group, a heteroaryl group, a hydrophilic group, or a modified alkyl group;

$R_2$ is selected from the group consisting of cyano, carboxyl, a keto group, an ester group, an amide group, a phosphonic acid group, a phosphonate group, a sulfonic group, a sulfonate group, a sulfone group, a sulfoxide group, an aryl group, a heteroaryl group, an alkyl group, or a modified alkyl group;

$R_3$ is a cyano group;

the structural moiety of the following formula (I-3) in the formula (I):

(I-3)

optionally forms a cyclic structure of the following formulae (I-3-a) or (I-3-b):

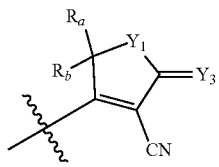
(I-3-a)

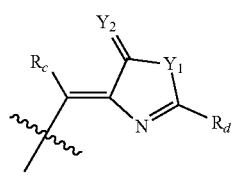
(I-3-b)

wherein, $R_a$ and $R_b$ are selected independently from the group consisting of hydrogen, an alkyl group, and a modified alkyl group, and $R_a$ and $R_b$ are optionally bonded to each other to form an alicyclic or alicyclic heterocyclic ring;

$R_c$ and $R_d$ are selected independently from the group consisting of hydrogen, a halogen atom, nitro, an alkyl group, an aryl group, a hydrophilic group, and a modified alkyl group;

$Y_1$ is selected from the groups consisting of —O—, —S—, —(S=O)—, and —(NR$_i$)—, wherein $R_i$ is selected from the group consisting of hydrogen, an alkyl group, and a modified alkyl group;

$Y_2$ is selected from the group consisting of =O, =S, =S=O, and =NR$_i$, wherein $R_i$ is selected from the group consisting of hydrogen, an alkyl group, and a modified alkyl group;

$Y_3$ is selected from the group consisting of =O, =S, =S=O, and =NR$_i$, wherein $R_i$ is selected from the groups consisting of hydrogen, an alkyl group, and a modified alkyl group, or $Y_3$ is $=C(R_c)(CN)$;

Re is selected from the group consisting of cyano, carboxyl, a keto group, an ester group, an amide group, a phosphonic acid group, a phosphonate group, a sulfonic group, a sulfonate group, a sulfone group, a sulfoxide group, an aryl group, a heteroaryl group, an alkyl group, or a modified alkyl group;

when $R_2$ or $R_e$ is an aryl group or a heteroaryl group, the hydrogen atom on the ring is optionally replaced independently with a substituent selected from the group consisting of a halogen atom, nitro, a hydrophilic group, an alkyl group or a modified alkyl group; optionally, the substituents being linked to each other to form a saturated or unsaturated alicyclic or alicyclic heterocyclic ring;

wherein,
the alkyl group is a saturated aliphatic linear or branched alkyl group having 1 to 10 carbon atoms;
the modified alkyl group is a group obtained by replacing any carbon atom of the alkyl group with at least one group selected from the group consisting of a halogen atom, —O—, —OH, —CO—, —NO$_2$, —CN, —S—, —SO$_2$—, —(S=O)—,

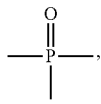

phenylene, a primary amino group, a secondary amino group, a tertiary amino group, a quaternary ammonium group, a saturated or unsaturated monocyclic or bicyclic cyclohydrocarbylene group, a bridged alicyclic heterocyclic ring; the modified alkyl group has 1 to 50 carbon atoms, wherein the carbon-carbon single bond is optionally replaced independently by a carbon-carbon double bond or a carbon-carbon tripe bond;

the alicyclic ring is a four to ten-membered monocyclic or polycyclic alicyclic ring;

the alicyclic heteroalicyclic ring is a four to ten-membered monocyclic or polycyclic alicyclic heteroalicyclic ring with at least one heteroatom selected from the group consisting of N, O, S and Si on the ring; when the alicyclic heteroalicyclic ring contains an S atom, it is optionally —SO— or —SO$_2$—; the alicyclic heterocyclic ring is optionally substituted with a halogen atom, nitro, an alkyl group, an aryl group, a hydrophilic group, and a modified alkyl group;

the aryl group or the aromatic ring is a five to ten-membered monocyclic or condensed bicyclic ring;

the heteroaryl or the aromatic heterocyclic ring is a five to ten-membered monocyclic or condensed bicyclic ring with at least one heteroatom selected from the group consisting of N, O, S and Si on the ring;

the halogen atoms are each independently selected from the group consisting of F, Cl, Br, and I;

the hydrophilic group is hydroxyl, a sulfonic group, a sulphuric acid group, a phosphonic acid group, a primary amino group, a secondary amino group or a tertiary amino group and substituendum thereof;

the monocyclic cyclohydrocarbylene group is a four to seven-membered monocyclic cyclohydrocarbylene group;

the bicyclic cyclohydrocarbylene group is a five to seven-membered bicyclic cyclohydrocarbylene group;

the bridged alicyclic heterocyclic ring is a five to twenty-membered bridged alicyclic heterocyclic ring having at least one heteroatom selected from the group consisting of N, O, and S on the ring.

Optionally, in the above-mentioned fluorescent dye, the modified alkyl group is a group containing at least one group selected from —OH, —O—, ethylene glycol units, monosaccharide units, disaccharide units, polysaccharide units, —O—CO—, —NH—CO—, —SO$_2$—O—, —SO—, —SO$_2$—NH—, —SS—, —CH=CH—,

a halogen atom, cyano, nirtro, a phosphate group and a phosphonate group.

Optionally, in the above-mentioned fluorescent dye, the alicyclic heterocyclic ring is selected from the group consisting of azetidine, pyrrolidine, piperidine, tetrahydrofuran, tetrahydropyran, morpholine, and thiomorpholine ring.

Optionally, in the above-mentioned fluorescent dye, the heteroaryl ring is selected from the group consisting of thiophene, furan, and pyrrole ring.

Optionally, in the above-mentioned fluorescent dye, the $X_1$ and $X_2$ are independently a $C_{1-50}$ linear or branched alkyl group optionally substituted by one or more groups selected from the group consisting of hydroxyl, cyano, a halogen atom, carboxyl, and a quaternary ammonium group; or a $C_{2-50}$ ether chain group having 1 to 10 oxygen atoms and optionally substituted by one or more groups selected from the group consisting of a sulfonic acid group or carboxyl; or N(X₁)(X₂)— forms any group selected from the group consisting of the following formulae (I-1-1) to (I-1-4):

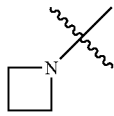
(I-1-1)

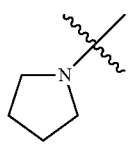
(I-1-2)

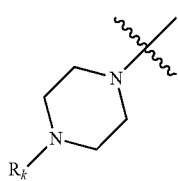
(I-1-3)

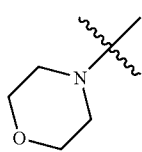
(I-1-4)

wherein $R_k$ is hydrogen or a $C_{1-10}$ alkyl group.

Alternatively, in the foregoing fluorescent dye, the two adjacent substituents in the structure of the formula (I-2) are bonded to each other to form a saturated or unsaturated alicyclic or alicyclic heterocyclic ring;

optionally, H of CH in the ring B is substituted with a halogen atom, nitro, a hydrophilic group, an alkyl group or a modified alkyl group;

optionally, the ring B contains NH; optionally, H of the NH is substituted with an alkyl group or a modified alkyl group;

optionally, the structure of the formula (I-2) is selected from the structures of the following formulae (I-2-1) to (I-2-17):

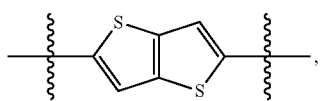
(I-2-1)

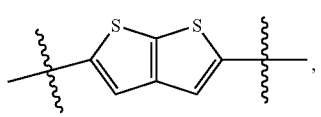
(I-2-2)

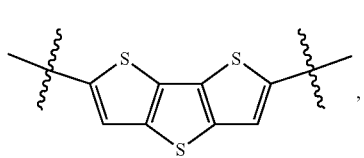
(I-2-3)

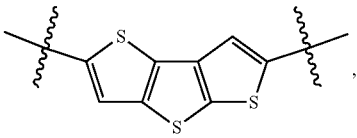
(I-2-4)

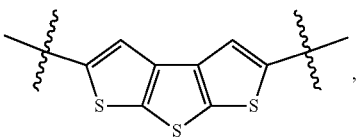
(I-2-5)

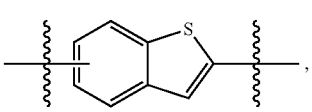
(I-2-6)

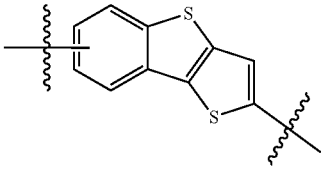
(I-2-7)

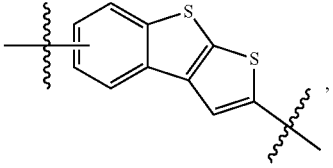
(I-2-8)

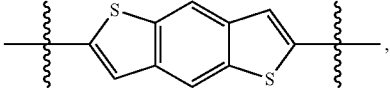
(I-2-9)

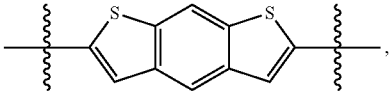
(I-2-10)

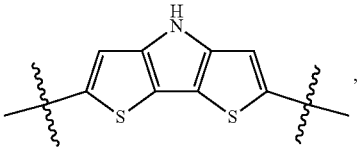
(I-2-11)

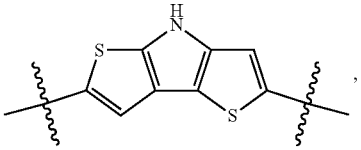
(I-2-12)

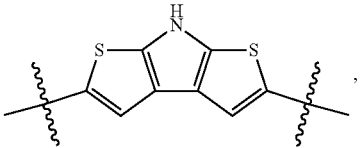
(I-2-13)

optionally, the structure of the formula (I-2) is selected from the group consisting of the structures of the formulae (I-2-1), (I-2-3), (I-2-6), (I-2-7), (I-2-9), (I-2-10), (I-2-11), (I-2-14), (I-2-15), (I-2-16) and (I-2-17).

Alternatively, in the aforesaid fluorescent dye, $R_a$ and $R_b$ of the formula (I-3-a) form the following structure together with the carbon atom bonded:

optionally, the $R_2$ and Re are independently groups selected from the following structures, or bicyclic or polycyclic condensed aromatic rings or condensed aromatic heterocyclic rings formed by the following structures themselves or condensed therebetween, preferably bicyclic or tricyclic condensed aromatic rings or condensed aromatic heterocyclic rings;

optionally, H of the CH in the above structures of $R_2$ or $R_e$ is substituted by a halogen atom, nitro, a hydrophilic group, an alkyl group or a modified alkyl group; optionally, $R_2$ or $R_e$ is an NH-containing group of the above structures; optionally, H of the NH is substituted with an alkyl or a modified alkyl group;

or, $R_2$ and $R_e$ are independently modified alkyl groups comprising: a keto group, an ester group or an amide group, and being linked to the alkenyl carbon of formula (I-3) or (I-3-a) via the carbonyl group in the keto group, the ester group or the amide group;

optionally, the structure of the formula (I-3) is one of the following formulae (I-3-1) to (I-3-18):

(I-3-4)
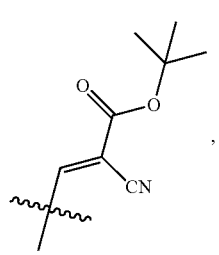
(I-3-5)
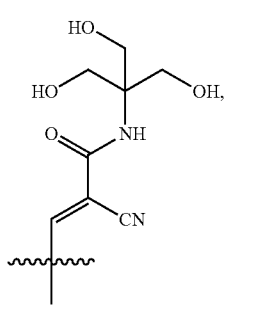
(I-3-6)
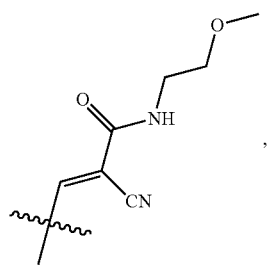
(I-3-7)
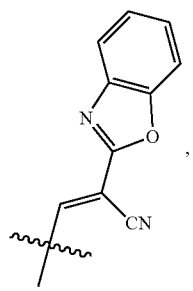
(I-3-8)
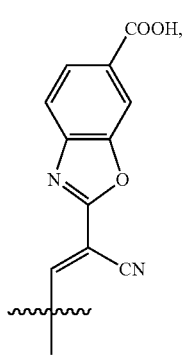
(I-3-9)
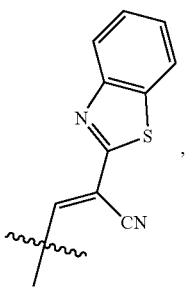
(I-3-10)
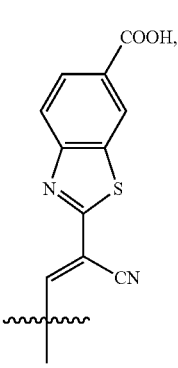
(I-3-11)
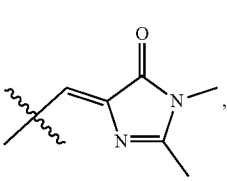
(I-3-12)
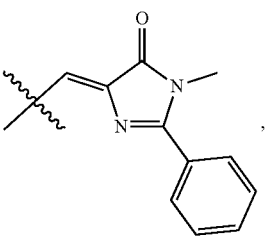
(I-3-13)
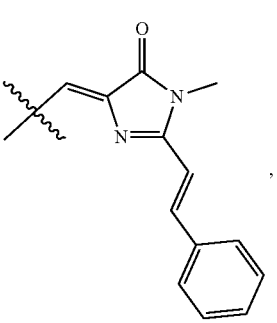
(I-3-14)
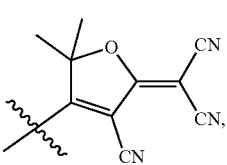

-continued

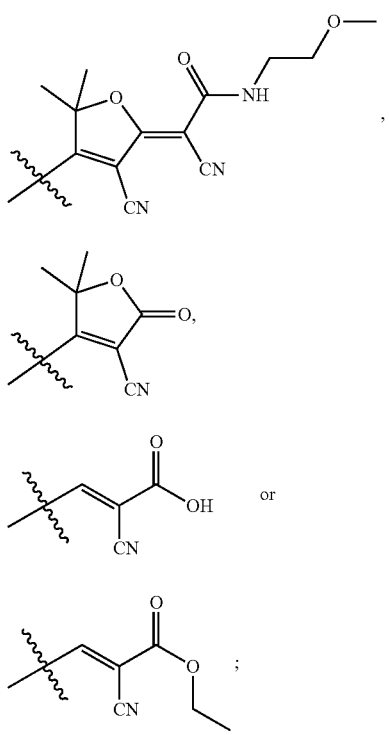

optionally, the structure of the formula (I-3) is one of formulae (I-3-1), (I-3-2), (I-3-4), (I-3-5), (I)-3-7), (I-3-9), (I-3-11), (I-3-12), (I-3-13), (I-3-16), (I-3-17) and (I-3-18).

Alternatively, the above-mentioned fluorescent dye is characterized in that the fluorescent dye is selected from the group consisting of the compounds of the following formulae:

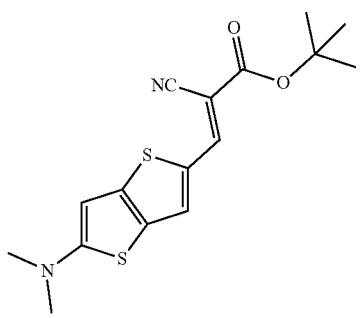

Molecular Rotor 1

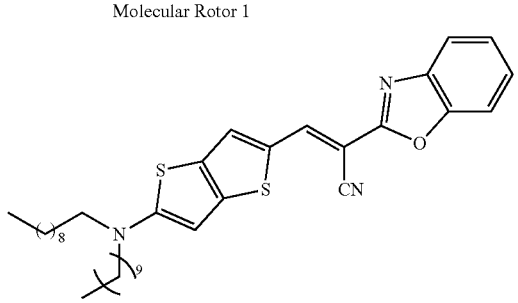

Molecular Rotor 2

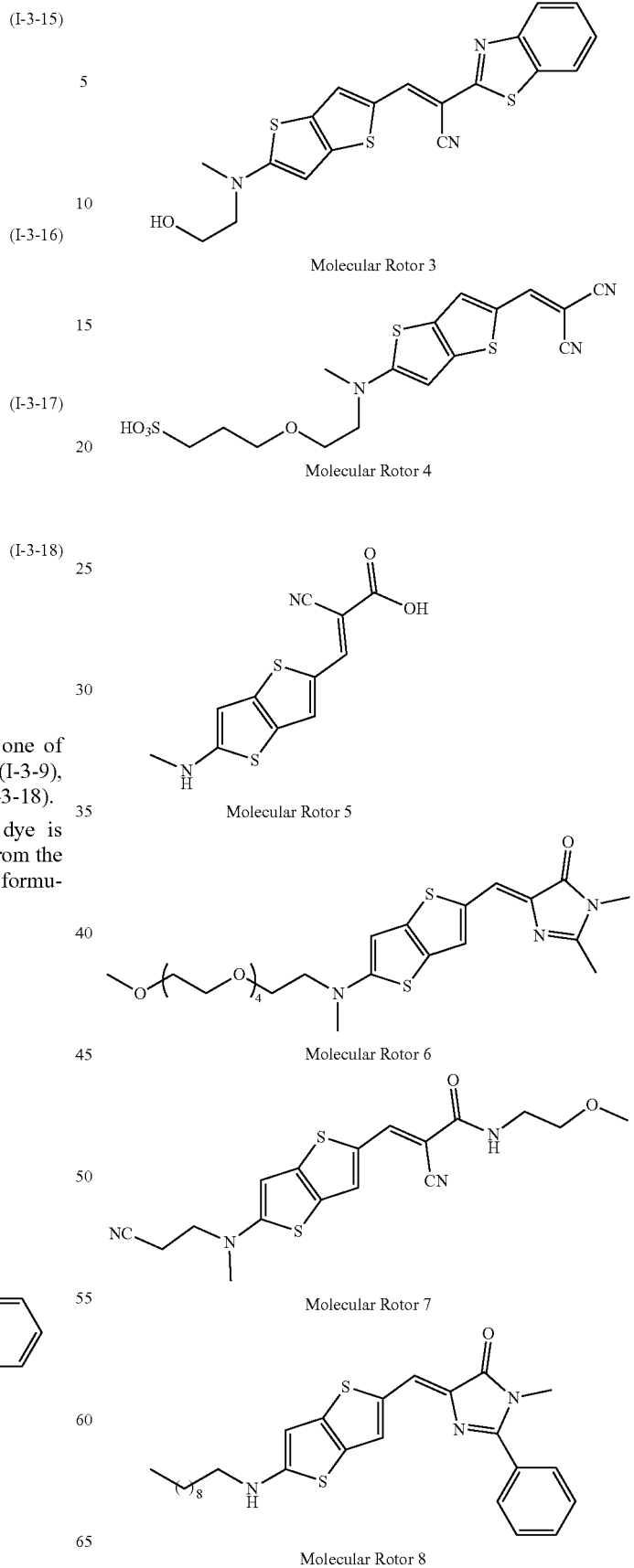

Molecular Rotor 3

Molecular Rotor 4

Molecular Rotor 5

Molecular Rotor 6

Molecular Rotor 7

Molecular Rotor 8

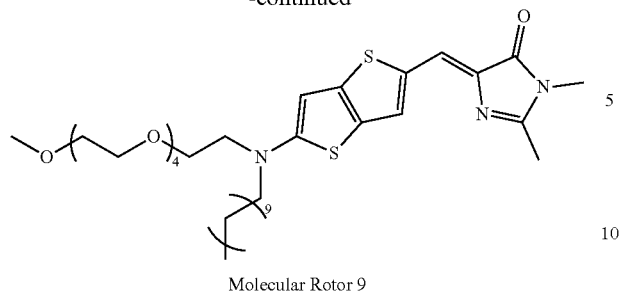
Molecular Rotor 9
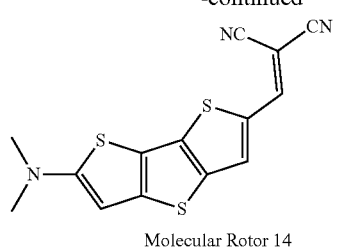
Molecular Rotor 14
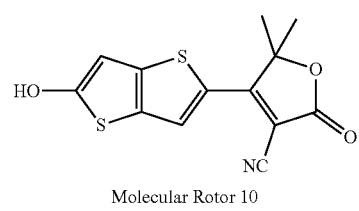
Molecular Rotor 10
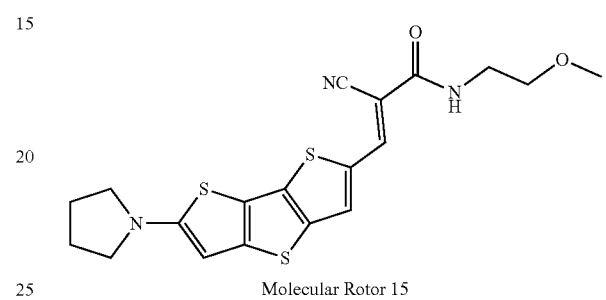
Molecular Rotor 15
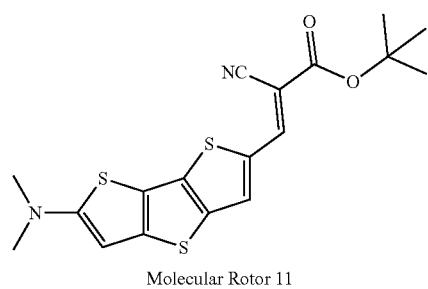
Molecular Rotor 11
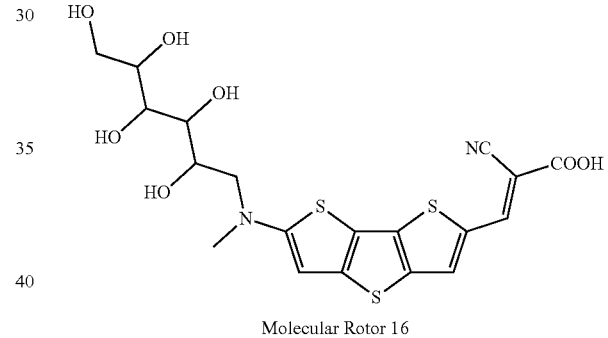
Molecular Rotor 16
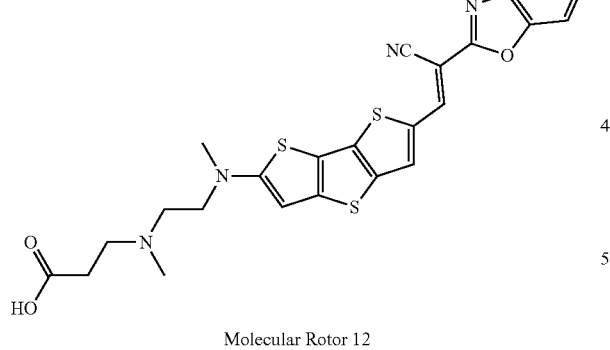
Molecular Rotor 12
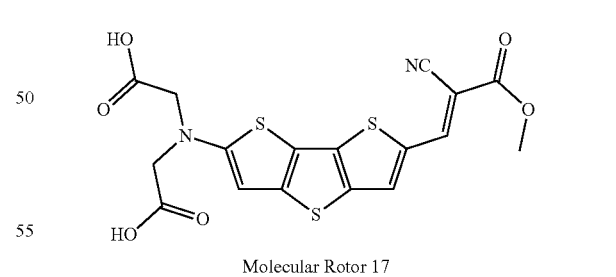
Molecular Rotor 17
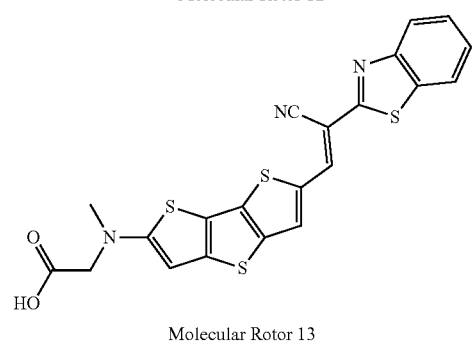
Molecular Rotor 13
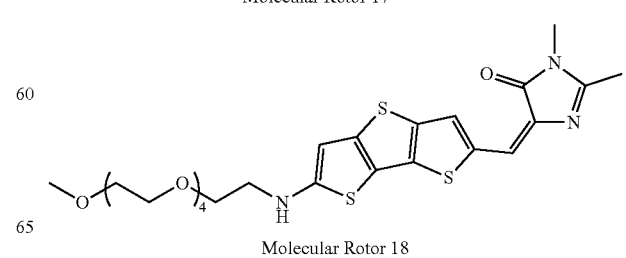
Molecular Rotor 18

-continued
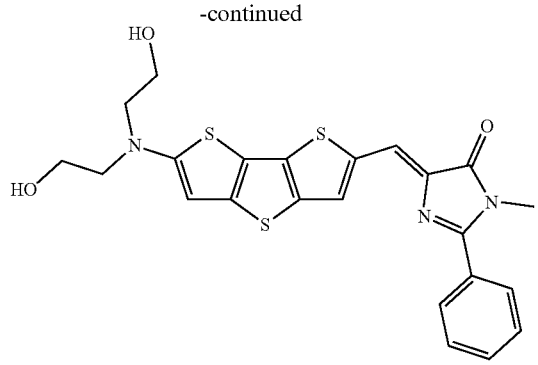
Molecular Rotor 19
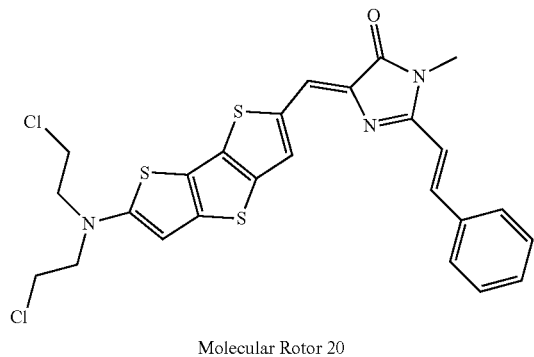
Molecular Rotor 20
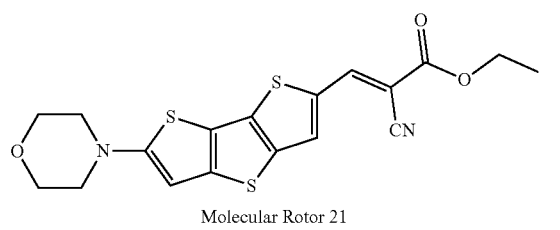
Molecular Rotor 21
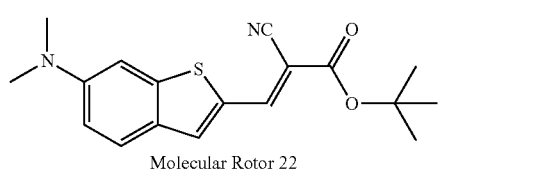
Molecular Rotor 22
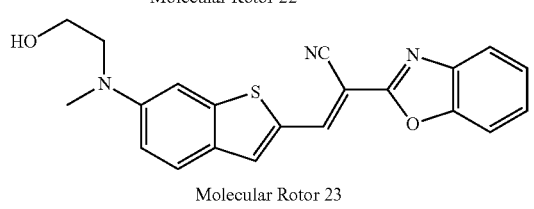
Molecular Rotor 23
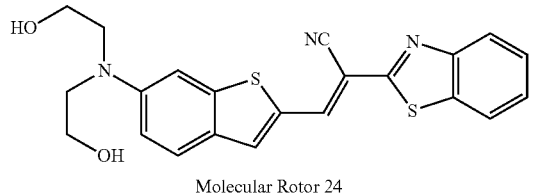
Molecular Rotor 24
-continued
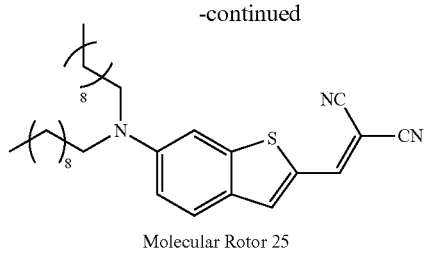
Molecular Rotor 25
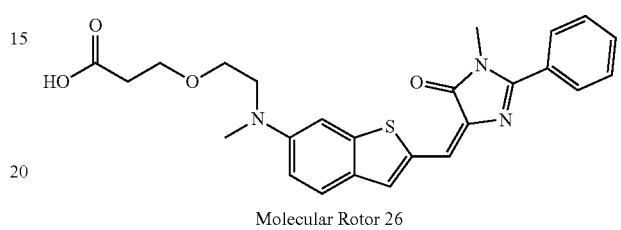
Molecular Rotor 26
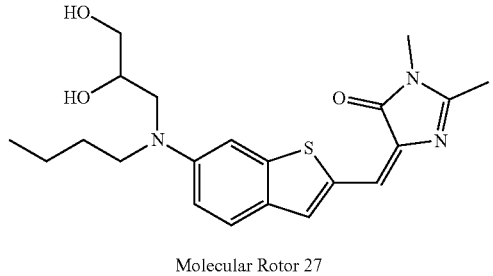
Molecular Rotor 27
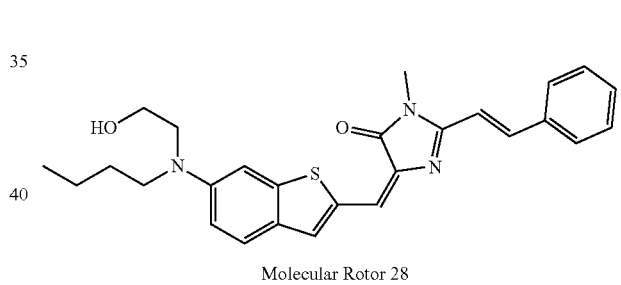
Molecular Rotor 28
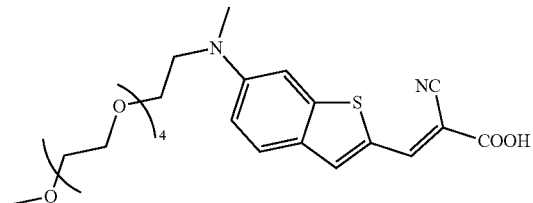
Molecular Rotor 29
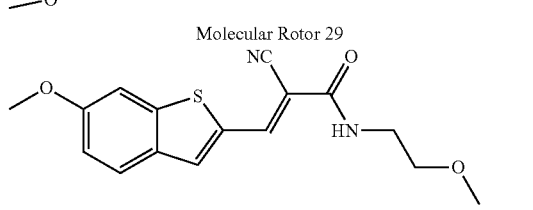
Molecular Rotor 30
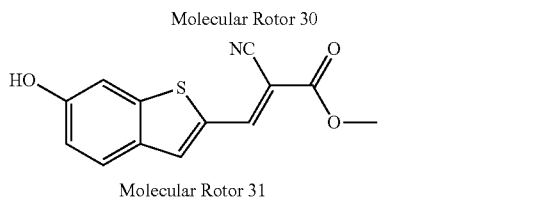
Molecular Rotor 31

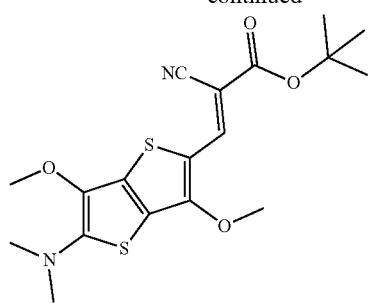
Molecular Rotor 32
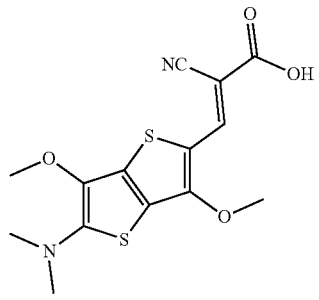
Molecular Rotor 33
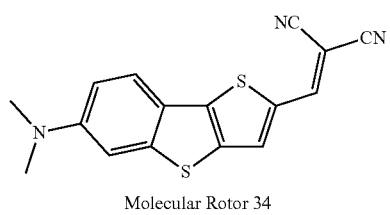
Molecular Rotor 34
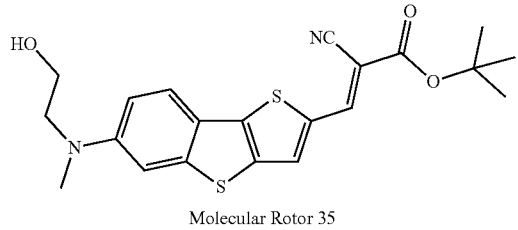
Molecular Rotor 35
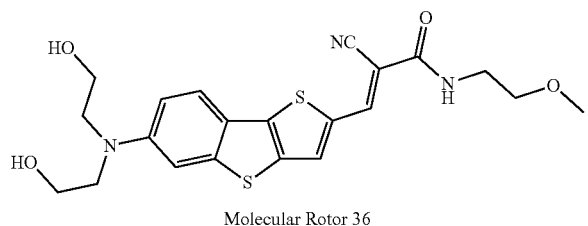
Molecular Rotor 36
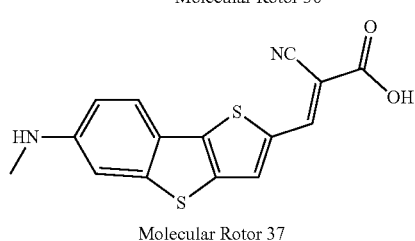
Molecular Rotor 37
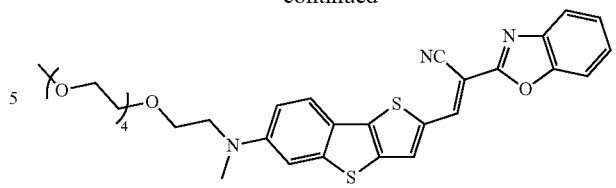
Molecular Rotor 38
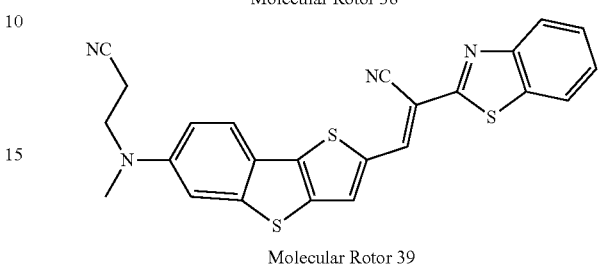
Molecular Rotor 39
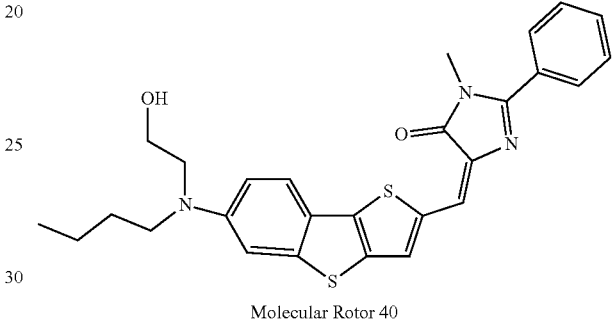
Molecular Rotor 40
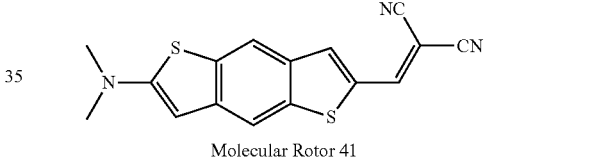
Molecular Rotor 41
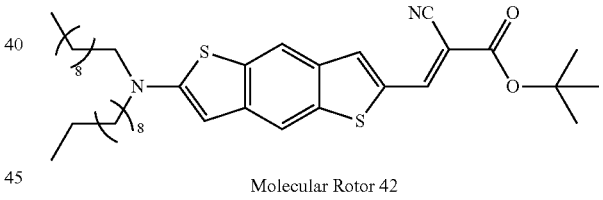
Molecular Rotor 42
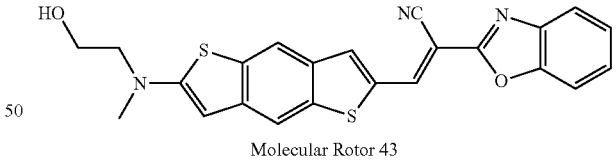
Molecular Rotor 43
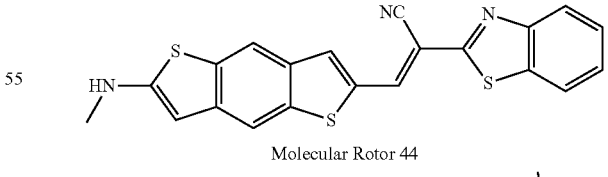
Molecular Rotor 44
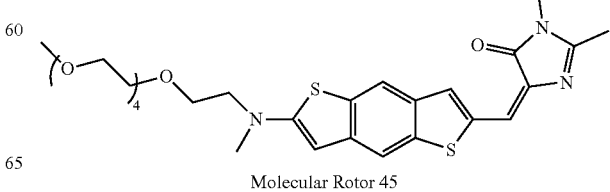
Molecular Rotor 45

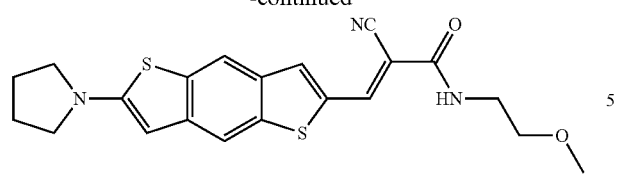
Molecular Rotor 46
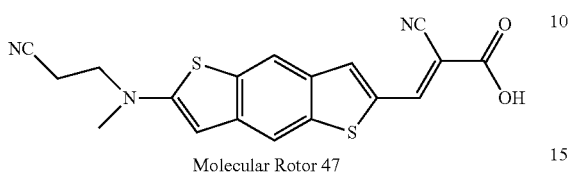
Molecular Rotor 47
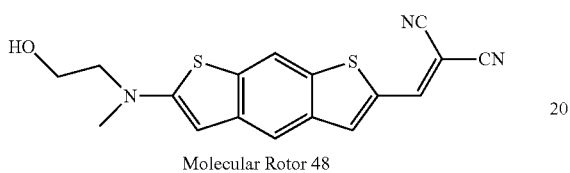
Molecular Rotor 48
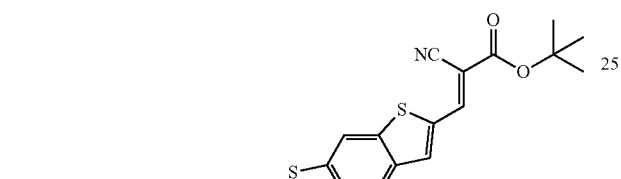
Molecular Rotor 49
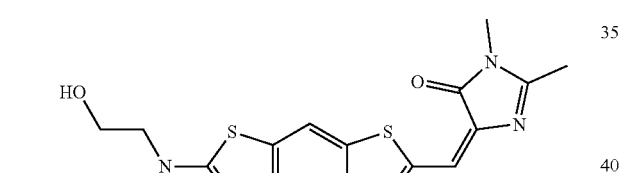
Molecular Rotor 50
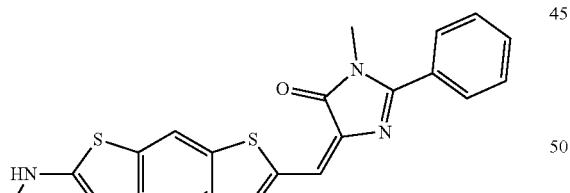
Molecular Rotor 51
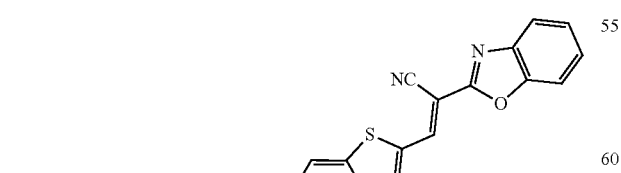
Molecular Rotor 52
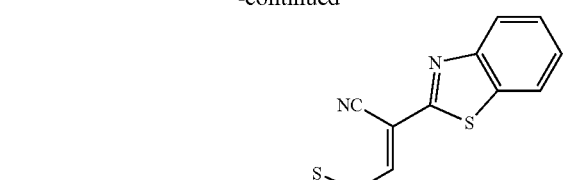
Molecular Rotor 53
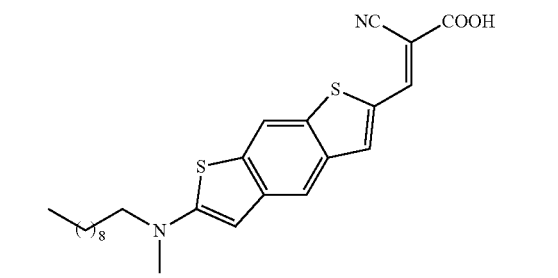
Molecular Rotor 54
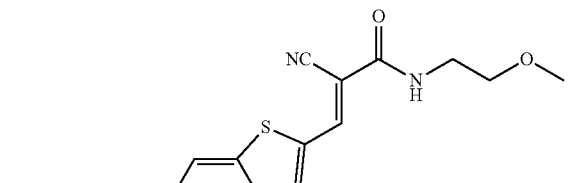
Molecular Rotor 55
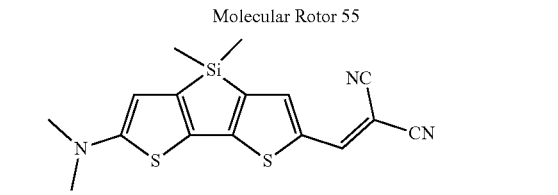
Molecular Rotor 56
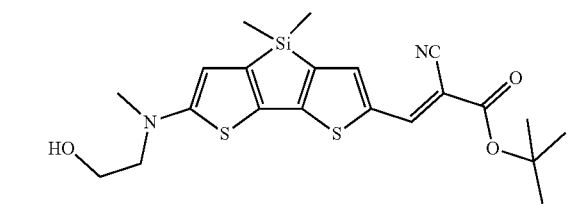
Molecular Rotor 57
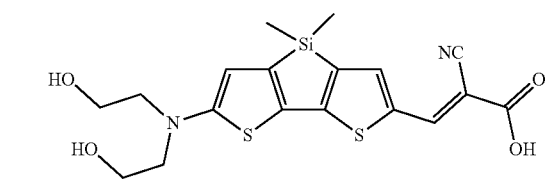
Molecular Rotor 58

-continued

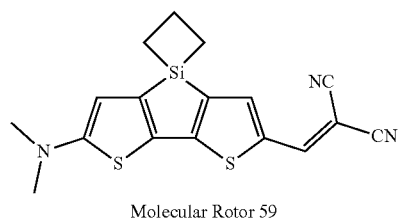

Molecular Rotor 59

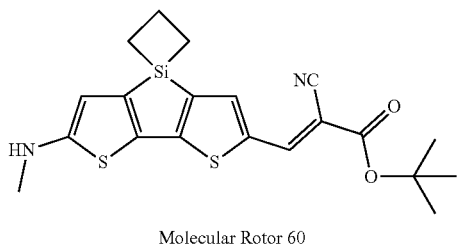

Molecular Rotor 60

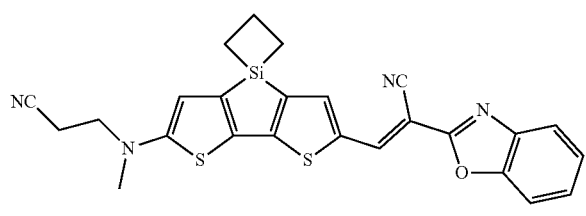

Molecular Rotor 61

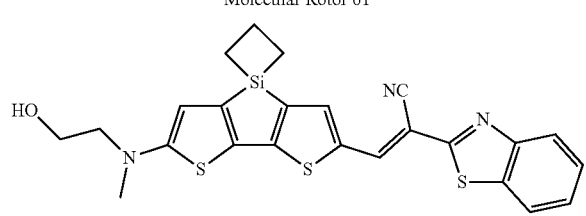

Molecular Rotor 62

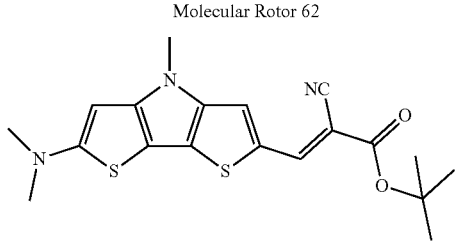

Molecular Rotor 63

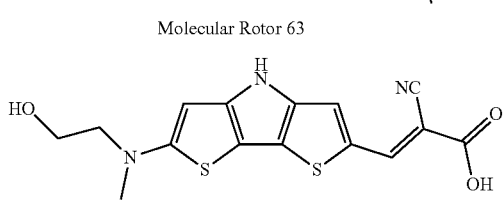

Molecular Rotor 64

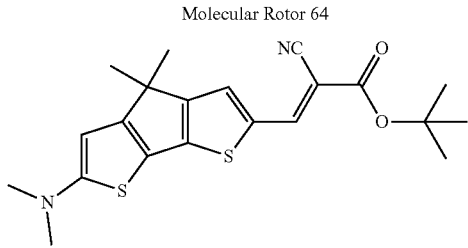

Molecular Rotor 65

-continued

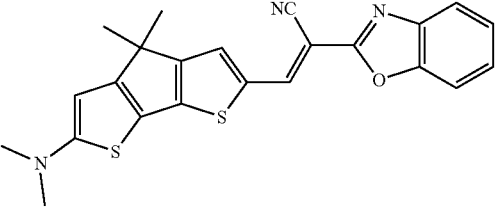

Molecular Rotor 66

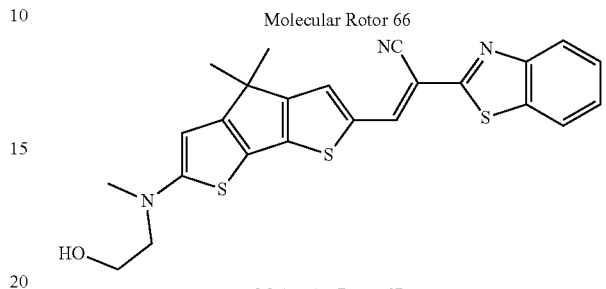

Molecular Rotor 67

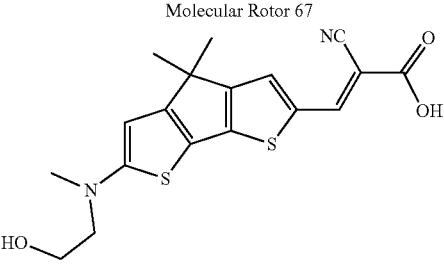

Molecular Rotor 68

In another aspect, further provided is a process for preparing the aforesaid fluorescent dye, comprising the step of conducting an aldol condensation reaction of a compound of the formula (II) with a compound of the formula (III).

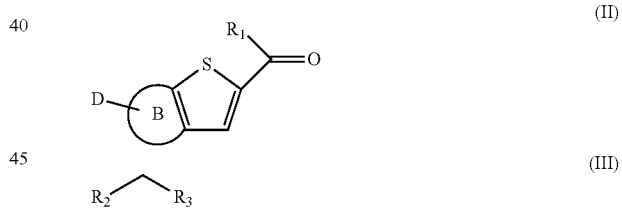

In another aspect, further provided is use of the above fluorescent dye in viscosity testing, fluorescent labeling of a protein, fluorescent labeling of a nucleic acid, quantification or detection of a protein, or quantification or detection of a nucleic acid.

In another aspect, further provided is a fluorogenic probe, comprising a fluorescent dye.

In another aspect, further provided is use of the above fluorogenic probe in fluorescent labeling of a protein, fluorescent labeling of a nucleic acid, quantification or detection of a protein, or quantification or detection of a nucleic acid.

According to one aspect of the embodiment, the fluorescent dye has a long wavelength emission (>500 nm). According to another aspect of the embodiment, the fluorescence intensity of the resulting fluorescent dye increases with increasing of environmental viscosity, the logarithm of fluorescence intensity and the logarithm of solvent viscosity have a good linear relationship. The relationship between fluorescence intensity and viscosity is in accordance with the Huffman equation and has a high slope, which indicates that the fluorescent dye is sensitive to viscosity and has a high activation multiple. According to yet another aspect of the embodiment, the fluorescent dye has good specificity to viscosity response and is insensitive to polarity changes.

According to one aspect of the embodiment, a fluorescent dye can be used to determine the viscosity of the sample, such as suitable for a test of microscopic viscosity. According to another aspect of the embodiment, the obtained fluorescent dye can specifically bind to a corresponding antibody, aptamer or amyloid and so on, or bond to a protein tag or enzyme via a ligand or inhibitor to obtain a series of fluorogenic probes for use in fluorescent labeling, quantification or monitoring of proteins, enzymes or nucleic acids.

DESCRIPTION OF THE DRAWINGS

FIG. 13 a diagram for the fluorescence emission intensity of molecular rotor 57 ($1\times10^{-5}$ M) at different viscosities;

FIG. 14 a diagram for a linear relationship between the viscosity condition and the fluorescence intensity of the molecular rotor 57 ($1\times10^{-5}$ M);

FIG. 15 is a diagram for the fluorescence emission intensity of molecular rotor 57 ($1\times10^{-5}$ M) in methanol and dichloromethane;

FIG. 16 a diagram for the fluorescence emission intensity of molecular rotor 63 ($1\times10^{-5}$ M) at different viscosities;

FIG. 17 a diagram for a linear relationship between the viscosity condition and the fluorescence intensity of the molecular rotor 63 ($1\times10^{-5}$ M);

FIG. 18 is a diagram for the fluorescence emission intensity of molecular rotor 63 ($1\times10^{-5}$ M) in methanol and dichloromethane;

DESCRIPTION OF EMBODIMENTS

Figure 1:
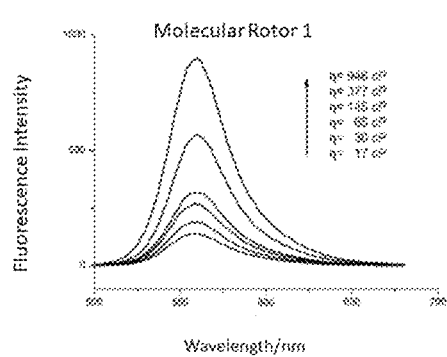
FIG. 1 is a diagram for the fluorescence emission intensity of molecular rotor 1 ($1\times10^{-5}$ M) at different viscosities.
Figure 2:
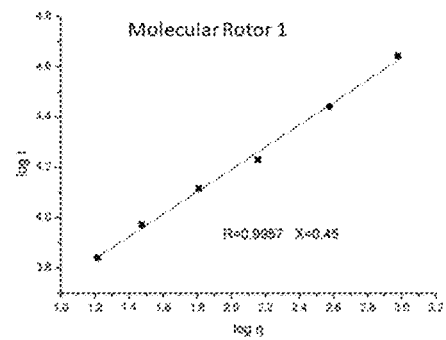
FIG. 2 is a diagram for a linear relationship between the viscosity condition and the fluorescence intensity of the molecular rotor 1 ($1\times10^{-5}$ M)
Figure 3:
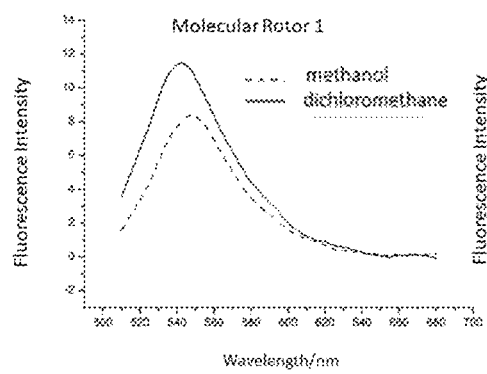
FIG. 3 is a diagram for the fluorescence emission intensity of molecular rotor 1 ($1\times10^{-5}$ M) in methanol and dichloromethane.
Figure 4:
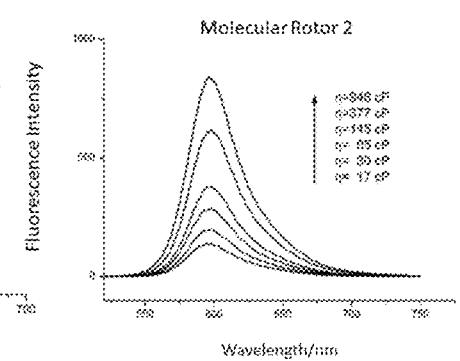
FIG. 4 is a diagram for the fluorescence emission intensity of molecular rotor 2 ($1\times10^{-5}$ M) at different viscosities.
Figure 5:
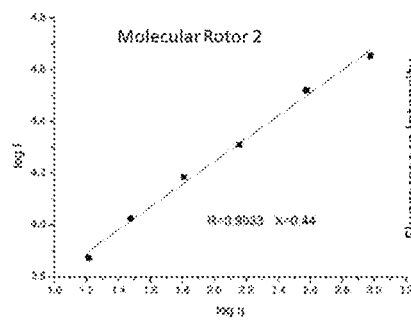
FIG. 5 a diagram for a linear relationship between the viscosity condition and the fluorescence intensity of the molecular rotor 2 ($1\times10^{-5}$ M)
Figure 6:
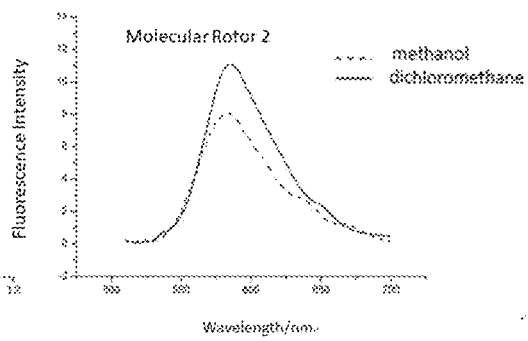
FIG. 6 is a diagram for the fluorescence emission intensity of molecular rotor 2 ($1\times10^{-5}$ M) in methanol and dichloromethane.
Figure 7:
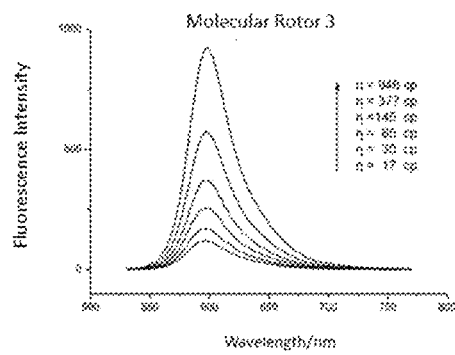
FIG. 7 a diagram for the fluorescence emission intensity of molecular rotor 3 ($1\times10^{-5}$ M) at different viscosities.
Figure 8:
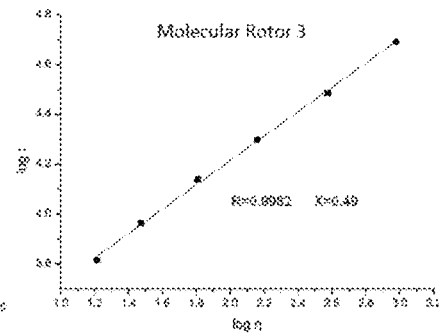
FIG. 8 a diagram for a linear relationship between the viscosity condition and the fluorescence intensity of the molecular rotor 3 ($1\times10^{-5}$ M)
Figure 9:
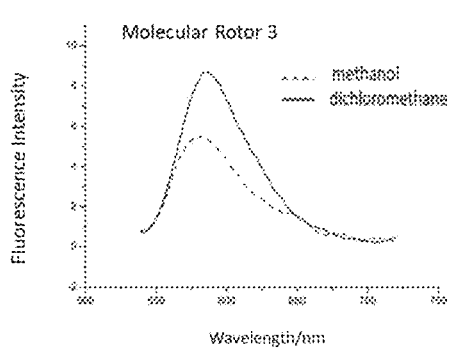
FIG. 9 is a diagram for the fluorescence emission intensity of molecular rotor 3 ($1\times10^{-5}$ M) in methanol and dichloromethane.
Figure 10:
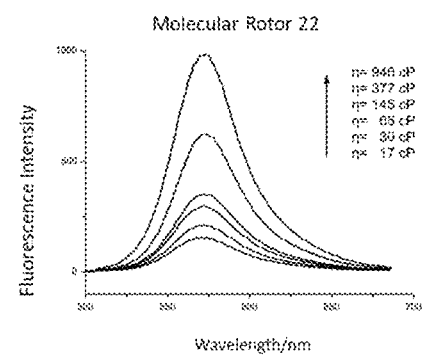
FIG. 10 a diagram for the fluorescence emission intensity of molecular rotor 22 ($1\times10^{-5}$ M) at different viscosities.
Figure 11:
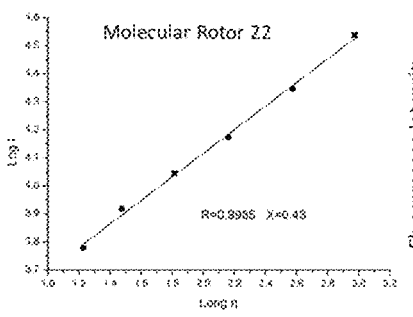
FIG. 11 a diagram for a linear relationship between the viscosity condition and the fluorescence intensity of the molecular rotor 22 ($1\times10^{-5}$ M)
Figure 12:
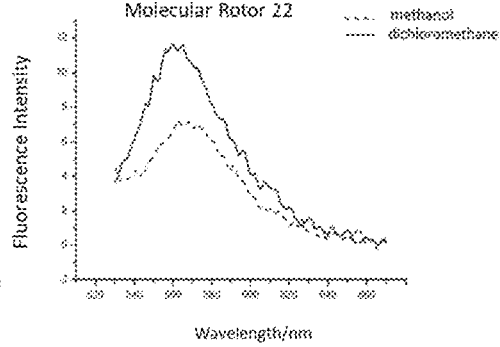
FIG. 12 is a diagram for the fluorescence emission intensity of molecular rotor 22 ($1\times10^{-5}$ M) in methanol and dichloromethane.

The embodiments of the present invention are described in detail below. These embodiments are implemented on the premise of the technical solution of the present invention. Detailed embodiments and specific operation processes are provided, but the scope of protection of the present invention is not limited to the embodiments described below.

The term "molecular rotor" described in the following examples is an abbreviation for the long-wavelength-emitting viscosity-responsive fluorescent dye of the present invention.

Example 1

Synthesis of 2-(2-cyano-2-tert-butyl formate vinyl)-5-dimethylamino-thieno[3,2,b]thiophene (Molecular Rotor 1)

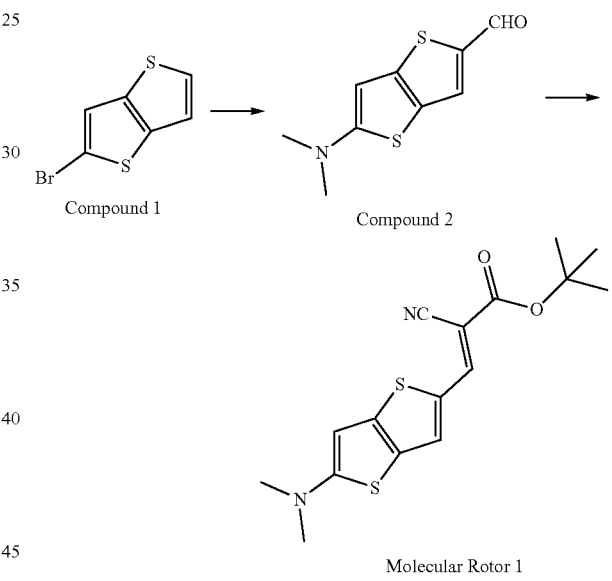

Synthesis of 2-formyl-5-dimethylamino-thieno[3,2,b]thiophene (Compound 2)

Compound 1 (0.438 g, 2 mmol) was dissolved in 15 mL of a solution of dimethylamine in toluene, to which copper powder (6.4 mg, 0.01 mmol), cuprous iodide (19 mg, 0.01 mmol) and tripotassium phosphate (0.850 g, 4 mmol) were added, and then the mixture was heated overnight in an oil bath at 80° C. under Ar atmosphere. Upon completion of the reaction, the resultant was cooled at room temperature. The system was poured into 50 mL of water, wherein 3×50 mL was extracted with dichloromethane, and the organic phases were combined and dried by rotary evaporation to give a crude product for direct use in the next step without purification.

The residue was dissolved in 15 mL of dimethylformamide. Phosphorus oxychloride (0.94 ml, 10 mmol) was slowly added under the condition of an ice bath, and then the ice bath was removed. The system was slowly returned to room temperature. After the reaction was completed, 5 ml of water was carefully added to quench this reaction, and then the system was poured into 50 mL of water, wherein 3×50 mL was extracted with dichloromethane, and the organic phases were combined and dried by rotary evaporation, followed by column chromatography to obtain a pale brown pure compound (0.317 g, 75%). $^1$H-NMR (400 MHz, DMSO-d$_6$): δ=9.78 (s, 1H), 8.21 (s, 1H), 8.05 (s, 1H), 3.15 (s, 6H).

Synthesis 2-(2-cyano-2-tert-butyl formate vinyl)-5-dimethylamino-thieno[3,2,b]thiophene (Molecular Rotor 1)

Compound 2 (0.211 g, 1.0 mmol) and tert-butyl cyano-acetate (0.169 g, 1.2 mmol) were dissolved in 20 mL of absolute ethanol, to which anhydrous piperidine was added in a catalytic amount, and the mixture was heated in an oil bath for 2 h under Ar atmosphere. After completion of the Reaction, the Resultant was Cooled at Room Temperature, and a Part of the solvent was removed by rotary evaporation. A large amount of solid was precipitated from the system, and the system was filtered. The filter cake was washed twice with cold ethanol and dried in vacuo to give a red pure compound (0.310 g, 85%). $^1$H-NMR (400 MHz, DMSO-d$_6$): δ=8.22 (s, 1H), 8.02 (s, 1H), 6.43 (s, 1H), 3.15 (s, 6H), 1.48 (s, 9H).

Example 2

Synthesis of 2-[2-cyano-2-(2-benzoxazole)-vinyl]-5-didecylamino-thieno[3,2,b]thiophene (Molecular Rotor 2)

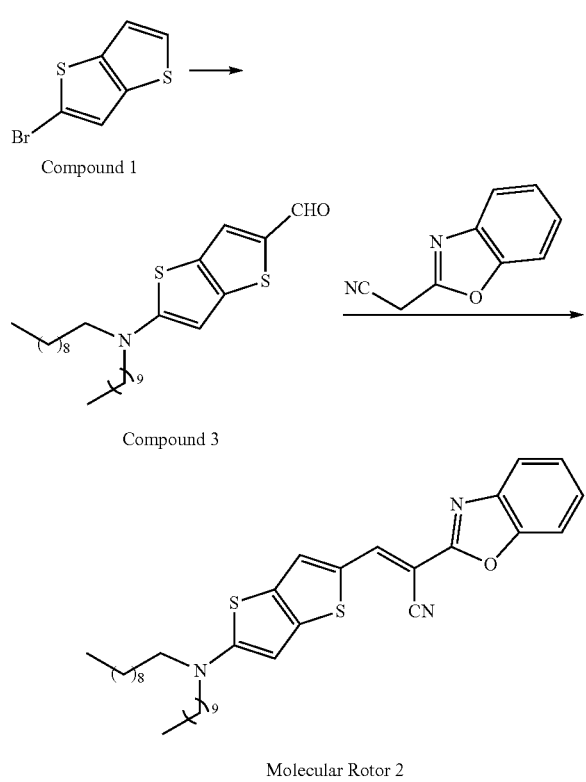

Molecular Rotor 2

Synthesis of 2-formyl-5-didecylamino-thieno[3,2,b]thiophene

It was synthesized according to the synthesis of Compound 2, with a yield of 75%. $^1$H-NMR (400 MHz, CDCl$_3$): δ=9.78 (s, 1H), 8.21 (s, 1H), 8.05 (s, 1H), 3.32 (t, 4H, J=8.20 Hz), 1.64 (m, 32H), 0.93 (t, 6H, J=8.00 Hz).

Synthesis of 2-[2-cyano-2-(2-phenylpropionazole)-vinyl]-5-didecylamino-thieno[3,2,b]thiophene (Molecular Rotor 2)

Compound 3 (0.463 g, 1.0 mmol) and 2-benzoxazole acetonitrile (0.189 g, 1.2 mmol) were dissolved in 35 mL of absolute ethanol, to which anhydrous piperidine was added in a catalytic amount, and the mixture was heated in an oil bath for 2 h under Ar atmosphere. After completion of the reaction, the resultant was cooled at room temperature, and a part of the solvent was removed by rotary evaporation. A large amount of solid was precipitated from the system, and the system was filtered. The filter cake was washed twice with cold ethanol and dried in vacuo to give a red pure compound (0.495 g, 82%). $^1$H-NMR (400 MHz, DMSO-d$_6$): δ=8.49 (s, 1H), 8.07 (s, 1H), 7.68-7.71 (m, 2H), 7.35-7.38 (m, 2H), 6.46 (s, 1H), 3.32 (t, 6H, J=8.20 Hz), 1.66 (m, 32H), 0.99 (t, 6H, J=8.00 Hz).

Example 3

Synthesis of 2-[2-cyano-2-(1,3-benzothiazol-2-yl)-vinyl]-5-(N-methyl-N-hydroxyethyl)-thieno[3,2,b]thiophene (Molecular Rotor 3)

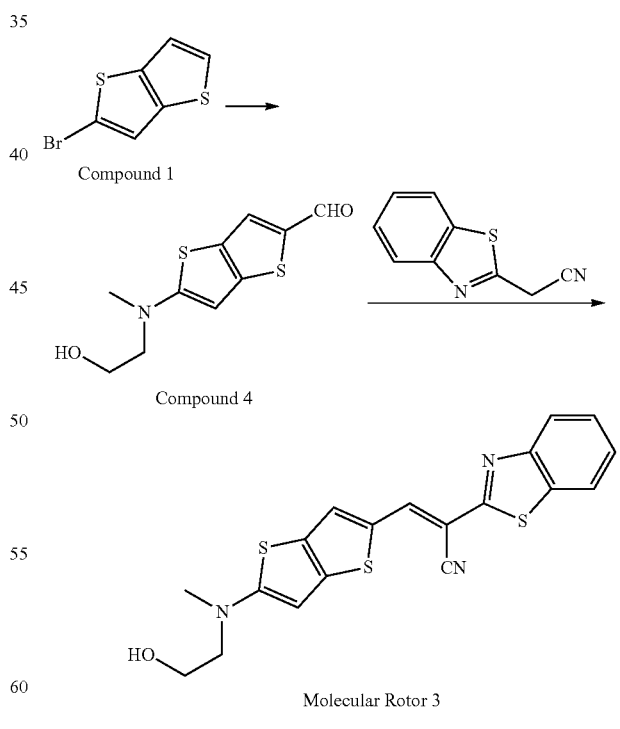

Molecular Rotor 3

Compound 4

Compound 4 was synthesized according to the synthesis of Compound 2, with a yield of 75%. $^1$H-NMR (400 MHz, DMSO-$d_6$): δ=9.78 (s, 1H), 8.21 (s, 1H), 8.05 (s, 1H), 3.59 (t, 2H, J=5.60 Hz), 3.48 (t, 2H, J=5.60 Hz), 3.15 (s, 3H).

Synthesis of 2-[2-cyano-2-(1,3-benzothiazol-2-yl)-vinyl]-5-(N-methyl-N-hydroxyethyl)-thieno[3,2,b]thiophene (Molecular Rotor 3)

Compound 4 (0.241 g, 1.0 mmol) and 2-benzothiazole acetonitrile (0.209 g, 1.2 mmol) were dissolved in 35 mL absolute ethanol, to which anhydrous piperidine was added in a catalytic amount, and the mixture was heated in an oil bath for 2 h under Ar atmosphere. After completion of the reaction, the resultant was cooled at room temperature, and a part of the solvent was removed by rotary evaporation. A large amount of solid was precipitated from the system, and the system was filtered. The filter cake was washed twice with cold ethanol and dried in vacuo to produce a red pure compound (0.318 g, 87%). $^1$H-NMR (400 MHz, DMSO-$d_6$): δ=8.45 (s, 1H), 8.09 (d, 1H, J=8.00 Hz), 8.07 (s, 1H), 7.94 (d, 1H, J=8.00 Hz), 7.51 (m, 1H), 7.41 (m, 1H), 6.45 (s, 1H), 4.92 (t, 1H, J=5.60 Hz), 3.67 (t, 2H, J=5.60 Hz), 3.49 (t, 2H, J=5.60 Hz), 3.13 (s, 3H).

Example 4

Synthesis of 6-(2,2-dicyano-vinyl)-2-[N-methyl-N-(3-sulfonic acid propyloxyethyl)]-thieno[3,2,b]thiophene (Molecular Rotor 4)

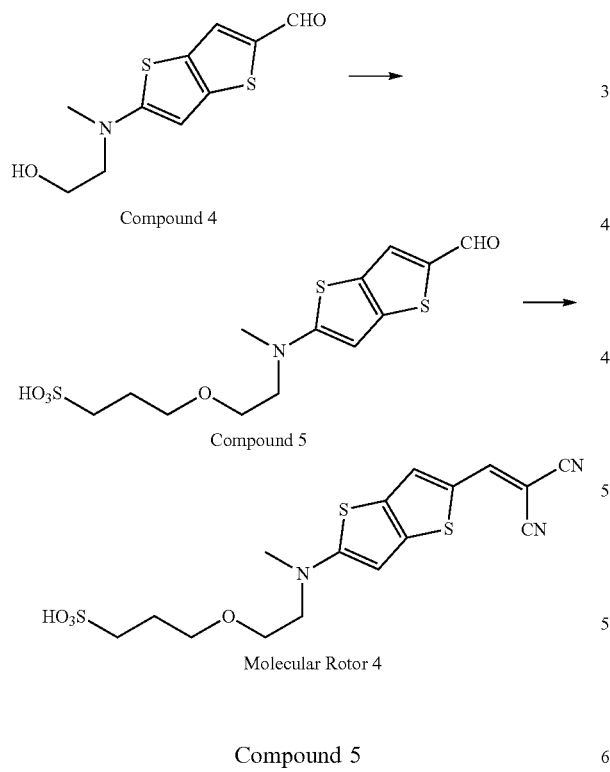

Compound 4 (0.482 g, 2.0 mmol) was dissolved in a 50 ml round bottom flask by adding 25 ml of anhydrous DMF, and 60% NaH (0.12 g, 2.5 mmol) was added at 0° C. under Ar atmosphere, followed by stirring for 30 min, and 0.5 ml of propane sultone was then added. The system gradually returned to room temperature. After the reaction was completed, 2 ml of water was added to quench the reaction. To the resultant 100 ml of water was added, and the resultant was extracted thrice with isopropyl alcohol:dichloromethane of 1:1, and the organic phases were combined. The system was dried over $Na_2SO_4$, filtered to remove $Na_2SO_4$, and subjected to rotary evaporation. The residue was separated by reversed-phase column to get a pale yellow solid (0.62 g, 85%). $^1$H-NMR (400 MHz, DMSO-$d_6$): δ=9.78 (s, 1H), 8.21 (s, 1H), 8.05 (s, 1H), 3.68 (m, 4H), 3.55 (m, 2H), 3.35 (m, 2H), 3.11 (s, 3H), 2.42 (m, 2H).

Synthesis of 6-(2,2-dicyano-vinyl)-2-[N-methyl-N-(3-sulfonic acid propyloxyethyl)]-thieno[3,2,b]thiophene (Molecular Rotor 4)

Compound 5 (0.363 g, 1.0 mmol) and malononitrile (0.079 g, 1.2 mmol) were dissolved in 20 mL of absolute ethanol, to which anhydrous piperidine was added in a catalytic amount, and the mixture was heated in an oil bath for 2 h under Ar atmosphere. After completion of the reaction, the resultant was cooled at room temperature, and a part of the solvent was removed by rotary evaporation. A large amount of solid was precipitated from the system, and the system was filtered. The filter cake was washed twice with cold ethanol and dried in vacuo to produce a red pure compound (0.310 g, 85%). $^1$H-NMR (400 MHz, $CDCl_3$): 8.21 (s, 1H), 8.05 (s, 1H), 3.68 (m, 4H), 3.55 (m, 2H), 3.35 (m, 2H), 3.11 (s, 3H), 2.42 (m, 2H).

Example 5

Synthesis of 6-(2-cyano-2-formic acid)-2-methyl-amino-thieno[3,2,b]thiophene (Molecular Rotor 5)

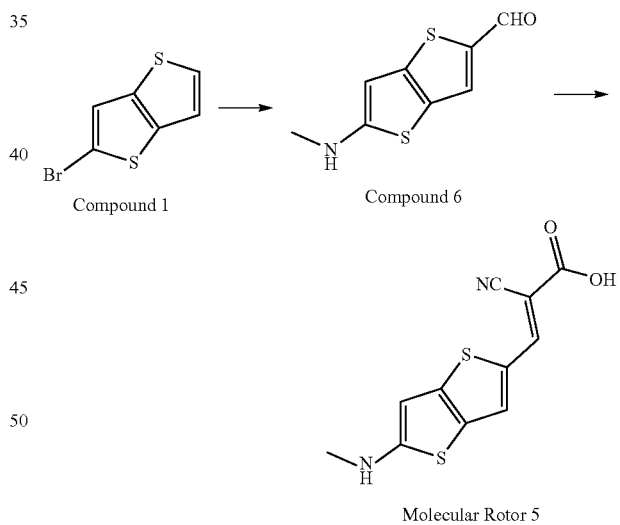

Synthesis of 2-formyl-5-methylamino-thieno[3,2,b]thiophene (Compound 6)

It was synthesized according to the synthesis of Compound 2, with a yield of 58%. $^1$H-NMR (400 MHz, $CDCl_3$): δ=9.81 (s, 1H), 8.21 (s, 1H), 8.05 (s, 1H), 3.18 (s, 3H).

Synthesis of 2-(2-cyano-2-formic acid)-5-methyl-amino-thieno[3,2,b]thiophene

Compound 6 (0.200 g, 1.0 mmol) and cyanoacetic acid (0.101 g, 1.2 mmol) were dissolved in 20 mL of absolute ethanol, to which anhydrous piperidine was added in a catalytic amount, and the mixture was heated in an oil bath for 2 h under Ar atmosphere. After completion of the reaction, the resultant was cooled at room temperature, and a part of the solvent was removed by rotary evaporation. A large amount of solid was precipitated from the system, and the system was filtered. The filter cake was washed twice with cold ethanol and dried in vacuo to produce a red pure compound (0.24 g, 91%). $^1$H-NMR (400 MHz, DMSO-$d_6$): δ=11.22 (s, 1H), δ=8.22 (s, 1H), 8.02 (s, 1H), 6.43 (s, 1H), 3.16 (s, 3H).

Example 6

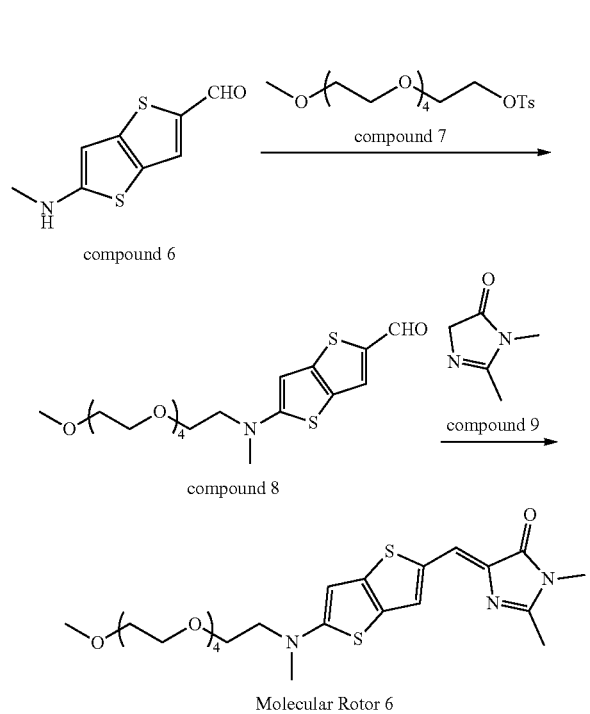

Synthesis of Compound 8

Compound 6 (1.0 g, 5 mmol) was dissolved in 100 mL of acetonitrile, to which potassium carbonate (1.4 g, 10 mmol) was added. under Ar atmosphere, Compound 7 (2.47 g, 6 mol) was refluxed overnight in an oil bath. After the reaction was completed, the resultant was cooled at room temperature and filtered, and the solvent is subjected to rotary evaporation. The residue was dissolved in methylene chloride, washed three times with water, dried over anhydrous sodium sulfate, filtered to remove $Na_2SO_4$, subjected to column chromatography after rotary evaporation to generate a pale brown pure compound (1.29 g, 59%). $^1$H-NMR (400 MHz, CDCl$_3$): δ=9.78 (s, 1H), 8.21 (s, 1H), 8.05 (s, 1H), 3.52-3.65 (m, 20H), 3.37 (s, 3H), 2.97 (s, 3H).

Synthesis of Molecular Rotor 6

Compound 8 (0.43 g, 1 mmol) was dissolved in 50 ml of absolute ethanol, to which Compound 9 (Ref. Method disclosed in the document: L X Wu, K. Burgess, J. Am. Chem. Soc. 2008, 130, 4089-4096) (0.11 g, 1.2 mmol), and 2 drops of piperidine were added, and the mixture was refluxed in an oil bath under Ar atmosphere. After comple- tion of the reaction, the resultant was cooled at room temperature, and subjected to column chromatography after rotary evaporation to obtain a pale brown pure compound (0.436 g, 83%). $^1$H-NMR (400 MHz, CDCl$_3$): δ=8.22 (s, 1H), 8.02 (s, 1H), 6.43 (s, 1H), 3.52-3.65 (m, 20H), 3.37 (s, 3H), 2.97 (s, 3H).

Example 7

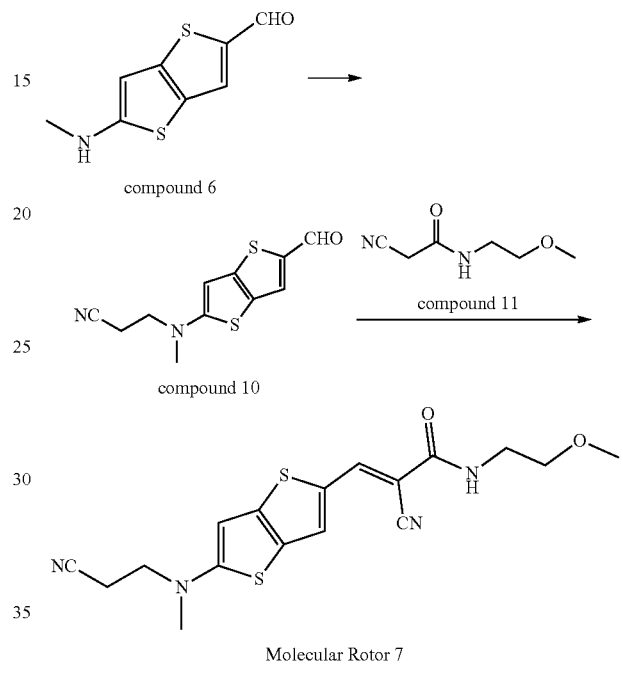

Synthesis of Compound 10

Compound 6 (1.0 g, 5 mmol) was dissolved in 100 mL of hexafluoroisopropanol, acrylonitrile (0.53 g, 10 mmol) was added, and the mixture was stirred at room temperature under Ar atmosphere. The reaction was completed, and the resultant was then chromatographed after rotary evaporation to obtain a bronzing solid (1.15 g, 92%). $^1$H-NMR (400 MHz, CDCl$_3$): δ=9.95 (s, 1H), 8.22 (s, 1H), 8.02 (s, 1H), 3.72 (t, J=6.9 Hz, 2H), 3.03 (s, 3H), 2.57 (t, J=6.9 Hz, 2H).

Synthesis of Molecular Rotor 7

Compound 10 (0.25 g, 1 mmol) was dissolved in 25 ml of absolute ethanol, to which compound 11 (see the method disclosed in WO 2004020412 (A1), 2004 Mar. 11) (0.17 g, 1.2 mmol), and 2 drops of piperidine were added, and the mixture was refluxed in an oil bath under Ar atmosphere. After completion of the reaction, the resultant was cooled at room temperature, and subjected to column chromatography after rotary evaporation to obtain a bronzing solid (1.15 g, 80%). $^1$H-NMR (400 MHz, CDCl$_3$): δ=8.22 (s, 1H), 8.02 (s, 1H), 6.43 (s, 1H), 3.72 (t, J=6.9 Hz, 2H), 3.67 (t, 2H, J=5.60 Hz), 3.35 (t, 2H, J=5.60 Hz), 3.27 (s, 3H), 3.01 (s, 3H), 3.11 (t, 2H, J=7.60 Hz), 2.57 (t, J=6.9 Hz, 2H).

Example 8

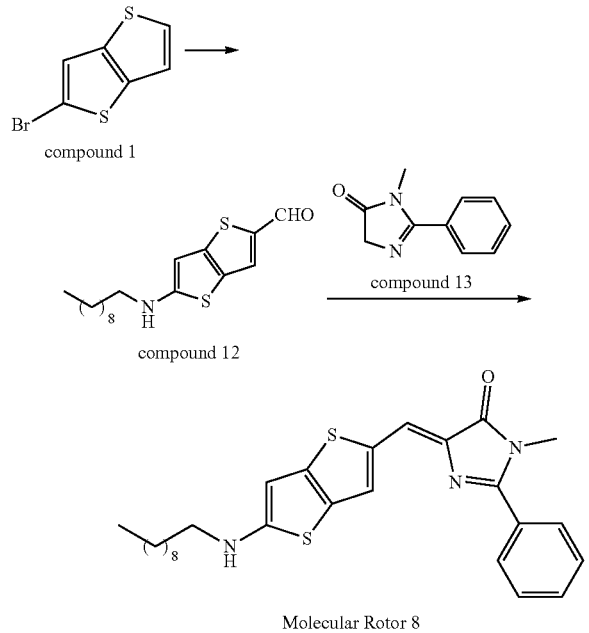

Molecular Rotor 8

Synthesis of Compound 12

Compound 12 was synthesized according to the synthesis of Compound 2, with a yield of 51%. $^1$H-NMR (400 MHz, CDCl$_3$): δ=9.95 (s, 1H), 8.22 (s, 1H), 8.02 (s, 1H), 3.12-3.09 (t, J=7.5 Hz, 2H), 1059-1.65 (m, 14H), 0.89 (t, J=7.5 Hz, 3H).

Synthesis of Compound 13

The synthesis was carried out according to the method disclosed by the literature L. X. Wu et. al. J. Am. Chem. Soc. 2008, 130, 4089-4096. $^1$H-NMR (400 MHz, CDCl): δ=7.63-7.48 (m, 5H), 4.27 (s, 2H), 3.13 (s, 3H).

Synthesis of Molecular Rotor 8

Molecular Rotor 8 was synthesized according to the synthesis of Molecular Rotor 6, with a yield of 88%. $^1$H-NMR (400 MHz, CDCl$_3$): δ=8.25 (s, 1H), 8.09 (s, 1H), 7.63-7.48 (m, 5H), 6.43 (s, 1H), 3.19 (s, 3H) 3.12-3.09 (t, J=7.5 Hz, 2H), 1059-1.65 (m, 14H), 0.89 (t, J=7.5 Hz, 3H).

Example 9

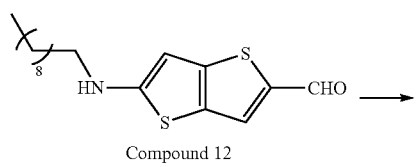

Compound 12

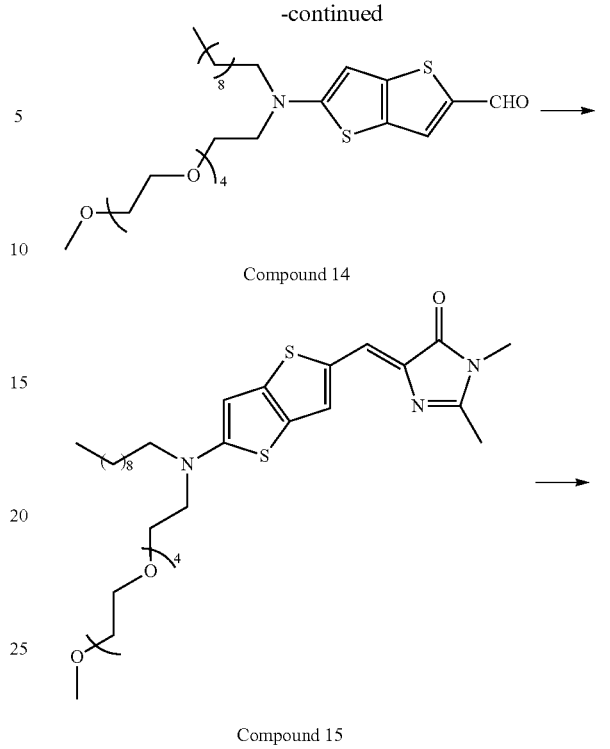

Compound 14

Compound 15

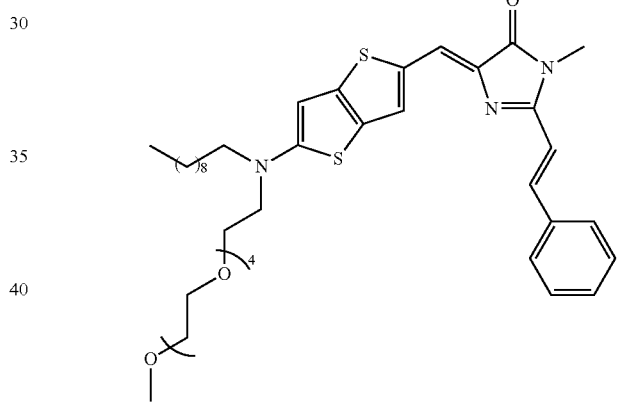

Molecular Rotor 9

Synthesis of Compound 14

Compound 14 was synthesized according to the synthesis of Compound 8, with a yield of 56%. $^1$H-NMR (400 MHz, CDCl$_3$): δ=9.95 (s, 1H), 8.22 (s, 1H), 8.02 (s, 1H), 3.52-3.65 (m, 20H), 3.37 (s, 3H), 3.12-3.09 (t, J=7.5 Hz, 2H), 1.59-1.65 (m, 14H), 0.89 (t, J=7.5 Hz, 3H).

Synthesis of Compound 15

Compound 15 was synthesized according to the synthesis of Molecular Rotor 6, with a yield of 89%. $^1$H-NMR (400 MHz, CDCl$_3$): δ=8.22 (s, 1H), 8.02 (s, 1H), 6.8 (s, 1H), 3.52-3.65 (m, 20H), 3.37 (s, 3H), 3.12-3.09 (t, J=7.5 Hz, 2H), 3.01 (s, 3H), 2.15 (s, 3H), 1.59-1.65 (m, 14H), 0.89 (t, J=7.5 Hz, 3H).

Synthesis of Molecular Rotor 9

Compound 15 (0.652 g, 1 mmol) was dissolved in 150 ml of anhydrous toluene, to which benzaldehyde (0.212 g, 2 mmol) and a catalytic amount of ZnCl₂ were added, and the mixture was refluxed in an oil bath for 24 h under Ar atmosphere, and then cooled at room temperature. The system was poured into 300 ml of brine and extracted with EtOAc trice, and the organic phases were combined, and dried over anhydrous sodium sulfate. The system was filtered to remove Na₂SO₄, and subjected to column chromatography after rotary evaporation to obtain an atropurpureus solid (0.259 g, 39%). ¹H-NMR (400 MHz, CDCl₃): δ=8.22 (s, 1H), 8.02 (s, 1H), 7.64 (d, J=8.10 Hz, 1H), 7.21 (d, J=8.10 Hz, 1H), 7.19-7.11 (m, 5H), 6.8 (s, 1H), 3.52-3.65 (m, 20H), 3.37 (s, 3H), 3.12-3.09 (t, J=7.5 Hz, 2H), 3.01 (s, 3H), 2.15 (s, 3H), 1.59-1.65 (m, 14H), 0.89 (t, J=7.5 Hz, 3H).

Example 10

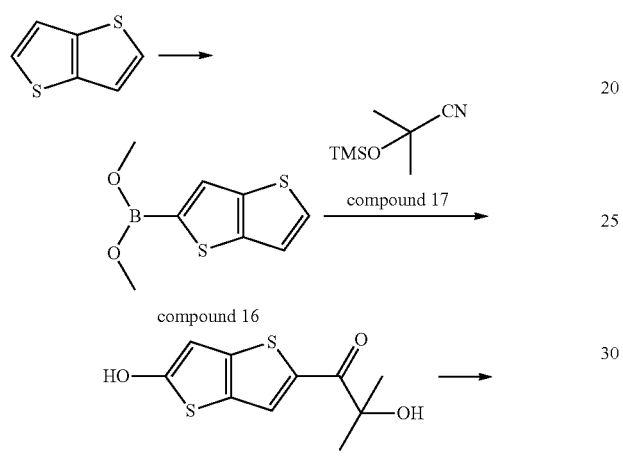

Molecular Rotor 10

Synthesis of Compound 16

Thieno[3,2-b]thiophene (1.40 g, 10 mmol) was dissolved in 120 ml of anhydrous tetrahydrofuran, and the mixture was cooled to −30° C., in which 1.6 M n-butyllithium (7.5 ml, 12 mmol) was slowly added dropwise under Ar atmosphere. After the mixture was stirred for 30 min, 5 ml of trimethyl borate was slowly added. The system was slowly warmed to room temperature and stirred overnight. The resultant was quenched by water the next day. The system was poured into 100 ml of saturated brine to separate organic phases. The organic phases were extracted twice with dichloromethane, and then combined. The organic phases were dried over anhydrous sodium sulfate, and Na₂SO₄ was removed by filtration. The organic phases were subjected to column chromatography after rotary evaporation to produce a while powder solid (1.72 g, 81%). ¹H-NMR (400 MHz, CDCl₃): δ=7.92 (s, 1H), 7.63 (d, J=5.1 Hz), 7.31 (d, J=5.3 Hz, 1H), 3.51 (s, 6H).

Synthesis of Compound 18

Compound 16 (2.12 g, 10 mmol) was dissolved in 50 ml of anhydrous tetrahydrofuran, and the mixture was cooled at −78° C., in which 1.6 M n-butyllithium (7.5 ml, 12 mmol) was slowly added dropwise under Ar atmosphere. The mixture was stirred for 2 h, and Compound 18 was added (refer to the method disclosed in the literature: F H Wang et. al. Organmetallics, 2015, 34, 86-93) (3.14 g, 20 mmol). The mixture was stirred at −78° C. for 30 min, then slowly warmed to room temperature, and stirred overnight, followed by acidifying the system until it reached pH3.5 with dilute hydrochloric acid. The system was poured into 200 ml of saturated brine to separate organic phases. The organic phases were extracted with ethyl acetate, and then combined. The organic phases were dried over anhydrous sodium sulfate, and Na₂SO₄ was removed by filtration. The organic phases were subjected to column chromatography after rotary evaporation to yield a pale yellow solid (1.48 g, 61%). ¹H-NMR (400 MHz, CDCl₃): δ=7.92 (s, 1H), 7.63 (d, J=5.1 Hz), 7.31 (d, J=5.3 Hz, 1H), 3.51 (s, 6H), 1.31 (s, 6H).

Synthesis of Molecular Rotor 10

Compound 18 (1.21 g, 5 mmol) was dissolved in anhydrous methanol, to which sodium methoxide (1.35 g, 25 mmol) and malononitrile (1.65 g, 25 ml) were added, the mixture was heated in an oil bath at 60° C. for 5 h. Upon completion of the reaction, the system was cooled at room temperature, quenched with water, poured into 150 ml of water, and acidified with dilute hydrochloric acid to pH2.0. The system was extracted with dichloromethane. The organic phases were combined, dried over anhydrous sodium sulfate, and Na₂SO₄ was removed by filtration. The organic phases were subjected to column chromatography after rotary evaporation to produce a pale yellow solid (0.45 g, 31%). ¹H-NMR (400 MHz, CDCl₃): δ=7.92 (s, 1H), 7.63 (d, J=5.1 Hz), 7.31 (d, J=5.3 Hz, 1H), 3.51 (s, 6H), 1.34 (s, 6H).

Example 11

Synthesis of 6-(2-cyano-2-tert-butyl formate vinyl)-2-dimethylamino-thieno[3,2-B:2',3'-D]thiophene (Molecular Rotor 11)

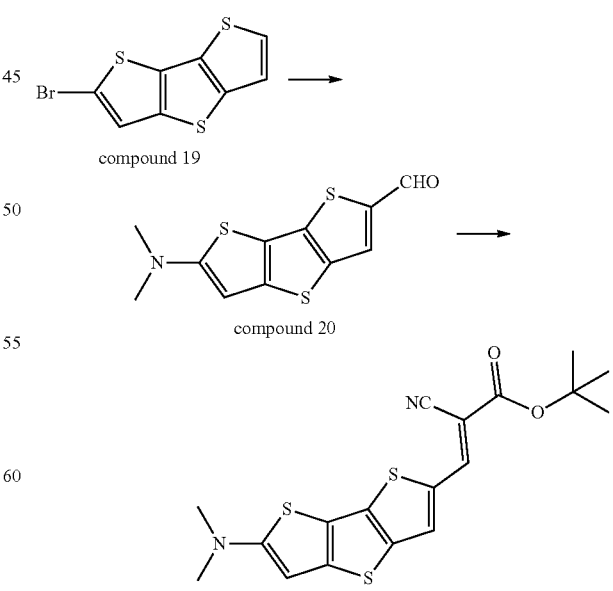

Molecular Rotor 11

2-Bromo-6 aldehyde-thieno[3,2-B:2',3'-D]thiophene

The synthesis was carried out by the method disclosed in WO2009152165(A2), 2009 Dec. 17. $^1$H-NMR (400 MHz, DMSO-d$_6$): δ=7.84 (s, 1H), 7.37 (s, 1H), 7.24 (s, 1H), 3.15 (s, 6H).

2-N,N-dimethyl-6 aldehyde-thieno[3,2-B:2',3'-D]thiophene

It was synthesized according to the synthesis of Compound 2, with a yield of 51%. $^1$H-NMR (400 MHz, DMSO-d$_6$): δ=10.04 (s, 1H), 7.84 (s, 1H), 7.24 (s, 1H), 3.15 (s, 6H).

Synthesis of 6-(2-cyano-2-tert-butyl formate vinyl)-2-dimethylamino-thieno[3,2-B:2',3'-D]thiophene (Molecular Rotor 11)

With reference to the synthesis of Molecular Rotor 1, the yield was 85%. $^1$H-NMR (400 MHz, DMSO-d$_6$): δ=8.45 (s, 1H), 7.85 (s, 1H), 6.45 (s, 1H), 3.15 (s, 6H), 1.48 (s, 9H).

Example 12

Synthesis of 6-[2-cyano-2-(2-phenylpropionazole)-vinyl]-2-dimethylamino-thieno[3,2-B:2',3'-D]thiophene (Molecular Rotor 12)

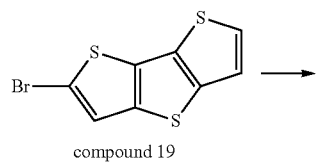

compound 19

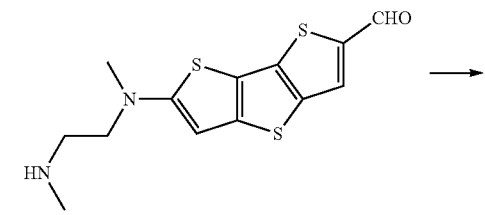

compound 21

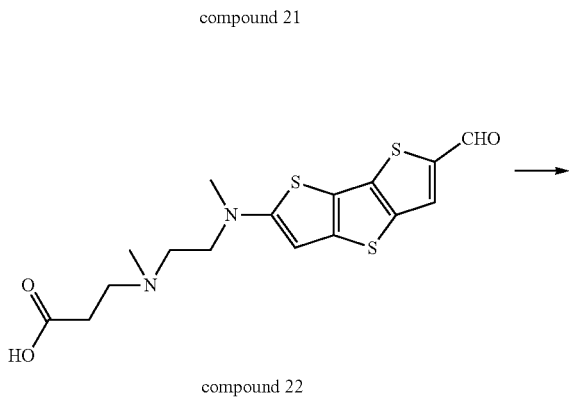

compound 22

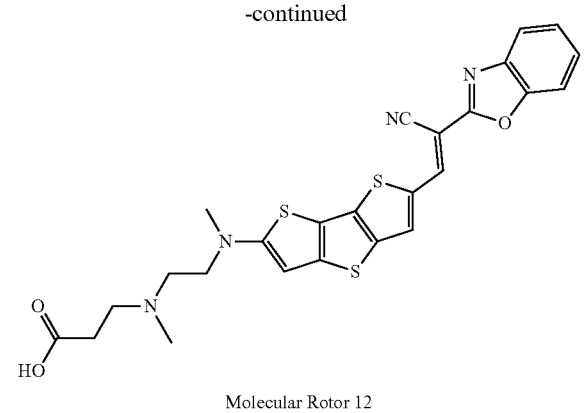

Molecular Rotor 12

Compound 21

Compound 21 was synthesized according to the synthesis of Compound 2, with a yield of 67%. $^1$H-NMR (400 MHz, DMSO-d$_6$): δ=10.0 (s, 1H), 7.84 (s, 1H), 7.24 (s, 1H), 3.82 (t, 2H, J=7.8 Hz), (t, 2H, J=7.8 Hz), 3.15 (s, 6H).

Compound 22

Compound 21 (0.648 g, 2.0 mmol) was placed in a 100 ml round bottom flask, in which 60 ml of anhydrous acetone solvent and then 1 ml of methyl iodide were added, and the mixture was stirred at room temperature under Ar atmosphere. After completion of the reaction, the supernatant was decanted. The precipitate was purified by reverse chromatography to give a solid (0.75 g, 80%). $^1$H-NMR (400 MHz, DMSO-d$_6$): δ=10.1 (s, 1H), 7.84 (s, 1H), 7.24 (s, 1H), 4.03 (t, 2H, J=7.8 Hz), (t, 2H, J=7.8 Hz), 3.29 (s, 6H), 3.19 (s, 5H), 2.52 (m, 2H).

Synthesis of 6-[2-cyano-2-(2-phenylpropionazole)-vinyl]-2-dimethylamino-thieno[3,2-B:2',3'-D]thiophene With reference to the synthesis of Molecular Rotor 2, the yield was 81%. $^1$H-NMR (400 MHz, DMSO-d$_6$): δ=8.49 (s, 1H), 7.85 (s, 1H), 7.68-7.71 (m, 2H), 7.35-7.38 (m, 2H), 6.46 (s, 1H), 7.84 (s, 1H), 7.24 (s, 1H), 4.03 (t, 2H, J=7.8 Hz), (t, 2H, J=7.8 Hz), 3.29 (s, 6H), 3.19 (s, 5H), 2.41 (m, 2H).

Example 13

Synthesis of 6-[2-cyano-2-(1,3-benzothiazol-2-yl)-vinyl]-2-N-m ethylamino-N-acetic acid-dithiophene [3,2-B:2'3'-D]thiophene (Molecular Rotor 13)

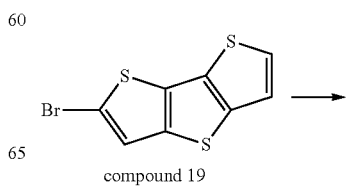

compound 19

-continued

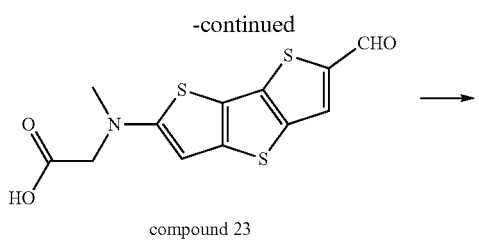

compound 23

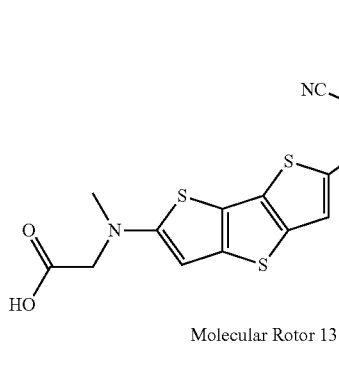

Molecular Rotor 13

Compound 23

Compound 23 was synthesized according to the synthesis of Compound 2, with a yield of 41%. $^1$H-NMR (400 MHz, DMSO-d$_6$): δ=10.04 (s, 1H), 7.84 (s, 1H), 7.24 (s, 1H), 4.12 (s, 2H), 3.15 (s, 3H).

Synthesis of 6-[2-cyano-2-(1,3-benzothiazol-2-yl)-vinyl]-2-dimethylamino-dithieno[3,2-B:2',3'-D]thiophene It was synthesized according to the synthesis of Molecular Rotor 3, with a yield of 78%. $^1$H-NMR (400 MHz, DMSO-d$_6$): δ=8.09 (d, 1H, J=8.00 Hz), 7.94 (d, 1H, J=8.00 Hz), 7.84 (s, 1H), 7.57 (s, 1H), 7.51 (m, 1H), 7.41 (m, 1H), 6.45 (s, 1H), 4.92 (t, 1H, J=5.60 Hz), 4.12 (s, 2H), 3.15 (s, 3H).

Example 14

Synthesis of 6-[2-cyano-2-(1,3-benzothiazol-2-yl)-vinyl]-2-dimethylamino-thieno[3,2-B:2',3'-D]thiophene (Molecular Rotor 14)

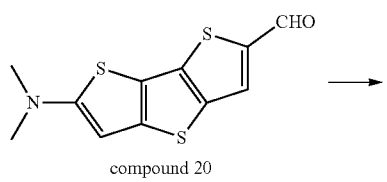

compound 20

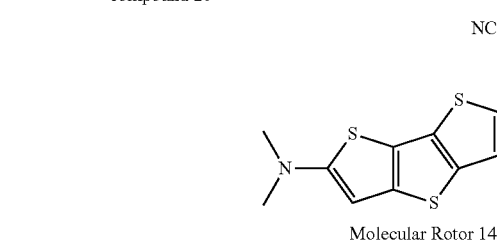

Molecular Rotor 14

Synthesis of 6-[2-cyano-2-(1,3-benzothiazol-2-yl)-vinyl]-2-dimethylamino-thieno[3,2-B:2',3'-D]thiophene It was synthesized according to the synthesis of Molecular Rotor 4, with a yield of 87%. $^1$H-NMR (400 MHz, DMSO-d$_6$): δ=7.84 (s, 1H), 7.24 (s, 1H), 6.45 (s, 1H), 3.15 (s, 6H).

Example 15

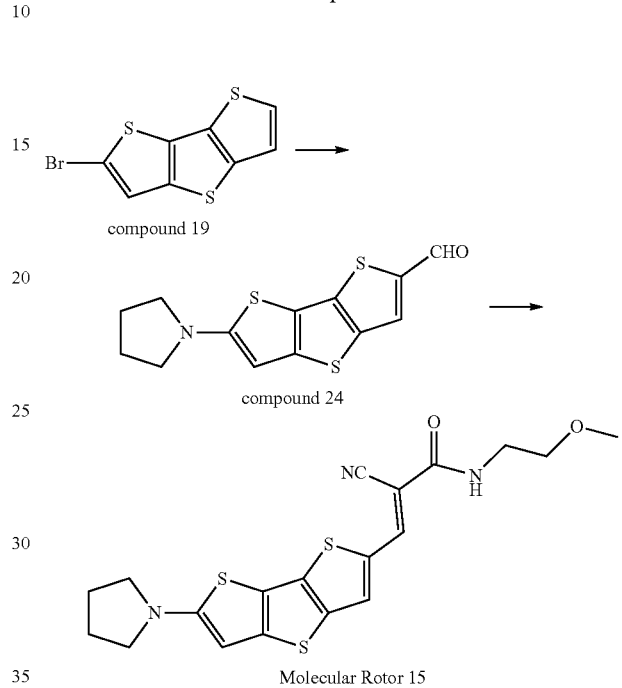

Synthesis of Compound 24

Please refer to the method for the synthesis of Compound 2: $^1$H-NMR (400 MHz, DMSO-d$_6$): δ=9.97 (s, 1H), 7.85 (s, 1H), 7.24 (s, 1H), 3.41 (t, J=5.5 Hz, 4H), 2.12 (t, J=5.5 Hz, 4H).

Synthesis of Molecular Rotor 15

Molecular Rotor 15 was synthesized according to the synthesis of Molecular Rotor 7, with a yield of 91%. $^1$H-NMR (400 MHz, DMSO-d$_6$): δ=7.85 (s, 1H), 7.24 (s, 1H), 6.94 (s, 1H), 6.50 (s, 1H), 3.48-3.52 (m, 4H), 3.41 (t, J=5.5 Hz, 4H), 3.38 (s, 3H), 2.12 (t, J=5.5 Hz, 4H).

Example 16

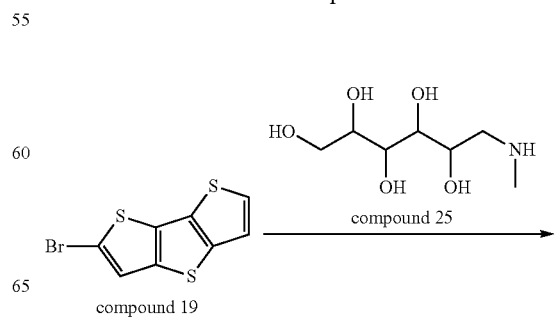

compound 19

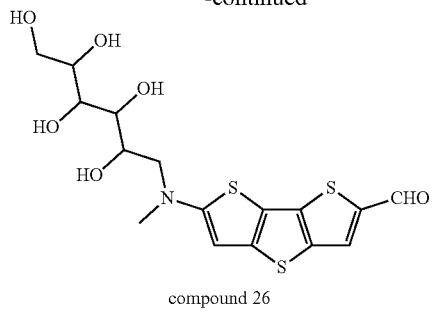

compound 26

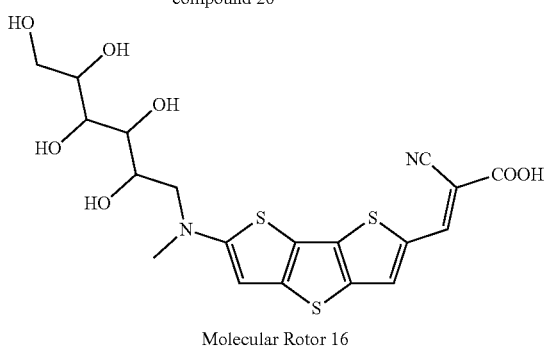

Molecular Rotor 16

Synthesis of Compound 25

Please refer to the synthesis method disclosed by the literature: H. Wang et. al. Tetrahedron Letters. 2007, 48, 3471-3474. $^1$H-NMR (400 MHz, DMSO-d$_6$): δ=4.56-4.14 (m, 4H), 3.91-3.37 (m, 8H), 3.19 (s, 3H).

Synthesis of Compound 26

Please refer to the synthesis method of Compound 2: $^1$H-NMR (400 MHz, DMSO-d$_6$): δ=7.84 (s, 1H), 7.24 (s, 1H), 6.42 (s, 1H), 6.02 (d, 1H), 4.56-4.14 (m, 4H), 3.91-3.37 (m, 8H), 3.19 (s, 3H).

Synthesis of Molecular Rotor 16

Please refer to the synthesis method of Molecular Rotor 5: $^1$H-NMR (400 MHz, DMSO-d$_6$): δ=11.01 (s, 1H), δ=7.84 (s, 1H), 7.24 (s, 1H), 6.42 (s, 1H), 6.02 (d, 1H), 4.56-4.14 (m, 4H), 3.91-3.37 (m, 8H), 3.19 (s, 3H).

Example 17

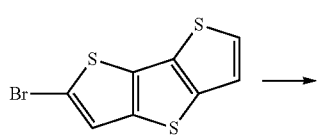

compound 19

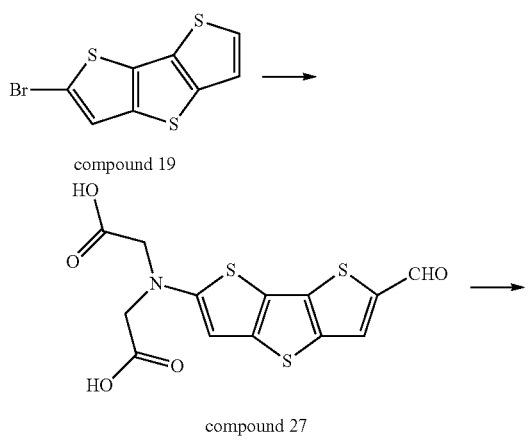

compound 27

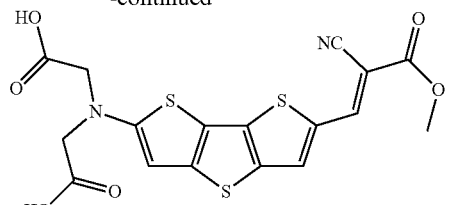

Molecular Rotor 17

Synthesis of Compound 27

Please refer to the synthesis method of Compound 2: $^1$H-NMR (400 MHz, DMSO-d$_6$): δ=7.84 (s, 1H), 7.24 (s, 1H), 6.42 (s, 1H), 4.14 (s, 4H).

Synthesis of Molecular Rotor 17

Please refer to the synthesis method of Molecular Rotor 1: $^1$H-NMR (400 MHz, CDCl$_3$): δ=7.84 (s, 1H), 7.24 (s, 1H), 6.42 (s, 1H), 4.14 (s, 4H), 4.01 (s, 3H).

Example 18

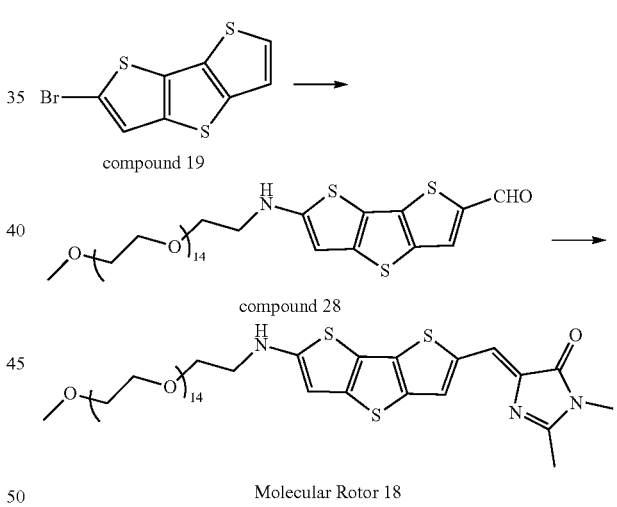

Molecular Rotor 18

Synthesis of Compound 28

Please refer to the synthesis method of Compound 2: $^1$H-NMR (400 MHz, CDCl$_3$): δ=9.95 (s, 1H), 7.84 (s, 1H), 7.24 (s, 1H), 3.52-3.65 (m, 60H), 3.37 (s, 3H).

Synthesis of Molecular Rotor 18

Molecular Rotor 18 was synthesized according to the synthesis of Molecular Rotor 6, with a yield of 90%, $^1$H-NMR (400 MHz, CDCl$_3$): δ=7.84 (s, 1H), 7.24 (s, 1H), 6.98 (s, 1H), 3.52-3.65 (m, 60H), 3.37 (s, 3H), 3.0 (s, 3H), 2.15 (s, 3H).

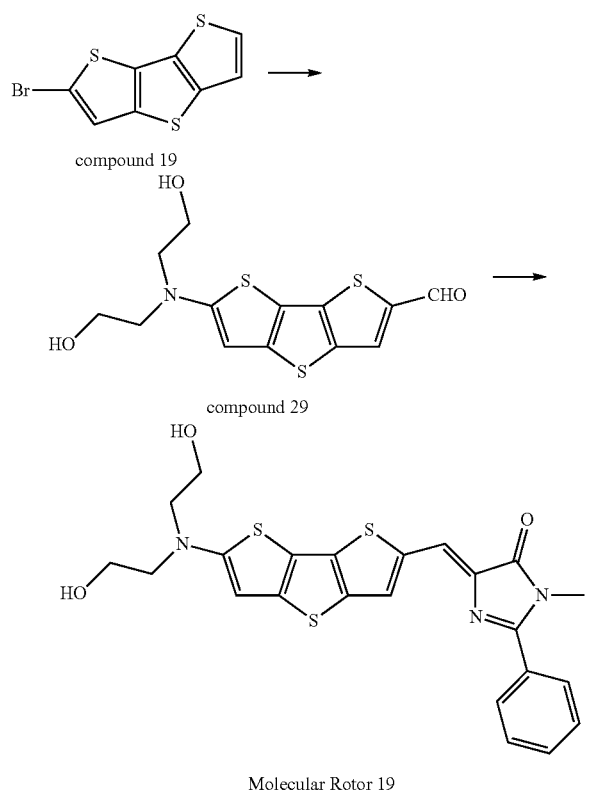

Example 19

Synthesis of Compound 29

Compound 29 was synthesized according to the synthesis of Compound 2, with a yield of 54%. $^1$H-NMR (400 MHz, CDCl$_3$): δ=9.95 (s, 1H), 7.84 (s, 1H), 7.24 (s, 1H), 3.59 (t, 4H, J=5.60 Hz), 3.48 (t, 4H, J=5.60 Hz).

Synthesis of Molecular Rotor 19

Molecular Rotor 19 was synthesized according to the synthesis of Molecular Rotor 8, with a yield of 89%. $^1$H-NMR (400 MHz, CDCl$_3$): δ=7.84 (s, 1H), 7.63-7.58 (m, 5H), 7.24 (s, 1H), 3.59 (t, 4H, J=5.60 Hz), 3.48 (t, 4H, J=5.60 Hz), 3.13 (s, 3H).

Example 20

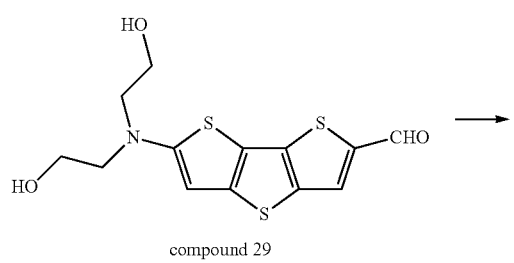

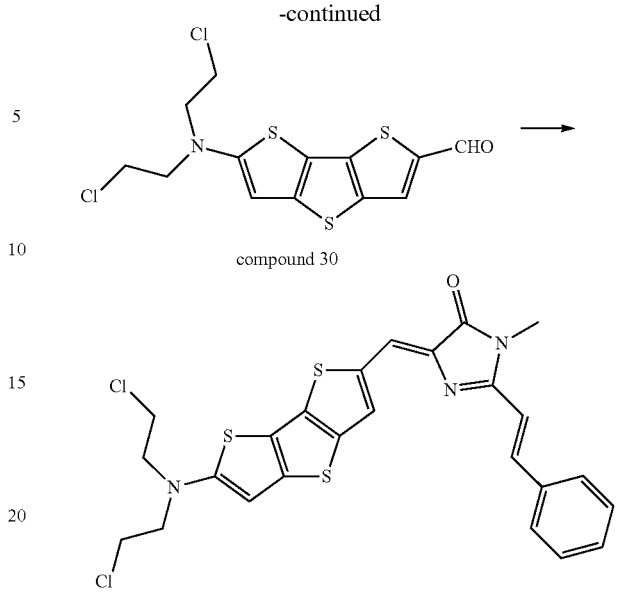

Synthesis of Compound 30

Compound 29 (0.327 g, 1 mmol) was dissolved in 25 mL anhydrous dichloromethane. After the system was cooled at 0° C., a solution of thionyl chloride (0.22 ml, 3 mmol) in 5 ml of anhydrous dichloromethane was slowly added dropwise under Ar atmosphere, and then the system was slowly warmed at room temperature, stirred for 2 h, and subjected to rotary evaporation to remove the solvent. The residue was dissolved in dichloromethane, and washed trice with saturated brine. The organic phases were dried over anhydrous sodium sulfate, filtered to remove Na$_2$SO$_4$, and subjected to column chromatography after rotary evaporation to obtain an atropurpureus solid (0.298 g, 82%). $^1$H-NMR (400 MHz, CDCl$_3$): δ=9.95 (s, 1H), 7.84 (s, 1H), 7.24 (s, 1H), 3.69 (t, 4H, J=5.60 Hz), 3.28 (t, 4H, J=5.60 Hz).

Synthesis of Molecular Rotor 20

Molecular Rotor 20 was synthesized according to the synthesis of Molecular Rotor 9, with a yield of 41%. $^1$H-NMR (400 MHz, CDCl$_3$): δ=8.0 (d, J=16.0 Hz, 1H), 7.91 (d, J=8.5 Hz, 2H), 7.84 (s, 1H), 7.38-7.45 (m, 3H), 7.24 (s, 1H), 7.15 (d, J=16.0 Hz, 1H), 6.98 (s, 1H), 3.69 (t, 4H, J=5.60 Hz), 3.28 (t, 4H, J=5.60 Hz), 3.13 (s, 3H).

Example 21

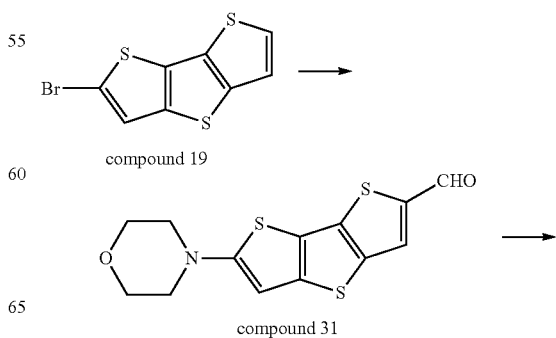

-continued

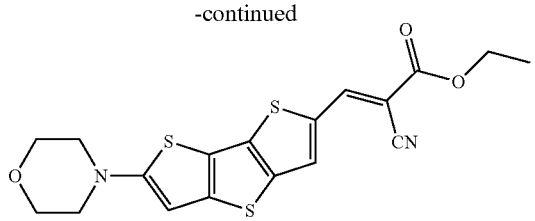

Molecular Rotor 21

Synthesis of Compound 31

Compound 31 was synthesized according to the synthesis of Compound 2, with a yield of 61%. $^1$H-NMR (400 MHz, CDCl$_3$): δ=9.95 (s, 1H), 7.84 (s, 1H), 7.24 (s, 1H), 3.94-3.76 (m, 4H), 3.42-3.26 (m, 4H).

Synthesis of Molecular Rotor 21

The Molecular Rotor 21 was synthesized in accordance with the synthesis method of the Molecular Rotor 1, with a yield of 92%. $^1$H-NMR (400 MHz, CDCl$_3$): δ=7.84 (s, 1H), 7.24 (s, 1H), 6.98 (s, 1H), 3.71 (q, J=5.80 Hz, 2H), 3.59 (t, 4H, J=5.60 Hz), 3.48 (t, 4H, J=5.60 Hz), 1.25 (t, J=5.80 Hz, 3H).

Example 22

Synthesis of Molecular Rotor 22

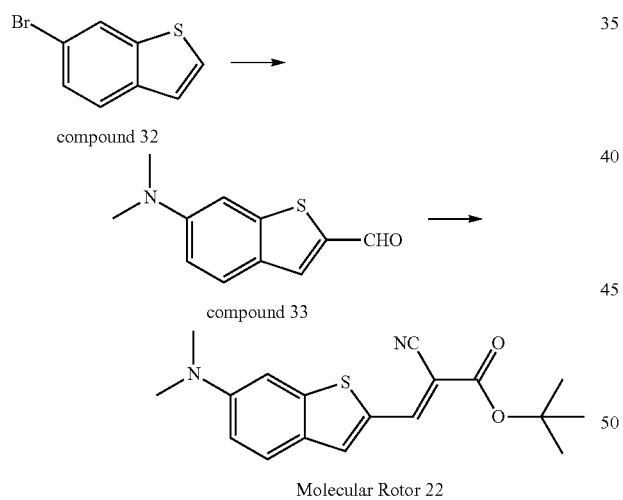

Synthesis of Compound 33

Compound 33 was synthesized according to the synthesis of Compound 2, with a yield of 47%. $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.21 (s, 6H).

Molecular Rotor 22

Molecular Rotor 22 was synthesized according to the synthesis of Molecular Rotor 1, with a yield of 91%. $^1$H-NMR (400 MHz, CDCl$_3$): δ=8.20 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.21 (s, 6H), 1.51 (s, 9H).

Example 23

Synthesis of Molecular Rotor 23

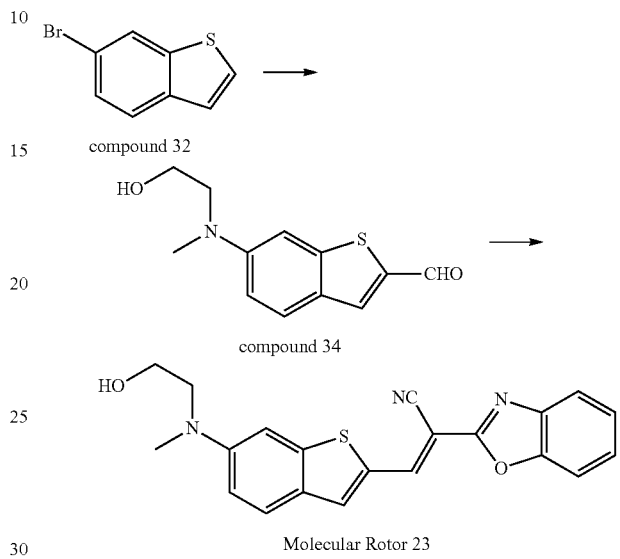

Synthesis of Compound 34

Please refer to the synthesis method of Compound 2: $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.61 (t, J=8.0 Hz, 3H), 3.34 (t, J=8.0 Hz, 3H), 3.21 (s, 3H).

Synthesis of Molecular Rotor 23

Molecular Rotor 23 was synthesized according to the synthesis of Molecular Rotor 2, with a yield of 93%. $^1$H-NMR (400 MHz, DMSO-d$_6$): δ=8.45 (s, 1H), 8.09 (d, J=8.00 Hz, 2H), 8.07 (s, 1H), 7.94 (d, J=8.00 Hz, 2H), 7.51 (m, 1H), 7.41 (m, 1H), 6.45 (s, 1H), 3.61 (t, 3H, J=8.0 Hz), 3.34 (t, J=8.0 Hz, 3H), 3.21 (s, 3H).

Example 24

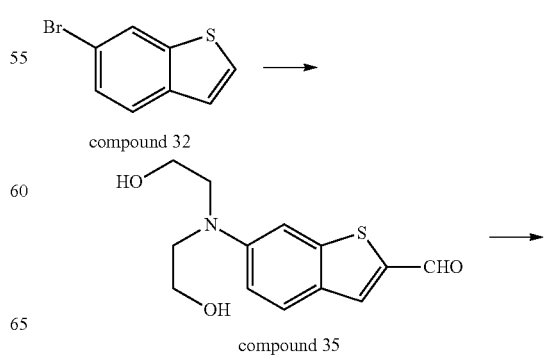

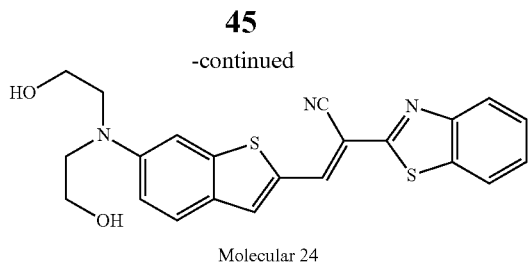

Molecular 24

Synthesis of Compound 35

Please refer to the synthesis method of Compound 2: $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.63 (t, J=8.0 Hz, 4H), 3.37 (t, J=8.0 Hz, 4H).

Synthesis of Molecular Rotor 24

Molecular Rotor 24 was synthesized according to the synthesis of Molecular Rotor 3, with a yield of 91%. $^1$H-NMR (400 MHz, DMSO-d$_6$): δ=8.09 (d, 1H, J=8.00 Hz), 7.94 (d, 1H, J=8.00 Hz), 7.81 (s, 1H), 7.68 (d, J=9.0 Hz, 1H), 7.51 (m, 1H), 7.41 (m, 1H), 6.92 (d, J=2.0 Hz, 1H), 6.82 (d, J=9.1, 2.3 Hz, 1H), 6.45 (s, 1H), 3.63 (t, J=8.0 Hz, 4H), 3.37 (t, J=8.0 Hz, 4H).

Example 25

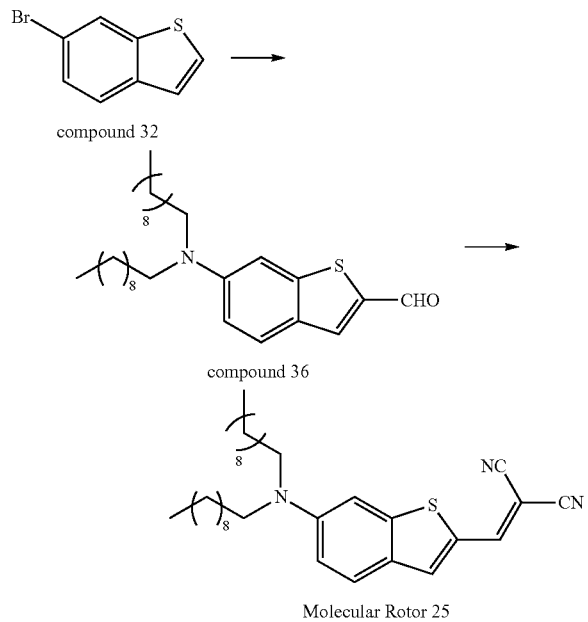

Synthesis of Compound 36

Compound 36 was synthesized according to the synthesis of Compound 2, with a yield of 31%. $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.32 (t, 4H, J=8.20 Hz), 1.64 (m, 32H), 0.93 (t, 6H, J=8.00 Hz).

Synthesis of Molecular Rotor 25

Molecular Rotor 25 was synthesized according to the synthesis of Molecular Rotor 4, with a yield of 88%. $^1$H-NMR (400 MHz, CDCl$_3$): δ=7.81 (s, 1H), 7.68 (d, J=9.0 Hz, 1H), 7.31 (s, 1H), 6.92 (d, J=2.0 Hz, 1H), 6.82 (d, J=9.1, 2.3 Hz, 1H), 3.32 (t, 4H, J=8.20 Hz), 1.64 (m, 32H), 0.93 (t, 6H, J=8.00 Hz).

Example 26

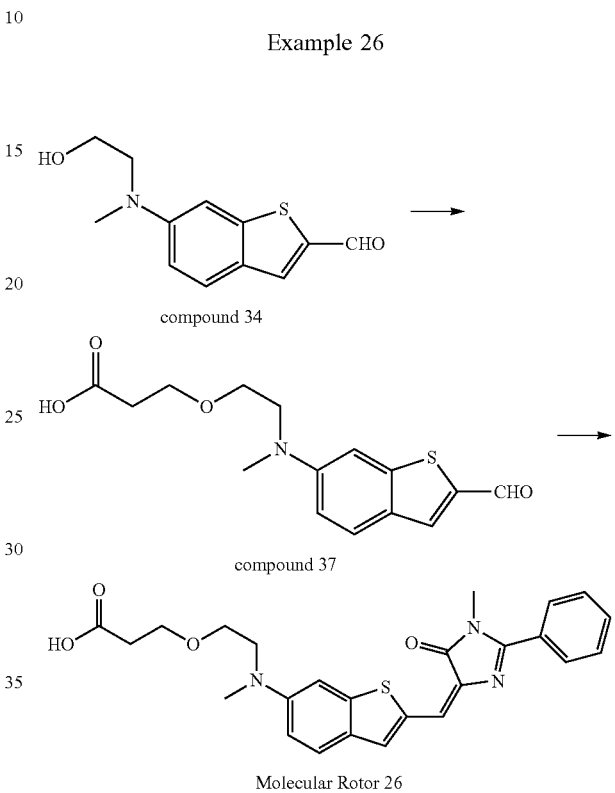

Synthesis of Compound 37

Compound 34 (0.235 g, 1 mmol) was dissolved in 25 ml of anhydrous dimethylformamide, and 60% sodium hydride (0.06 g, 1.5 mmol) in ice bath was added and stirred for 30 min, to which β-propiolactone was added. The system was slowly warmed at room temperature. After completion of the reaction, the system was quenched with water, and then dried by rotary evaporation following column chromatography to give a pale yellow solid (0.24 g, 78%). $^1$H-NMR (400 MHz, DMSO-d$_6$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.82 (t, J=5.7 Hz, 2H), 3.54 (t, J=7.2 Hz, 2H), 3.42 (t, J=7.2 Hz, 2H), 2.65 (t, J=5.7 Hz, 2H).

Synthesis of Molecular Rotor 26

Molecular Rotor 26 was synthesized according to the synthesis of Molecular Rotor 8, with a yield of 88%. $^1$H-NMR (400 MHz, DMSO-d$_6$): δ=7.81 (s, 1H), 7.68 (d, J=9.0 Hz, 1H), 7.63-7.48 (m, 5H), 6.92 (d, J=2.0 Hz, 1H), 6.82 (d, J=9.1, 2.3 Hz, 1H), 3.82 (t, J=5.7 Hz, 2H), 3.54 (t, J=7.2 Hz, 2H), 3.42 (t, J=7.2 Hz, 2H), 3.13 (s, 3H), 2.65 (t, J=5.7 Hz, 2H.)

Example 27

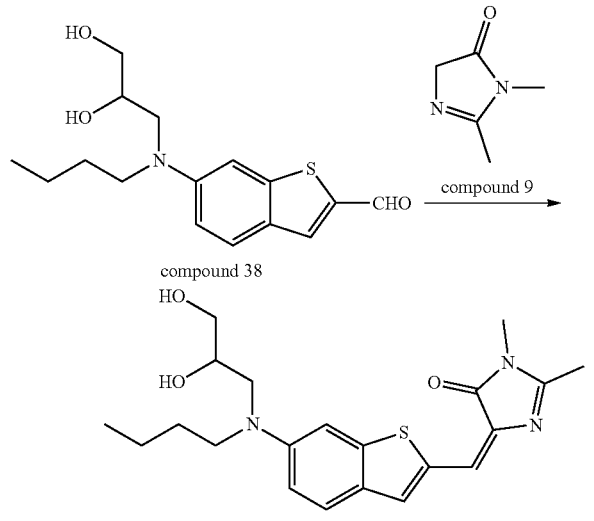

Synthesis of Compound 38

Please refer to the literature: H. Wang et. al. Tetrahedron letters. 2007. 48. 3471-3474. $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 4.09 (m, 1H), 3.83 (m, 1H), 3.66-3.52 (m, 5H), 3.00 (s, 3H), 2.21 (s, 3H), 1.86 (s, 6H), 1.67 (m, 2H), 1.42 (m, 2H), 1.02 (t, J=5.0 Hz, 3H).

Synthesis of Molecular Rotor 27

Compound 38 (0.205 g, 1.0 mmol) was put in a 50 ml round bottom flask, to which Compound 9 (Ref. The method disclosed in the literature: L X Wu, K. Burgess, J. Am. Chem. Soc. 2008, 130, 4089-4096) (0.11 g, 1.2 mmol) and a catalytic amount of anhydrous zinc chloride were added, and the solid mixture was dissolved by adding 20 ml of absolute ethanol. The system was refluxed in an oil bath under Ar atmosphere. After completion of the reaction, the resultant was cooled at room temperature, and subjected to rotary evaporation to remove part of solvent. The residue was filtered, the filter cake was washed with cold ethanol and dried in vacuo to obtain a product (0.24 g, 80%). $^1$H-NMR (400 MHz, CDCl$_3$): δ=7.81 (s, 1H), 7.68 (d, J=9.0 Hz, 1H), 6.92 (d, J=2.0 Hz, 1H), 6.82 (d, J=9.1, 2.3 Hz, 1H), 4.09 (m, 1H), 3.83 (m, 1H), 3.66-3.52 (m, 5H), 3.00 (s, 3H), 1.86 (s, 6H), 1.67 (m, 2H), 1.42 (m, 2H), 1.02 (t, J=5.0 Hz, 3H).

Example 28

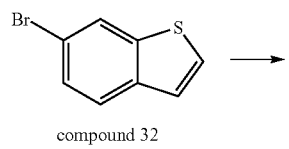

compound 32

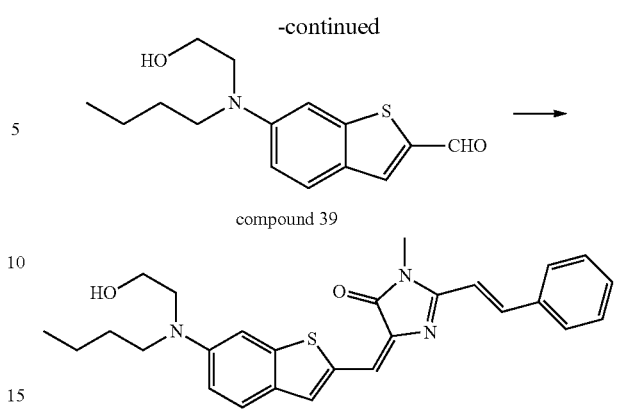

Synthesis of Compound 39

Please refer to the literature: H. Wang et. al. Tetrahedron letters. 2007. 48. 3471-3474. $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.63 (t, J=8.0 Hz, 2H), 3.37 (t, J=8.0 Hz, 2H), 3.00 (s, 3H), 2.21 (s, 3H), 1.86 (s, 6H), 1.67 (m, 2H), 1.42 (m, 2H), 1.02 (t, J=5.0 Hz, 3H).

Synthesis of Molecular Rotor 28

The Molecular Rotor 28 was synthesized in accordance with the synthesis method of the Molecular Rotor 9, and achieved a yield of 29%. $^1$H-NMR (400 MHz, CDCl$_3$): δ=8.00 (d, J=16.0 Hz, 1H), 7.85 (d, J=8.0 Hz, 2H), 7.81 (s, 1H), 7.68 (d, J=9.0 Hz, 1H), 7.38-7.45 (m, 3H), 7.24 (d, J=16.0 Hz, 1H), 6.92 (d, J=2.0 Hz, 1H), 6.82 (d, J=9.1, 2.3 Hz, 1H), 3.63 (t, J=8.0 Hz, 2H), 3.37 (t, J=8.0 Hz, 2H), 3.00 (s, 3H), 2.21 (s, 3H), 1.86 (s, 6H), 1.67 (m, 2H), 1.42 (m, 2H), 1.02 (t, J=5.0 Hz, 3H).

Example 29

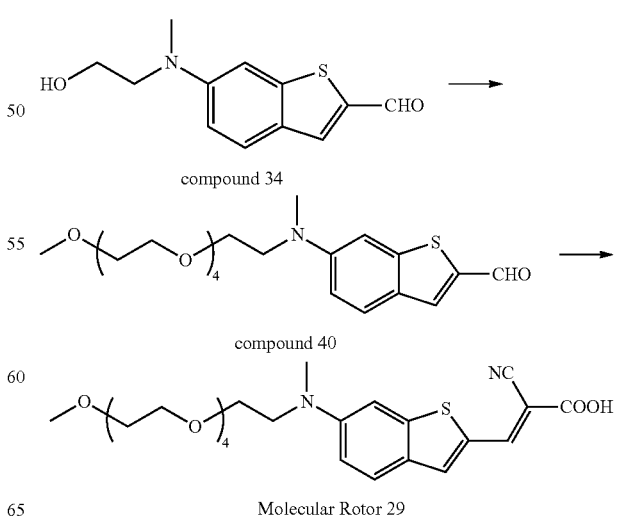

Synthesis of Compound 40

Compound 40 was synthesized by the method disclosed in the literature: K. T. Arun et. al. J. Phys. Chem. A. 2005, 109, 5571-5578. $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.52-3.65 (m, 20H), 3.37 (s, 3H), 2.97 (s, 3H).

Synthesis of Molecular Rotor 29

Synthesized according to the synthesis method of the Molecular Rotor 5, the Molecular Rotor 29 achieved a yield of 81%. $^1$H-NMR (400 MHz, CDCl$_3$): δ=7.81 (s, 1H), 7.68 (d, J=9.0 Hz, 1H), 7.05 (s, 1H), 6.92 (d, J=2.0 Hz, 1H), 6.82 (d, J=9.1, 2.3 Hz, 1H), 3.52-3.65 (m, 20H), 3.37 (s, 3H), 2.97 (s, 3H).

Example 30

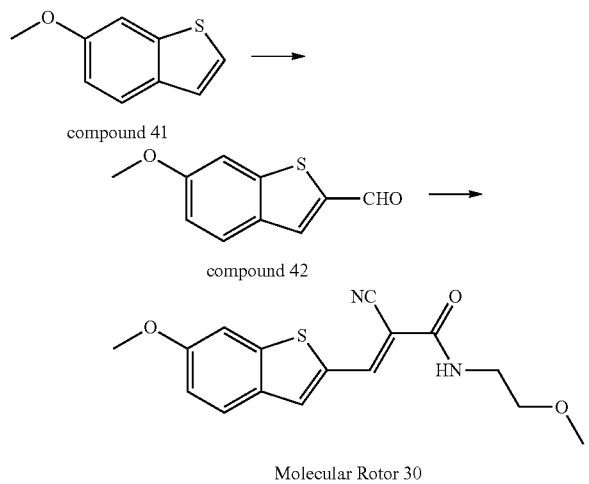

Synthesis of Compound 42

By referring to the synthesis method of Molecular Rotor 2, Compound 42 was synthesized and had a yield of 79%. $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.55 (s, 3H).

Synthesis of Molecular Rotor 30

Molecular Rotor 30 was synthesized according to the synthesis of Molecular Rotor 7, with a yield of 89%. $^1$H-NMR (400 MHz, CDCl$_3$): δ=7.81 (s, 1H), 7.68 (d, J=9.0 Hz, 1H), 6.92 (d, J=2.0 Hz, 1H), 6.82 (d, J=9.1, 2.3 Hz, 1H), 3.55 (s, 3H), 3.38 (s, 3H), 3.48-3.52 (m, 4H).

Example 31

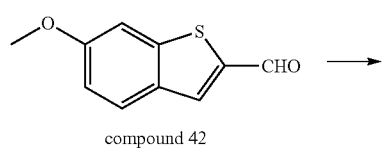

compound 42

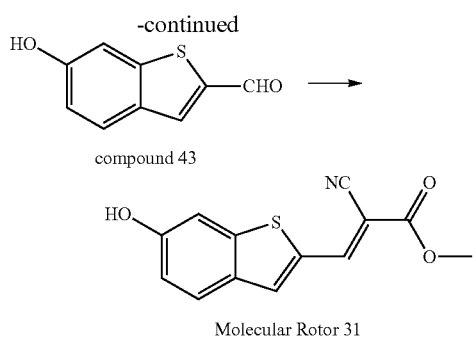

compound 43

Molecular Rotor 31

Synthesis of Compound 43

Compound 42 (0.38 g, 2 mmol) was dissolved in 25 ml of anhydrous dichloromethane. The system was cooled at −78° C., to which 2 ml of 1 M boron trichloride solution in diethyl ether was added, and then the system was stirred for 2 h and slowly warmed at room temperature. After the reaction was completed, the system was quenched with water. The system was poured into 100 ml of saturated brine and extracted three times with dichloromethane. The organic phases were combined, dried over anhydrous sodium sulfate, filtered to remove Na$_2$SO$_4$, and subjected to column chromatography after rotary evaporation to afford white crystals (0.34 g, 88%). $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H).

Synthesis of Molecular Rotor 31

Synthesized with reference to the synthesis of Molecular Rotor 1, the Molecular Rotor 31 had a yield of 91%. $^1$H-NMR (400 MHz, CDCl$_3$): δ=7.81 (s, 1H), 7.68 (d, J=9.0 Hz, 1H), 7.01 (s, 1H), 6.92 (d, J=2.0 Hz, 1H), 6.82 (d, J=9.1, 2.3 Hz, 1H), 3.61 (s, 3H), 3.55 (s, 3H).

Example 32

Synthesis of Molecular Rotor 32

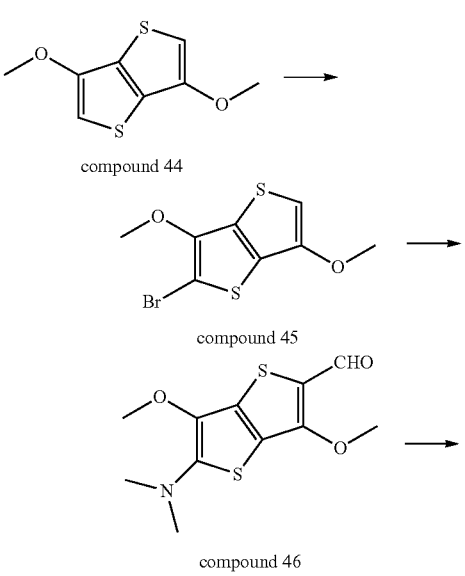

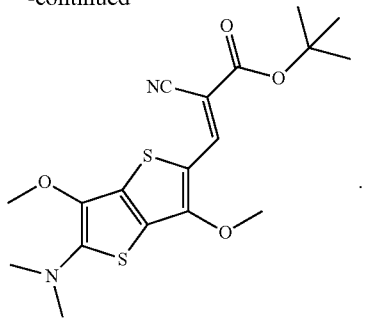

Molecular Rotor 32

Compound 45

Compound 44 (0.40 g, 2 mmol) was dissolved in 100 ml of dry methylene chloride. The mixture was cooled at −78° C., NBS (0.36 g, 2 mmol) was added in portions, and the mixture was stirred for 2 h under Ar. The mixture was then restored to room temperature. After stirring overnight, the reaction was completed. The system was quenched with water (10 ml) and filtered, and the organic phases were washed with saturated brine, combined, and dried over $Na_2SO_4$. The organic phases were dried by rotary evaporation and chromatographed to yield a pale yellow solid (0.45 g, 80%). $^1$H-NMR (400 MHz, $CDCl_3$): δ=6.57 (s, 1H), 4.28 (s, 3H), 3.93 (s, 3H).

Compound 46

Compound 46 was synthesized according to the synthesis of Compound 2, with a yield of 25%. $^1$H-NMR (400 MHz, $CDCl_3$): δ=10.0 (s, 1H), 6.54 (s, 1H), 4.28 (s, 3H), 3.87 (s, 3H), 3.12 (s, 6H).

Molecular Rotor 32

Molecular Rotor 32 was synthesized according to the synthesis of Molecular Rotor 1, with a yield of 86%. $^1$H-NMR (400 MHz, $CDCl_3$): δ=6.55 (s, 1H), 4.29 (s, 3H), 3.88 (s, 3H), 3.13 (s, 6H), 1.51 (s, 9H).

Example 33

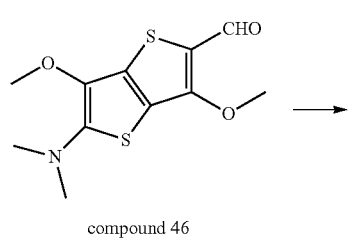

compound 46

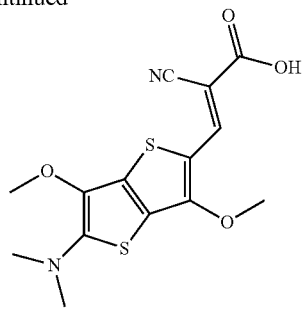

Molecular Rotor 33

Synthesis of Molecular Rotor 33

Compound 46 (0.27 g, 1 mmol) was placed in a 50 mL round bottom flask, to which cyanoacetic acid (0.102 g, 1.2 mmol) was added, followed by the addition of 30 mL of absolute ethanol to dissolve the mixture, and anhydrous zinc chloride at a catalytic amount. The system was heated to reflux in an oil bath under Ar atmosphere. After the reaction was completed and the system was cooled at room temperature, a portion of the solvent was evaporated to give an amount of solid, which was filtered. The filter cake was washed with ice ethanol and dried in vacuo to give a product (0.28 g, 92%). $^1$H-NMR (400 MHz, $CDCl_3$): δ=6.55 (s, 1H), 4.29 (s, 3H), 3.88 (s, 3H), 3.13 (s, 6H).

Example 34

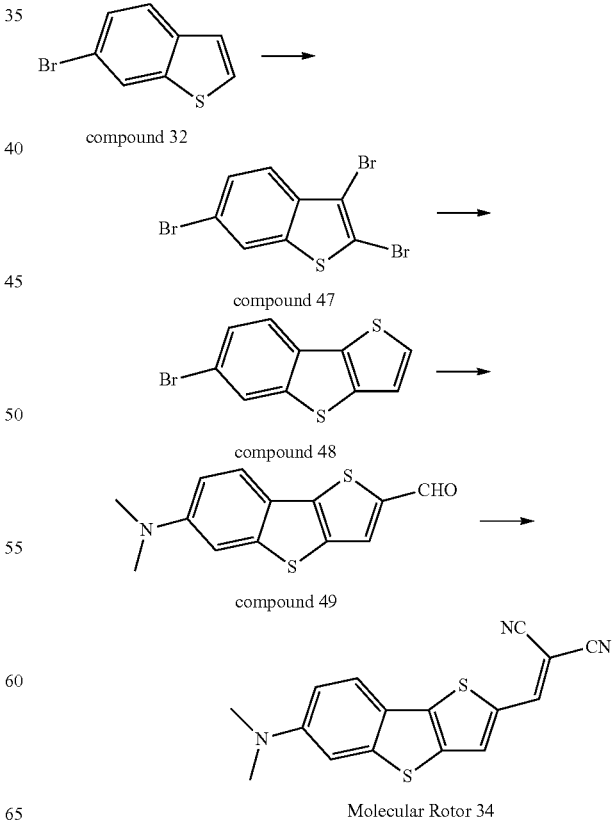

Synthesis of Compound 47

Compound 32 (0.43 g, 2 mmol) was dissolved in 50 ml of dry dihalomethane, in which potassium acetate (0.4 g, 4 mmol) was added, and bromine (0.32 g, 2 mmol) was added in an ice bath. The mixture was slowly warmed at room temperature. After the completion of the reaction, 100 ml of saturated sodium thiosulfate solution was added so that the organic phases were separated, and the aqueous phase was extracted three times with dichloromethane. The organic phases were combined, and then subjected to column chromatography after rotary evaporation to obtain a product (0.64 g, 81%). $^1$H-NMR (400 MHz, CDCl$_3$): δ=7.81 (s, 1H), 7.68 (d, J=9.0 Hz, 1H), 6.92 (d, J=2.0 Hz, 1H).

Synthesis of Compound 48

Compound 47 (1.27 g, 3.43 mmol) was dissolved in 50 ml of dry triethylamine, and Bis(triphenylphosphine)palladium Dichloride (120.2 mg, 0.171 mmol), cuprous iodide (65.2 mg, 0.343 mmol) and trimethylsilylacetylene (344 mg, 3.43 mmol) were added. The mixture was heated in an oil bath for 24 h under Ar atmosphere. After the reaction was completed, 5 ml of water was added to quench the reaction, and the solvent was dried by rotary evaporation. The residue was dissolved in diethyl ether, filtered and dried by rotary evaporation to give a crude product used directly in the next step without purification.

The crude product was dissolved in 30 ml of NMP, and then sodium sulfide nonahydrate (0.87 g, 3.63 mmol) was added. The mixture was heated in an oil bath at 190° C. for 12 h under Ar atmosphere, and cooled at room temperature. With the addition of 20 ml of a saturated ammonium chloride solution, the mixture was extracted thrice with methylene chloride. The organic phases were combined, dried over Na$_2$SO$_4$, filtered to remove Na$_2$SO$_4$, and chromatographed following rotary evaporation to yield a white solid (0.85 g, 49%). $^1$H-NMR (400 MHz, CDCl$_3$): δ=7.87 (m, 1H), 7.71 (m, 1H), 7.51 (d, J=5.4 Hz, 1H), 7.41 (m, 1H), 7.32 (d, J=5.4 Hz, 1H).

Synthesis of Compound 49

Compound 49 was synthesized according to the synthesis of Compound 2, with a yield of 44%. $^1$H-NMR (400 MHz, CDCl$_3$): δ=9.71 (s, 1H), 7.87 (m, 1H), 7.71 (m, 1H), 7.51 (d, J=5.4 Hz, 1H), 7.32 (d, J=5.4 Hz, 1H), 3.01 (s, 6H).

Synthesis of Molecular Rotor 34

Molecular Rotor 34 was synthesized according to the synthesis of Molecular Rotor 4, with a yield of 95%. $^1$H-NMR (400 MHz, CDCl$_3$): δ=7.87 (m, 1H), 7.71 (m, 1H), 7.51 (d, J=5.4 Hz, 1H), 7.32 (d, J=5.4 Hz, 1H), 7.01 (s, 1H).

Example 35

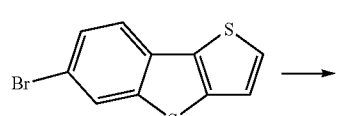

compound 22

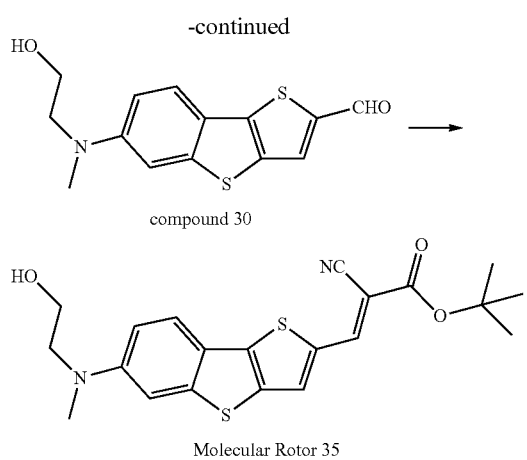

compound 30

Molecular Rotor 35

Synthesis of Compound 50

Compound 50 was synthesized according to the synthesis of Compound 4, with a yield of 78%. $^1$H-NMR (400 MHz, CDCl$_3$): δ=9.71 (s, 1H), 7.87 (m, 1H), 7.71 (m, 1H), 7.51 (d, J=5.4 Hz, 1H), 7.32 (d, J=5.4 Hz, 1H), 3.59 (t, 2H, J=5.60 Hz), 3.48 (t, 2H, J=5.60 Hz), 3.15 (s, 3H).

Synthesis of Molecular Rotor 35

Molecular Rotor 35 was synthesized according to the synthesis of Molecular Rotor 1, with a yield of 78%. $^1$H-NMR (400 MHz, CDCl$_3$): δ=7.87 (m, 1H), 7.71 (m, 1H), 7.51 (d, J=5.4 Hz, 1H), 7.32 (d, J=5.4 Hz, 1H), 7.01 (s, 1H), 3.59 (t, 2H, J=5.60 Hz), 3.48 (t, 2H, J=5.60 Hz), 3.15 (s, 3H), 1.49 (s, 9H).

Example 36

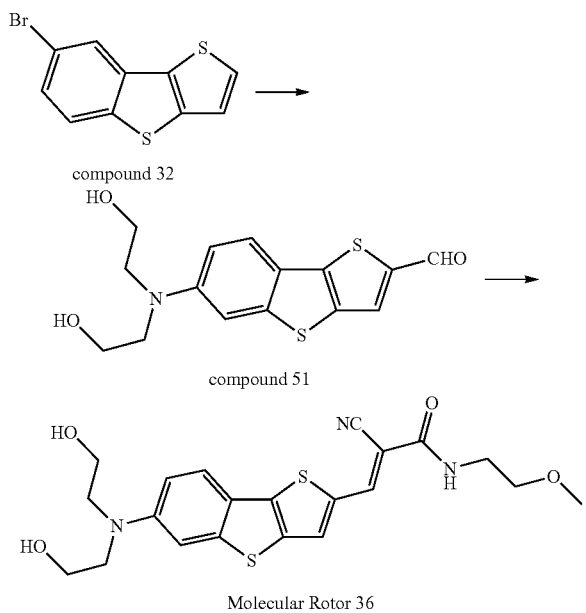

compound 32 compound 51

Molecular Rotor 36

Synthesis of Compound 51

Compound 51 was synthesized according to the synthesis of Compound 2, with a yield of 51%. ¹H-NMR (400 MHz, CDCl₃): δ=9.71 (s, 1H), 7.87 (m, 1H), 7.71 (m, 1H), 7.51 (d, J=5.4 Hz, 1H), 7.32 (d, J=5.4 Hz, 1H), 3.55 (t, 4H, J=5.60 Hz), 3.46 (t, 4H, J=5.60 Hz).

Synthesis of Molecular Rotor 36

Molecular Rotor 36 was synthesized according to the synthesis of Molecular Rotor 7, with a yield of 89%. ¹H-NMR (400 MHz, CDCl₃): δ=7.87 (m, 1H), 7.71 (m, 1H), 7.51 (d, J=5.4 Hz, 1H), 7.32 (d, J=5.4 Hz, 1H), 7.03 (s, 1H), 3.55 (t, 4H, J=5.60 Hz), 3.46-3.52 (m, 4H), 3.46 (t, 4H, J=5.60 Hz), 3.38 (s, 3H).

Example 37

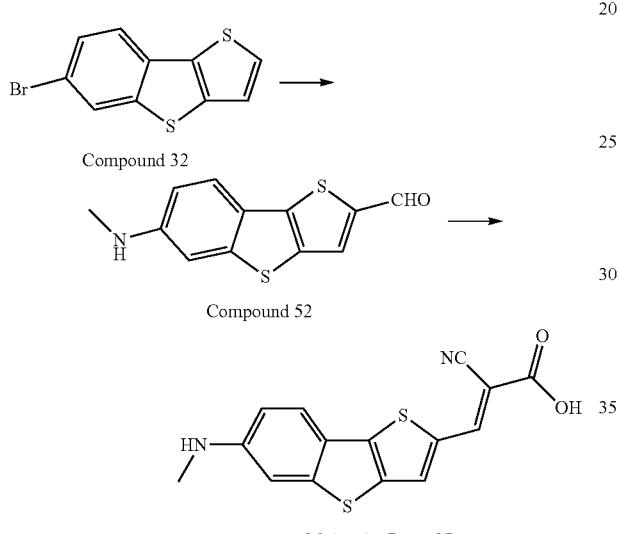

Synthesis of Compound 52

Compound 52 was synthesized according to the synthesis of Compound 2, with a yield of 21%. ¹H-NMR (400 MHz, CDCl₃): δ=9.71 (s, 1H), 7.87 (m, 1H), 7.71 (m, 1H), 7.51 (d, J=5.4 Hz, 1H), 7.32 (d, J=5.4 Hz, 1H), 3.18 (s, 3H).

Synthesis of Molecular Rotor 37

Molecular Rotor 37 was synthesized according to the synthesis of Molecular Rotor 5, with a yield of 93%. ¹H-NMR (400 MHz, CDCl₃): δ=7.87 (m, 1H), 7.71 (m, 1H), 7.51 (d, J=5.4 Hz, 1H), 7.32 (d, J=5.4 Hz, 1H), 7.03 (s, 1H) 3.18 (s, 3H).

Example 38

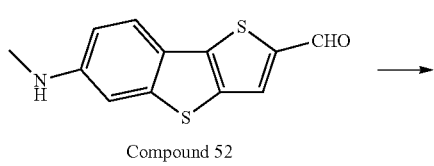

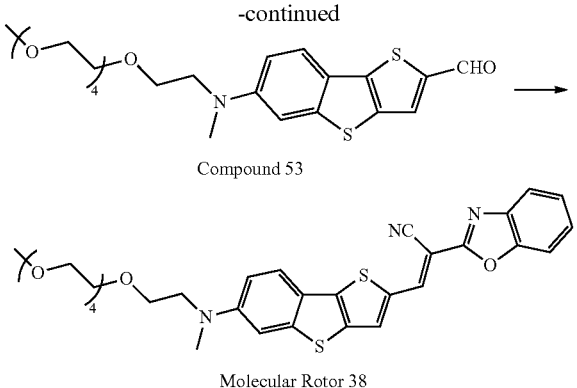

Synthesis of Compound 53

Compound 53 was synthesized according to the synthesis of Compound 8, with a yield of 75%. ¹H-NMR (400 MHz, CDCl₃): δ=9.71 (s, 1H), 7.87 (m, 1H), 7.71 (m, 1H), 7.51 (d, J=5.4 Hz, 1H), 7.32 (d, J=5.4 Hz, 1H), 3.52-3.65 (m, 20H), 3.37 (s, 3H), 2.97 (s, 3H).

Synthesis of Molecular Rotor 38

Synthesized according to the synthesis of Molecule Rotor 2, Molecular Rotor 38 had a yield of 91%. ¹H-NMR (400 MHz, DMSO-d₆): δ=8.49 (s, 1H), 8.07 (s, 1H), 7.68-7.71 (m, 2H), 7.35-7.38 (m, 2H), 6.46 (s, 1H), 3.52-3.65 (m, 20H), 3.37 (s, 3H), 2.97 (s, 3H).

Example 39

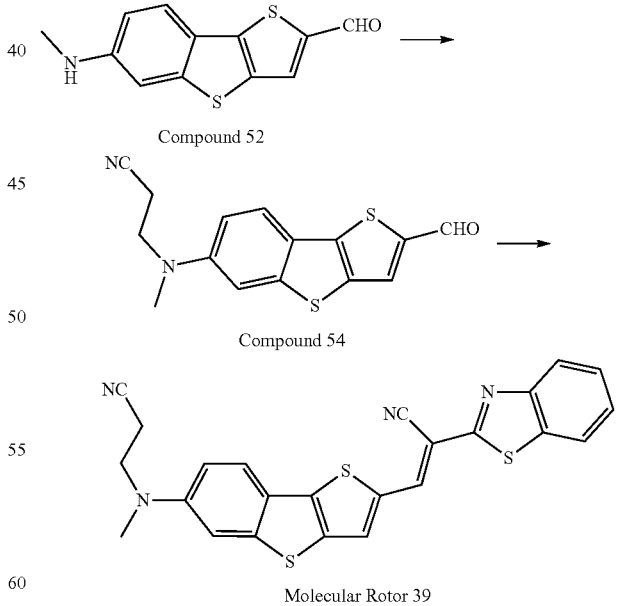

Synthesis of Compound 54

Compound 54 was synthesized according to the synthesis of Compound 10, with a yield of 86%. ¹H-NMR (400 MHz, CDCl₃): δ=9.71 (s, 1H), 7.87 (m, 1H), 7.71 (m, 1H), 7.51 (d, J=5.4 Hz, 1H), 7.32 (d, J=5.4 Hz, 1H), 3.72 (t, J=6.9 Hz, 2H), 3.03 (s, 3H), 2.57 (t, J=6.9 Hz, 2H).

Synthesis of Molecular Rotor 39

Molecular Rotor 39 was synthesized according to the synthesis of Molecular Rotor 3, with a yield of 86%. ¹H-NMR (400 MHz, DMSO-d₆): δ=7.87 (m, 1H), 7.75 (m, 1H), 7.68-7.71 (m, 2H), 7.51 (d, J=5.4 Hz, 1H), 7.35-7.38 (m, 2H), 7.32 (d, J=5.4 Hz, 1H), 6.96 (s, 1H), 3.72 (t, J=6.9 Hz, 2H), 3.03 (s, 3H), 2.57 (t, J=6.9 Hz, 2H).

Example 40

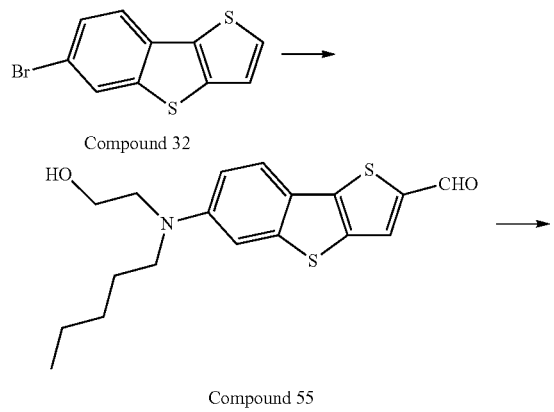

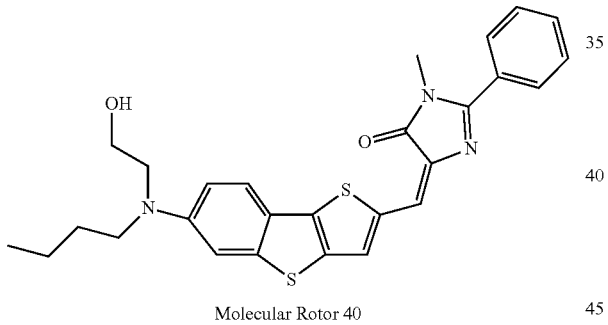

Synthesis of Compound 55

Please refer to the synthesis of Compound 39: ¹H-NMR (400 MHz, CDCl₃): δ=9.77 (s, 1H), 7.87 (m, 1H), 7.71 (m, 1H), 7.51 (d, J=5.4 Hz, 1H), 7.32 (d, J=5.4 Hz, 1H), 3.63 (t, J=8.0 Hz, 2H), 3.37 (t, J=8.0 Hz, 2H), 3.00 (s, 3H), 2.21 (s, 3H), 1.86 (s, 6H), 1.67 (m, 2H), 1.42 (m, 2H), 1.02 (t, J=5.0 Hz, 3H).

Synthesis of Molecular Rotor 40

Molecular Rotor 40 was synthesized according to the synthesis of Molecular Rotor 8, with a yield of 88%. ¹H-NMR (400 MHz, CDCl₃): δ=7.87 (m, 1H), 7.71 (m, 1H), 7.63-7.48 (m, 6H), 7.32 (d, J=5.4 Hz, 1H), 7.03 (s, 1H), 3.63 (t, J=8.0 Hz, 2H), 3.37 (t, J=8.0 Hz, 2H), 3.13 (s, 3H), 3.00 (s, 3H), 2.21 (s, 3H), 1.86 (s, 6H), 1.67 (m, 2H), 1.42 (m, 2H), 1.02 (t, J=5.0 Hz, 3H).

Example 41

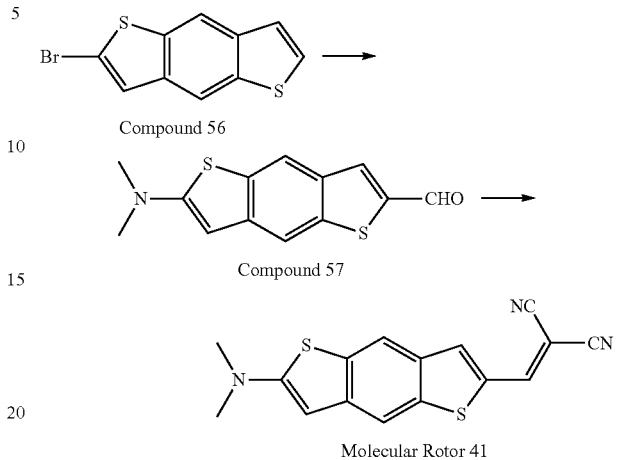

Synthesis of Compound 56

Please refer to the method disclosed in the literature: WO2013142841(A1), 2013 Sep. 26. ¹H-NMR (400 MHz, CDCl₃): δ=7.87 (s, 2H), 7.54 (s, 1H), 7.42 (d, J=5.6 Hz, 1H), 7.39 (d, J=5.6 Hz, 1H).

Synthesis of Compound 57

Compound 57 was synthesized according to the synthesis of Compound 2, with a yield of 41%. ¹H-NMR (400 MHz, CDCl₃): δ=9.99 (s, 1H), 7.89 (s, 2H), 7.59 (s, 1H), 7.27 (s, 1H), 3.09 (s, 6H).

Synthesis of Molecular Rotor 41

Molecular Rotor 41 was synthesized according to the synthesis of Molecular Rotor 4, with a yield of 81%. ¹H-NMR (400 MHz, CDCl₃): δ=7.89 (s, 2H), 7.59 (s, 1H), 7.27 (s, 1H), 7.02 (s, 1H), 3.09 (s, 6H).

Example 42

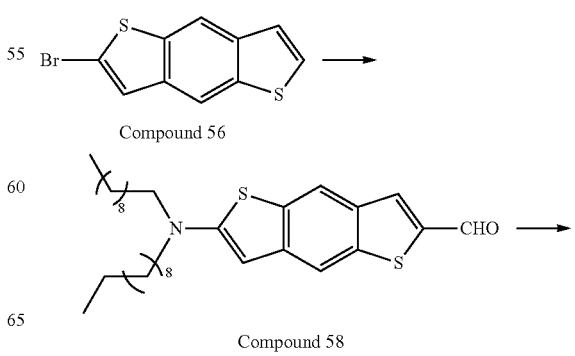

-continued

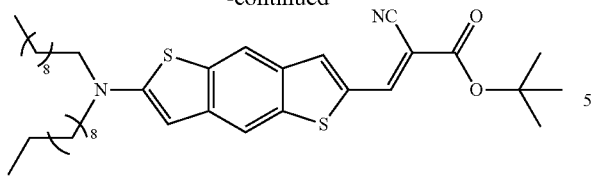

Molecular Rotor 42

Synthesis of Compound 58

Compound 58 was synthesized according to the synthesis of Compound 3, with a yield of 55%. $^1$H-NMR (400 MHz, CDCl$_3$): δ=9.99 (s, 1H), 7.89 (s, 2H), 7.59 (s, 1H), 7.27 (s, 1H), 3.32 (t, 4H, J=8.20 Hz), 1.64 (m, 32H), 0.93 (t, 6H, J=8.00 Hz).

Synthesis of Molecular Rotor 42

Molecular Rotor 24 was synthesized according to the synthesis of Compound 1, with a yield of 96%. $^1$H-NMR (400 MHz, CDCl$_3$): δ=7.89 (s, 2H), 7.59 (s, 1H), 7.27 (s, 1H), 7.05 (s, 1H), 3.32 (t, 4H, J=8.20 Hz), 1.64 (m, 32H), 1.49 (s, 9H), 0.93 (t, 6H, J=8.00 Hz).

Example 43

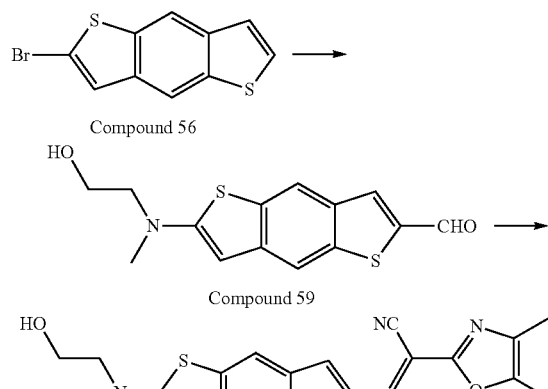

Molecular Rotor 43

Synthesis of Compound 59

Compound 59 was synthesized according to the synthesis of Compound 4, with a yield of 65%. $^1$H-NMR (400 MHz, CDCl$_3$): δ=9.99 (s, 1H), 7.89 (s, 2H), 7.59 (s, 1H), 7.27 (s, 1H), 3.59 (t, 2H, J=5.60 Hz), 3.48 (t, 2H, J=5.60 Hz), 3.15 (s, 3H).

Synthesis of Molecular Rotor 43

Molecular Rotor 43 was synthesized according to the synthesis of Molecular Rotor 2, with a yield of 88%. $^1$H-NMR (400 MHz, CDCl$_3$): δ=7.89 (s, 2H), 7.74 (d, 1H, J=4.0 Hz), 7.59 (s, 1H), 7.55 (d, 1H, J=4.0 Hz), 7.36-7.42 (m, 2H), 7.27 (s, 1H), 7.00 (s, 1H), 3.59 (t, 2H, J=5.60 Hz), 3.48 (t, 2H, J=5.60 Hz), 3.15 (s, 3H).

Example 44

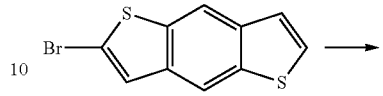

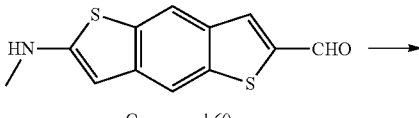

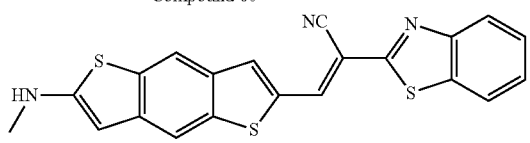

Molecular Rotor 44

Synthesis of Compound 60

Compound 60 was synthesized according to the synthesis of Compound 6, with a yield of 55%. $^1$H-NMR (400 MHz, CDCl$_3$): δ=10.00 (s, 1H), 7.88 (s, 2H), 7.60 (s, 1H), 7.28 (s, 1H), 3.11 (s, 3H).

Synthesis of Molecular Rotor 44

Molecular Rotor 44 was synthesized according to the synthesis of Molecular Rotor 3, with a yield of 81%. $^1$H-NMR (400 MHz, CDCl$_3$): δ=8.04 (d, 1H, J=8.0 Hz), 7.91 (d, 1H, J=8.0 Hz), 7.88 (s, 2H), 7.60 (s, 1H), 7.53 (t, 1H, J=8.0 Hz), 7.45 (t, 1H, J=8.0 Hz), 7.28 (s, 1H), 7.01 (s, 1H), 3.11 (s, 3H).

Example 45

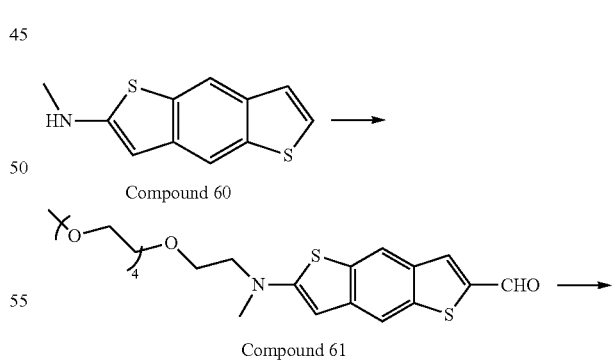

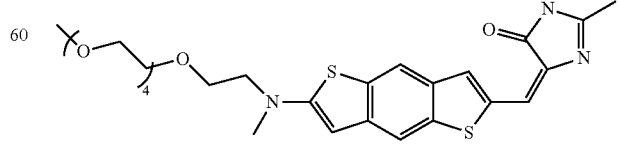

Molecular Rotor 45

Synthesis of Compound 61

Compound 61 was synthesized according to the synthesis of Compound 8, with a yield of 76%. $^1$H-NMR (400 MHz, CDCl$_3$): δ=10.00 (s, 1H), 7.88 (s, 2H), 7.60 (s, 1H), 7.28 (s, 1H), 3.52-3.65 (m, 20H), 3.37 (s, 3H), 2.97 (s, 3H).

Synthesis of Molecular Rotor 45

Molecular Rotor 45 was synthesized according to the synthesis of Molecular Rotor 6, with a yield of 85%. $^1$H-NMR (400 MHz, CDCl$_3$): δ=7.87 (s, 2H), 7.61 (s, 1H), 7.28 (s, 1H), 7.02 (s, 1H), 3.98 (s, 3H), 3.52-3.65 (m, 20H), 3.37 (s, 3H), 3.01 (s, 3H), 2.97 (s, 3H).

Example 46

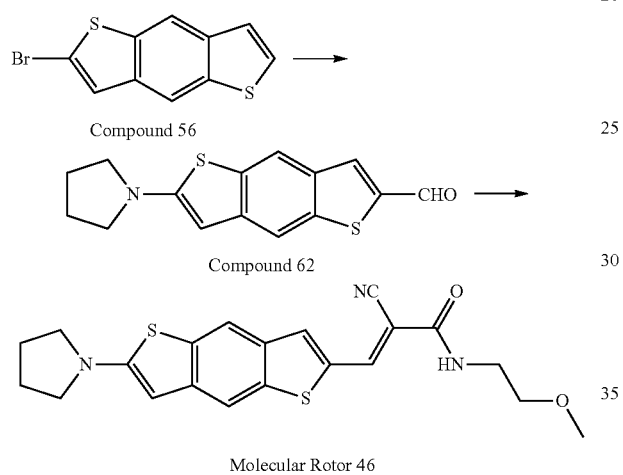

Synthesis of Compound 62

Compound 62 was synthesized according to the synthesis of Compound 24, with a yield of 66%. $^1$H-NMR (400 MHz, CDCl$_3$): δ=10.01 (s, 1H), 7.86 (s, 2H), 7.61 (s, 1H), 7.27 (s, 1H), 3.41 (t, 4H, J=5.5 Hz), 2.21 (t, 4H, J=5.5 Hz).

Synthesis of Molecular Rotor 46

Molecular Rotor 46 was synthesized according to the synthesis of Molecular Rotor 7, with a yield of 85%. $^1$H-NMR (400 MHz, CDCl$_3$): δ=7.86 (s, 2H), 7.61 (s, 1H), 7.27 (s, 1H), 7.03 (s, 1H), 3.48-3.52 (m, 4H), 3.41 (t, 4H, J=5.5 Hz), 3.38 (s, 3H), 2.21 (t, 4H, J=5.5 Hz).

Example 47

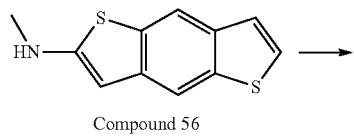

Compound 56

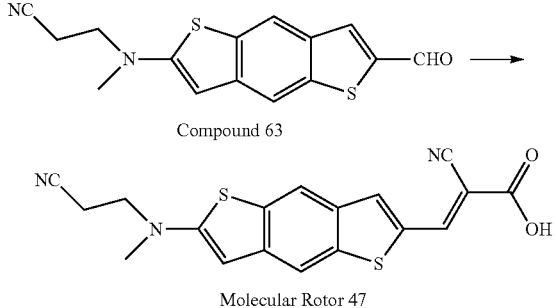

Synthesis of Compound 63

Compound 63 was synthesized according to the synthesis of Compound 10, with a yield of 76%. $^1$H-NMR (400 MHz, CDCl$_3$): δ=10.02 (s, 1H), 7.86 (s, 2H), 7.61 (s, 1H), 7.27 (s, 1H), 3.72 (t, 2H, J=8.0 Hz), 3.11 (s, 3H), 2.57 (t, 2H, J=8.0 Hz).

Synthesis of Molecular Rotor 47

Molecular Rotor 47 was synthesized according to the synthesis of Molecular Rotor 5, with a yield of 91%. $^1$H-NMR (400 MHz, CDCl$_3$): δ=7.88 (s, 2H), 7.60 (s, 1H), 7.28 (s, 1H), 6.99 (s, 1H), 3.72 (t, 2H, J=8.0 Hz), 3.11 (s, 3H), 2.57 (t, 2H, J=8.0 Hz).

Example 48

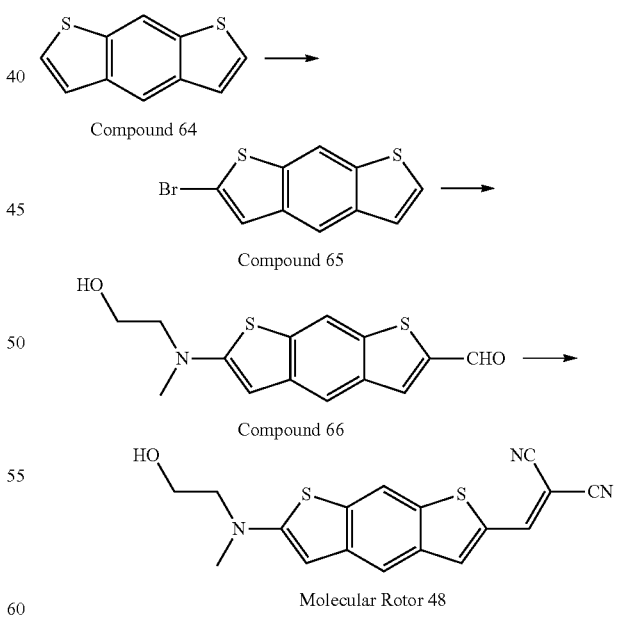

Synthesis of Compound 64

Compound 64 was synthesized according to the method disclosed in the literature (Riger Ralph et al. Chem. Mater.

2000, 22, 5314-4318). $^1$H-NMR (400 MHz, CDCl$_3$): δ=8.38 (s, 1H), 8.28 (s, 1H), 7.47 (d, 2H, J=5.6 Hz), 7.42 (d, 2H, J=5.6 Hz).

Synthesis of Compound 65

Compound 65 was synthesized according to the synthesis of Compound 1, with a yield of 55%. $^1$H-NMR (400 MHz, CDCl$_3$): δ=8.38 (s, 1H), 8.21 (s, 1H), 7.41 (m, 1H), 7.38 (d, 1H, J=5.6 Hz).

The Synthesis of Compound 66

Compound 66 was synthesized according to the synthesis of Compound 4, with a yield of 55%. $^1$H-NMR (400 MHz, CDCl$_3$): δ=9.99 (s, 1H), 8.39 (s, 1H), 8.22 (s, 1H), 7.42 (m, 1H), 7.38 (d, 1H, J=5.6 Hz), 3.59 (t, 2H, J=5.60 Hz), 3.48 (t, 2H, J=5.60 Hz), 3.15 (s, 3H).

Synthesis of Molecular Rotor 48

Molecular Rotor 48 was synthesized according to the synthesis of Molecular Rotor 4, with a yield of 95%. $^1$H-NMR (400 MHz, CDCl$_3$): δ=8.38 (s, 1H), 8.23 (s, 1H), 7.42 (m, 1H), 7.38 (d, 1H, J=5.6 Hz), 7.05 (s, 1H), 3.59 (t, 2H, J=5.60 Hz), 3.48 (t, 2H, J=5.60 Hz), 3.15 (s, 3H).

Example 49

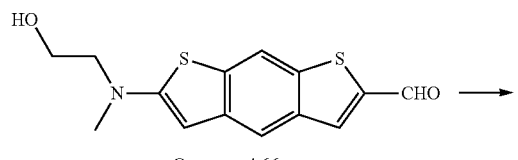

Compound 66

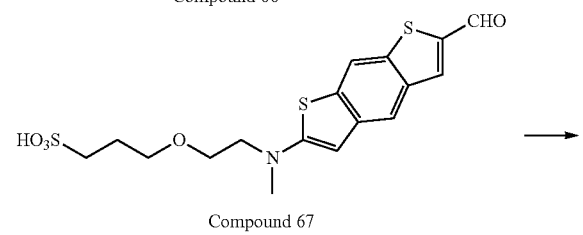

Compound 67

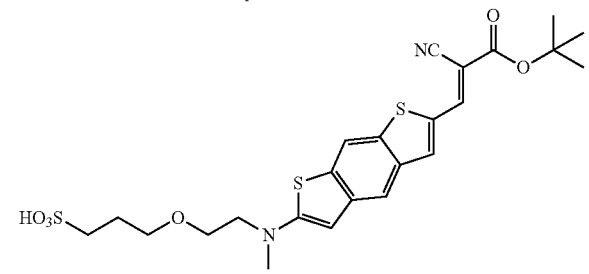

Molecular Rotor 49

Synthesis of Compound 67

Compound 67 was synthesized according to the synthesis of Compound 5, with a yield of 76%. $^1$H-NMR (400 MHz, CDCl$_3$): δ=9.99 (s, 1H), 8.39 (s, 1H), 8.22 (s, 1H), 7.42 (m, 1H), 7.38 (d, 1H, J=5.6 Hz), 3.68 (m, 4H), 3.55 (m, 2H), 3.35 (m, 2H), 3.11 (s, 3H), 2.42 (m, 2H).

Synthesis of Molecular Rotor 49

Molecular Rotor 49 was synthesized according to the synthesis of Molecular Rotor 1, with a yield of 90%. $^1$H-NMR (400 MHz, CDCl$_3$): δ=8.36 (s, 1H), 8.23 (s, 1H), 7.42 (m, 1H), 7.38 (d, 1H, J=5.6 Hz), 7.02 (s, 1H), 3.68 (m, 4H), 3.55 (m, 2H), 3.35 (m, 2H), 3.11 (s, 3H), 2.42 (m, 2H).

Example 50

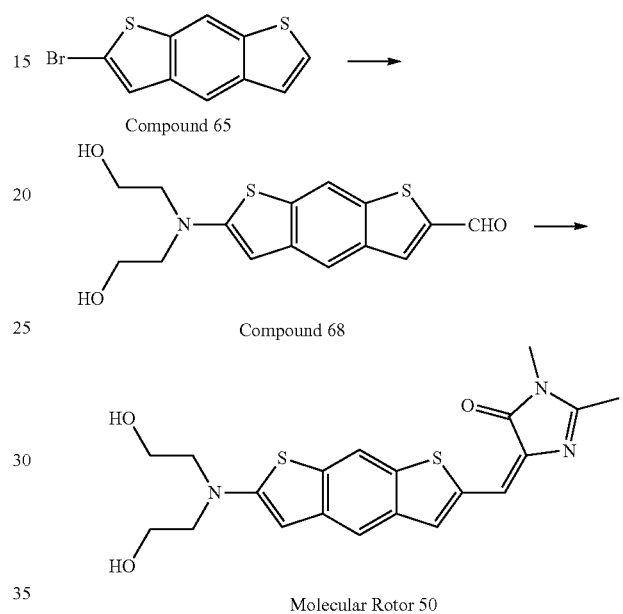

Synthesis of Compound 68

Compound 68 was synthesized according to the synthesis of Compound 29, with a yield of 58%. $^1$H-NMR (400 MHz, CDCl$_3$): δ=10.01 (s, 1H), 8.39 (s, 1H), 8.22 (s, 1H), 7.42 (m, 1H), 7.38 (d, 1H, J=5.6 Hz), 3.59 (t, 4H, J=5.60 Hz), 3.48 (t, 4H, J=5.60 Hz).

Synthesis of Molecular Rotor 50

Molecular Rotor 50 was synthesized according to the synthesis of Molecular Rotor 6, with a yield of 87%. $^1$H-NMR (400 MHz, CDCl$_3$): δ=8.38 (s, 1H), 8.20 (s, 1H), 7.41 (m, 1H), 7.37 (d, 1H, J=5.6 Hz), 7.00 (s, 1H), 3.59 (t, 4H, J=5.60 Hz), 3.48 (t, 4H, J=5.60 Hz), 3.0 (s, 3H), 2.15 (s, 3H).

Example 51

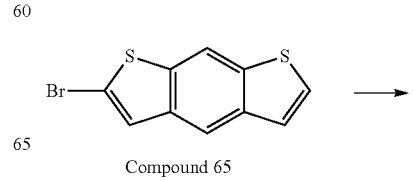

Compound 65

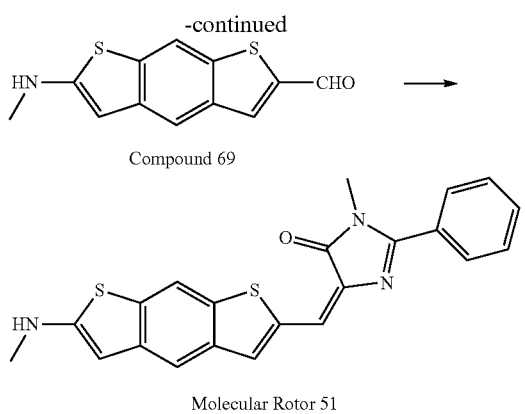

Synthesis of Compound 69

Compound 69 was synthesized according to the synthesis of Compound 6, with a yield of 54%. $^1$H-NMR (400 MHz, CDCl$_3$): δ=10.00 (s, 1H), 8.38 (s, 1H), 8.23 (s, 1H), 7.63-7.48 (m, 5H), 7.42 (m, 1H), 7.38 (d, 1H, J=5.6 Hz), 7.00 (s, 1H), 3.18 (s, 3H), 3.07 (s, 3H).

Synthesis of Molecular Rotor 51

Molecular Rotor 51 was synthesized according to the synthesis of Molecular Rotor 54, with a yield of 89%. $^1$H-NMR (400 MHz, CDCl$_3$): δ=8.38 (s, 1H), 8.23 (s, 1H), 7.42 (m, 2H), 7.38 (d, 1H, J=5.6 Hz), 3.18.

Example 52

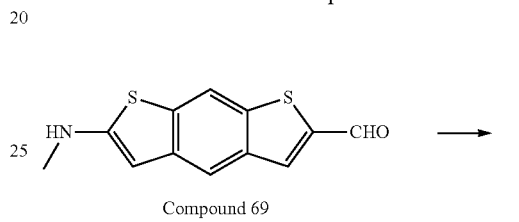

Synthesis of Compound 70

Compound 70 was synthesized according to the synthesis of Compound 8, with a yield of 66%. $^1$H-NMR (400 MHz, CDCl$_3$): δ=10.00 (s, 1H), 8.38 (s, 1H), 8.23 (s, 1H), 7.42 (m, 1H), 7.38 (d, 1H, J=5.6 Hz), 3.52-3.65 (m, 20H), 3.37 (s, 3H), 2.97 (s, 3H).

Synthesis of Molecular Rotor 52

Molecular Rotor 52 was synthesized according to the synthesis of Molecular Rotor 2, with a yield of 86%. $^1$H-NMR (400 MHz, CDCl$_3$): δ=8.38 (s, 1H), 8.23 (s, 1H), 7.74 (d, 1H, J=4.0 Hz), 7.55 (d, 1H, J=4.0 Hz), 7.38-7.42 (m, 3H), 7.38 (d, 1H, J=5.6 Hz), 6.95 (s, 1H), 3.52-3.65 (m, 20H), 3.37 (s, 3H), 2.97 (s, 3H).

Example 53

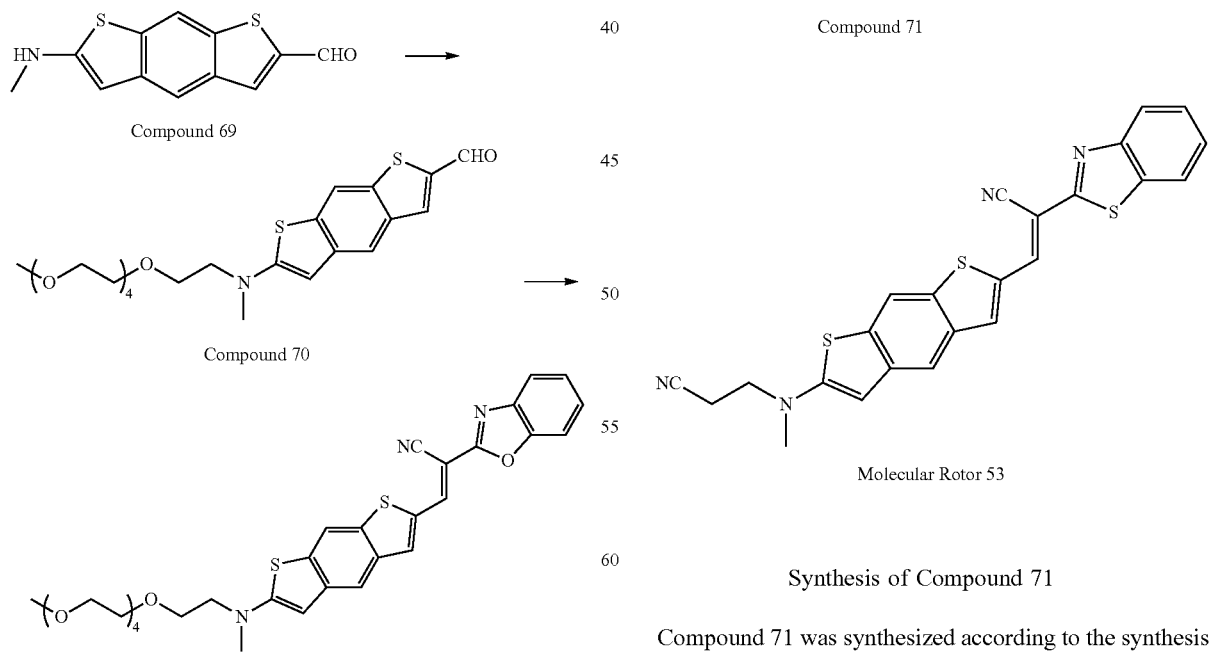

Synthesis of Compound 71

Compound 71 was synthesized according to the synthesis of Compound 10, with a yield of 69%. $^1$H-NMR (400 MHz, CDCl$_3$): δ6=10.01 (s, 1H), 8.39 (s, 1H), 8.21 (s, 1H), 7.41 (m, 1H), 7.37 (d, 1H, J=5.6 Hz), 3.72 (t, 2H, J=6.9 Hz), 3.03 (s, 3H), 2.57 (t, 3H, J=6.9 Hz).

Example 54

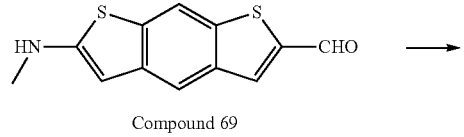

Compound 69

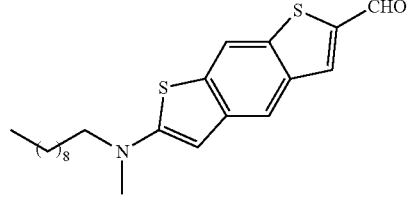

Compound 72

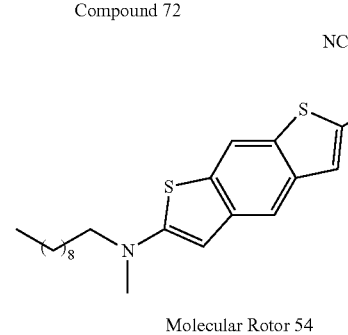

Molecular Rotor 54

Synthesis of Compound 72

Compound 72 was synthesized according to the synthesis of Compound 12, with a yield of 61%. $^1$H-NMR (400 MHz, CDCl$_3$): δ=10.01 (s, 1H), 8.39 (s, 1H), 8.21 (s, 1H), 7.41 (m, 1H), 7.37 (d, 1H, J=5.6 Hz), 3.09-3.12 (m, 5H), 1.59-1.66 (m, 2H), 1.27-1.41 (m, 14H), 0.89 (t, 3H, J=7.0 Hz).

Synthesis of Molecular Rotor 54

Molecular Rotor 54 was synthesized according to the synthesis of Molecular Rotor 5, with a yield of 86%. $^1$H-NMR (400 MHz, CDCl$_3$): δ=8.38 (s, 1H), 8.22 (s, 1H), 7.42 (m, 1H), 7.38 (d, 1H, J=5.6 Hz), 7.01 (s, 1H), 3.09-3.12 (m, 5H), 1.59-1.66 (m, 2H), 1.27-1.41 (m, 14H), 0.89 (t, 3H, J=7.0 Hz).

Example 55

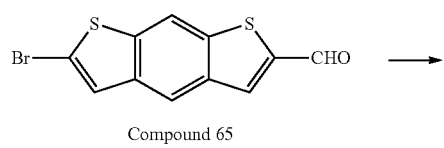

Compound 65

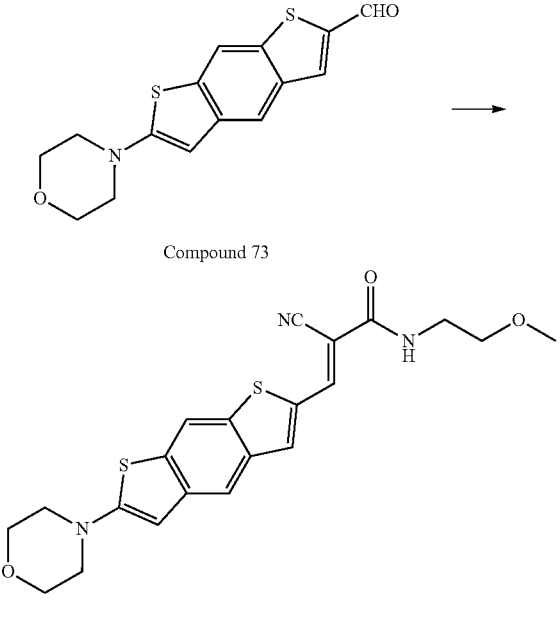

Compound 73

Molecular Rotor 55

Synthesis of Compound 73

Compound 73 was synthesized according to the synthesis of Compound 21, with a yield of 69%. $^1$H-NMR (400 MHz, CDCl$_3$): δ=10.01 (s, 1H), 8.39 (s, 1H), 8.21 (s, 1H), 7.41 (m, 1H), 7.37 (d, 1H, J=5.6 Hz), 3.94-3.76 (m, 4H), 3.42-3.26 (m, 4H).

Synthesis of Molecular Rotor 55

Molecular Rotor 55 was synthesized according to the synthesis of Molecular Rotor 7, with a yield of 93%. $^1$H-NMR (400 MHz, CDCl$_3$): δ=8.39 (s, 1H), 8.21 (s, 1H), 7.41 (m, 1H), 7.37 (d, 1H, J=5.6 Hz), 6.99 (s, 1H), 3.94-3.76 (m, 4H), 3.49-3.52 (m, 2H), 3.42-3.26 (m, 4H), 3.39 (s, 3H).

Example 56

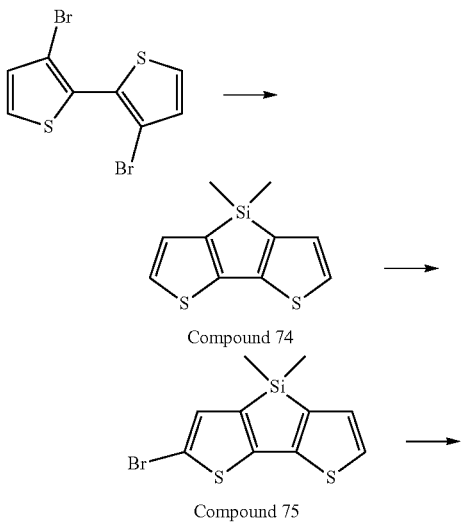

Compound 74

Compound 75

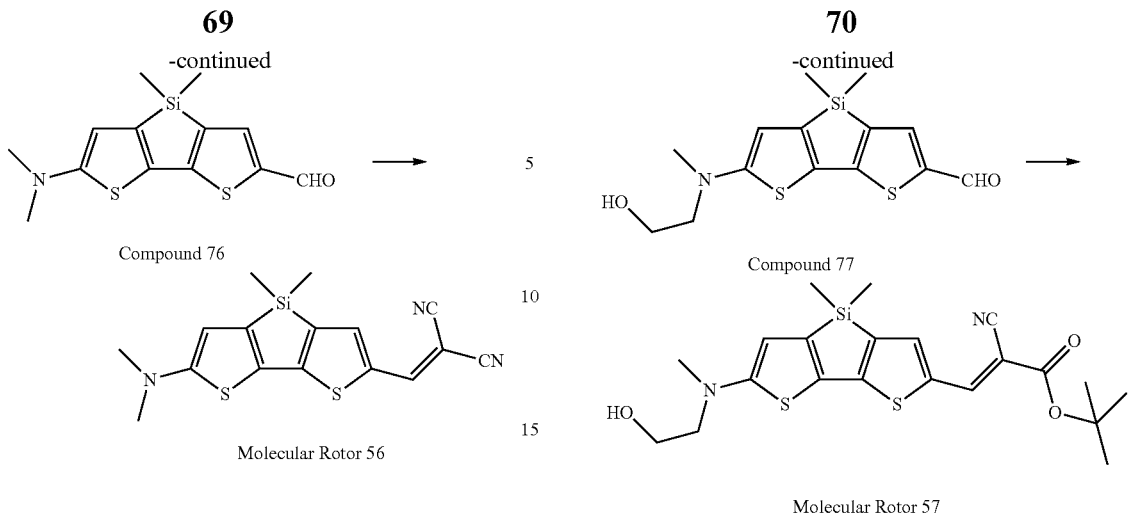

Compound 76

Molecular Rotor 56

Synthesis of Compound 74

The synthesis was carried out according to the method disclosed in the literature: Kureya, Takeshi et al. Jpn. Kokai Tokkyo Koho, 2013194039.30 Sep. 2013. $^1$H-NMR (400 MHz, CDCl$_3$): δ=7.24 (d, 2H, J=5.0 Hz), 7.19 (d, 2H, J=5.0 Hz), 0.46 (s, 6H).

Synthesis of Compound 75

Compound 74 (0.4 g, 1.8 mmol) was dissolved in 100 ml of anhydrous tetrahydrofuran, and the system was cooled at −30° C. After the addition of N-bromodibutylimide, the system was stirred under Ar atmosphere for 2 h, followed by adding 5 ml of water to quench the reaction, and the resultant was allowed to return to room temperature and dried by rotary evaporation to remove the solvent. The residue was dissolved in 100 ml of dichloromethane, and washed thrice with water, wherein the organic phases were dried over Na$_2$SO$_4$, filtered to remove Na$_2$SO$_4$, and subjected to column chromatography after rotary evaporation to obtain a white solid (0.31 g, 57%). $^1$H-NMR (400 MHz, CDCl$_3$): δ=7.73 (s, 1H), 7.42 (d, 1H, J=4.8 Hz), 7.15 (d, 1H, J=4.8 Hz), 0.46 (s, 6H).

Synthesis of Compound 76

Compound 76 was synthesized according to the synthesis of Compound 2, with a yield of 51%. $^1$H-NMR (400 MHz, CDCl$_3$): δ=9.87 (s, 1H), 7.83 (s, 1H), 7.10 (s, 1H), 3.1 (s, 6H), 0.46 (s, 6H).

Synthesis of Molecular Rotor 56

Molecular Rotor 56 was synthesized according to the synthesis of Molecular Rotor 4, with a yield of 95%.
$^1$H-NMR (400 MHz, CDCl$_3$): δ=7.83 (s, 1H), 7.10 (s, 1H), 7.01 (s, 1H), 3.1 (s, 6H), 0.46 (s, 6H).

Example 57

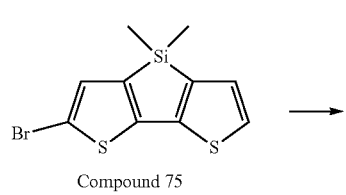

Compound 75

Compound 77

Molecular Rotor 57

Synthesis of Compound 77

Compound 77 was synthesized according to the synthesis method of Compound 4 in a yield of 42%. $^1$H-NMR (400 MHz, CDCl$_3$): δ=9.88 (s, 1H), 7.83 (s, 1H), 7.10 (s, 1H), 3.59 (t, 2H, J=5.60 Hz), 3.48 (t, 2H, J=5.60 Hz), 3.15 (s, 3H), 0.46 (s, 6H).

Synthesis of Molecular Rotor 57

Molecular Rotor 57 was synthesized according to the synthesis of Molecular Rotor 1, with a yield of 96%. $^1$H-NMR (400 MHz, CDCl$_3$): δ=7.84 (s, 1H), 7.11 (s, 1H), 7.03 (s, 1H), 3.59 (t, 2H, J=5.60 Hz), 3.48 (t, 2H, J=5.60 Hz), 3.15 (s, 3H), 1.50 (s, 9H), 0.46 (s, 6H).

Example 58

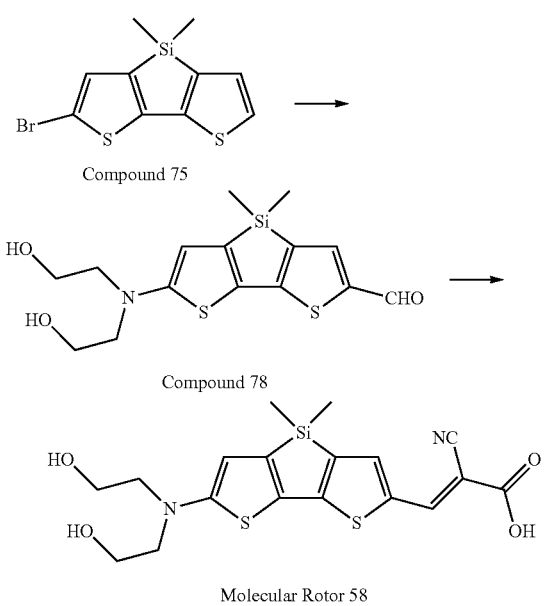

Compound 75

Compound 78

Molecular Rotor 58

Synthesis of Compound 78

The synthesis was carried out according to the synthesis of Compound 35, in yield of 43%. $^1$H-NMR (400 MHz, CDCl$_3$): δ=9.89 (s, 1H), 7.83 (s, 1H), 7.10 (s, 1H), 3.63 (t, J=8.0 Hz, 4H), 3.37 (t, J=8.0 Hz, 4H), 0.46 (s, 6H).

Synthesis of Molecular Rotor 58

Molecular Rotor 58 was synthesized according to the synthesis of Molecular Rotor 5, with a yield of 97%. $^1$H-NMR (400 MHz, CDCl$_3$): δ=7.83 (s, 1H), 7.10 (s, 1H), 6.99 (s, 1H), 3.63 (t, J=8.0 Hz, 4H), 3.37 (t, J=8.0 Hz, 4H), 0.46 (s, 6H).

Example 59

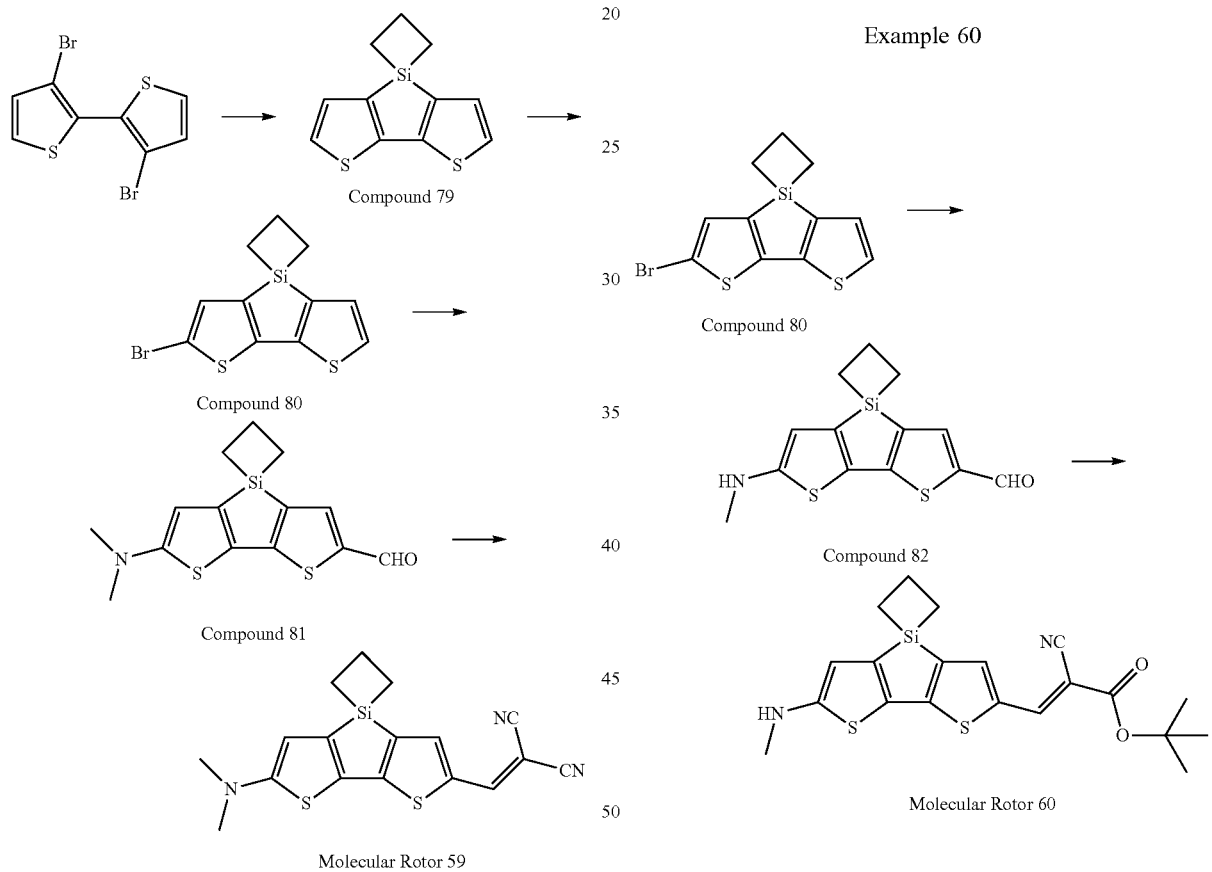

Synthesis of Compound 79

The synthesis was carried out by the method disclosed in the literature: Huang Hui et al. Chemistry of Materials, 2011, 23(8), 2185-2200. $^1$H-NMR (400 MHz, CDCl$_3$): δ=7.24 (d, 2H, J=5.0 Hz), 7.19 (d, 2H, J=5.0 Hz), 2.39 (t, 4H, J=9.0 Hz), 1.6 (t, 4H, J=9.0 Hz).

Synthesis of Compound 80

The synthesis was carried out according to the synthesis of Compound 75 in a yield of 51%. $^1$H-NMR (400 MHz, CDCl$_3$): δ=7.70 (s, 1H), 7.40 (d, 1H, J=4.8 Hz), 7.16 (d, 1H, J=4.8 Hz), 2.39 (t, 4H, J=9.0 Hz), 1.6 (t, 4H, J=9.0 Hz).

Synthesis of Compound 81

The synthesis was carried out with reference to the synthesis method of Compound 2, with a yield of 45%. $^1$H-NMR (400 MHz, CDCl$_3$): δ=9.88 (s, 1H), 7.83 (s, 1H), 7.10 (s, 1H), 3.1 (s, 6H), 2.39 (t, 4H, J=9.0 Hz), 1.6 (t, 4H, J=9.0 Hz).

Synthesis of Molecular Rotor 59

Molecular Rotor 59 was synthesized according to the synthesis of Molecular Rotor 4, with a yield of 91%. $^1$H-NMR (400 MHz, CDCl$_3$): δ=9.88 (s, 1H), 7.83 (s, 1H), 7.10 (s, 1H), 3.1 (s, 6H), 2.39 (t, 4H, J=9.0 Hz), 1.6 (t, 4H, J=9.0 Hz).

Example 60

Synthesis of Compound 82

The synthesis was carried out with reference to the synthesis of Compound 6, in a yield of 71%. $^1$H-NMR (400 MHz, CDCl$_3$): δ=9.87 (s, 1H), 7.85 (s, 1H), 7.11 (s, 1H), 3.15 (s, 3H), 2.39 (t, 4H, J=9.0 Hz), 1.6 (t, 4H, J=9.0 Hz).

Synthesis of Molecular Rotor 60

The synthesis was carried out by referring to the synthesis method of Molecular Rotor 1, and the yield was 95%. $^1$H-NMR (400 MHz, CDCl$_3$): δ=7.85 (s, 1H), 7.11 (s, 1H), 7.03 (s, 1H), 3.15 (s, 3H), 2.39 (t, 4H, J=9.0 Hz), 1.6 (t, 4H, J=9.0 Hz), 1.49 (s, 9H).

Example 61

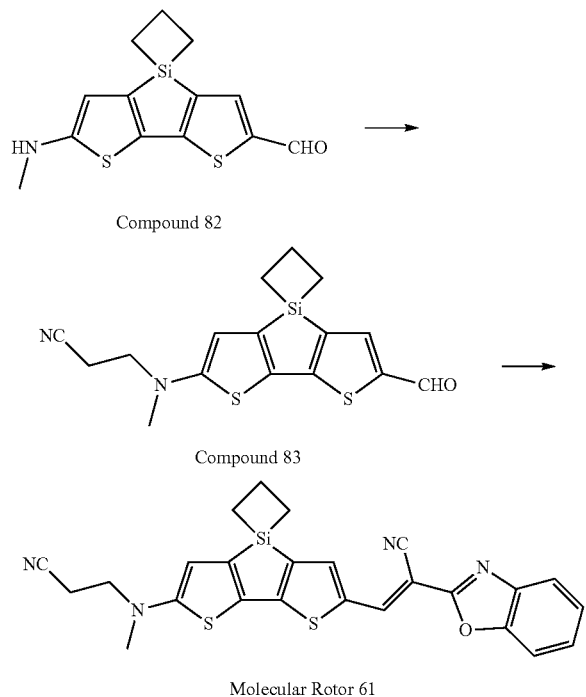

Synthesis of Compound 83

Compound 83 was synthesized according to the synthesis method of Compound 10 in a yield of 90%. $^{1}$H-NMR (400 MHz, CDCl$_3$): δ=9.87 (s, 1H), 7.85 (s, 1H), 7.11 (s, 1H), 3.72 (t, J=6.9 Hz, 2H), 3.03 (s, 3H), 2.57 (t, J=6.9 Hz, 2H), 2.39 (t, 4H, J=9.0 Hz), 1.6 (t, 4H, J=9.0 Hz).

Synthesis of Molecular Rotor 61

Molecular Rotor 61 was synthesized according to the synthesis of Molecular Rotor 2, with a yield of 89%. $^{1}$H-NMR (400 MHz, CDCl$_3$): δ=7.85 (s, 1H), 7.74 (d, 1H, J=4.0 Hz), 7.55 (d, 1H, J=4.0 Hz), 7.36-7.42 (m, 2H), 7.11 (s, 1H), 7.01 (s, 1H), 3.72 (t, J=6.9 Hz, 2H), 3.03 (s, 3H), 2.57 (t, J=6.9 Hz, 2H), 2.39 (t, 4H, J=9.0 Hz), 1.6 (t, 4H, J=9.0 Hz).

Example 62

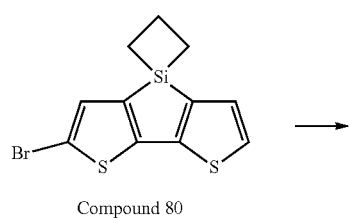

Compound 80

Synthesis of Compound 84

Compound 84 was synthesized according to the synthesis method of Compound 4 in a yield of 61%. $^{1}$H-NMR (400 MHz, CDCl$_3$): δ=9.88 (s, 1H), 7.85 (s, 1H), 7.11 (s, 1H), 3.59 (t, 2H, J=5.60 Hz), 3.48 (t, 2H, J=5.60 Hz), 3.14 (s, 3H), 2.39 (t, 4H, J=9.0 Hz), 1.6 (t, 4H, J=9.0 Hz).

Synthesis of Molecular Rotor 62

Molecular Rotor 62 was synthesized according to the synthesis of Molecular Rotor 3, with a yield of 95%. $^{1}$H-NMR (400 MHz, CDCl$_3$): δ=8.00 (d, 1H, J=8.0 Hz), 7.90 (d, 1H, J=8.0 Hz), 7.85 (s, 1H), 7.53 (t, 1H, J=8.0 Hz), 7.45 (t, 1H, J=8.0 Hz), 7.11 (s, 1H), 6.99 (s, 1H), 3.59 (t, 2H, J=5.60 Hz), 3.48 (t, 2H, J=5.60 Hz), 3.14 (s, 3H), 2.39 (t, 4H, J=9.0 Hz), 1.6 (t, 4H, J=9.0 Hz).

Example 63

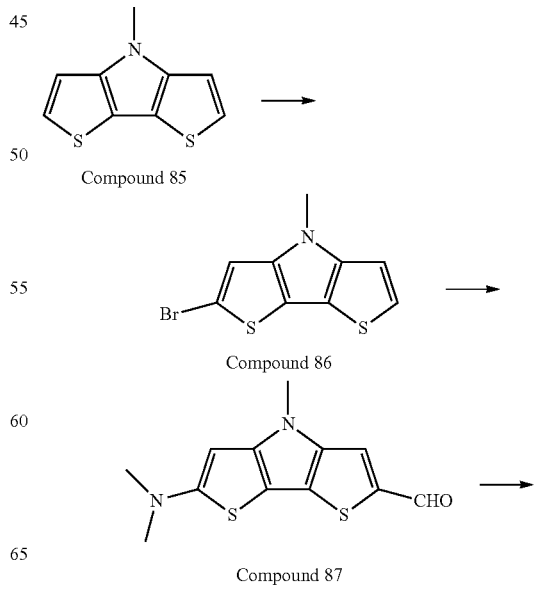

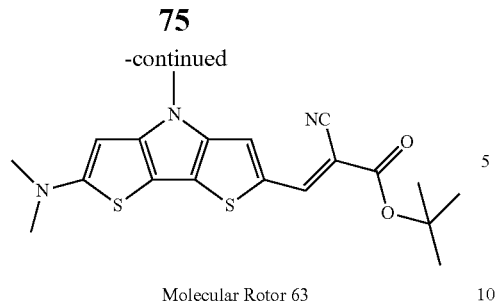

Molecular Rotor 63

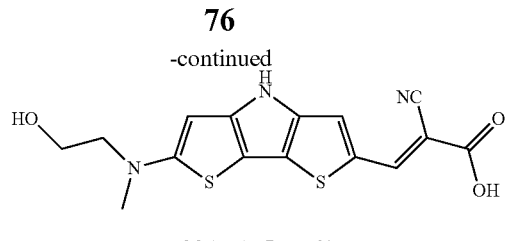

Molecular Rotor 64

Synthesis of Compound 85

Compound 85 was synthesized by the method disclosed in the literature (H. G. Jeong et al. Macromol. Chem. Phys. 2011, 212, 2308-2318): $^1$H-NMR (400 MHz, CDCl$_3$): δ=7.75 (d, J=5.2 Hz, 2H), 7.02 (d, J=5.2 Hz, 2H), 3.90 (s, 3H).

Synthesis of Compound 86

Compound 86 was synthesized according to the synthesis method of Compound 19: $^1$H-NMR (400 MHz, CDCl$_3$): δ=7.83 (s, 1H), 7.75 (d, J=5.2 Hz, 1H), 7.02 (d, J=5.2 Hz, 1H), 3.90 (s, 3H).

Synthesis of Compound 87

Compound 87 was synthesized according to the synthesis method of Compound 20. $^1$H-NMR (400 MHz, CDCl$_3$): δ=9.98 (s, 1H), 7.63 (s, 1H), 7.52 (s, J=5.2 Hz, 1H), 3.90 (s, 3H), 3.03 (s, 6H).

Synthesis of Molecular Rotor 63

Please refer to the synthesis of Molecular Rotor 2: $^1$H-NMR (400 MHz, CDCl$_3$): δ=7.63 (s, 1H), 7.52 (s, 1H), 7.03 (s, 1H), 3.90 (s, 3H), 3.03 (s, 6H), 1.51 (s, 9H).

Example 64

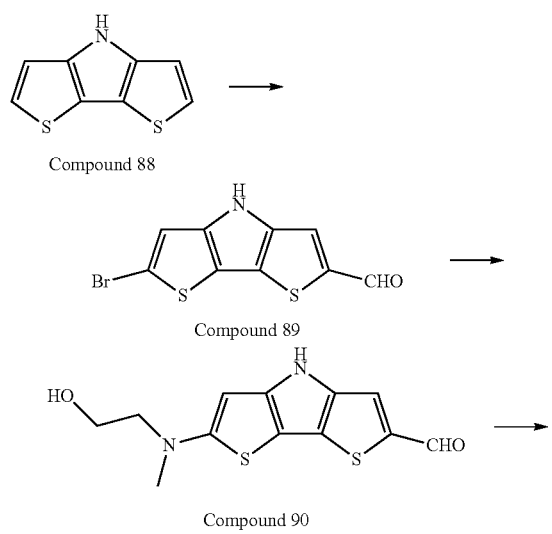

Synthesis of Compound 85

Compound 85 was synthesized by the method disclosed in the literature (H. G. Jeong et al. Macromol. Chem. Phys. 2011, 212, 2308-2318). $^1$H-NMR (400 MHz, CDCl$_3$): δ=7.78 (d, J=5.6 Hz, 2H), 7.09 (d, J=5.6 Hz, 2H).

Synthesis of Compound 89

Compound 89 was synthesized according to the synthesis of Compound 19: $^1$H-NMR (400 MHz, CDCl$_3$): δ=7.89 (s, 1H), 7.79 (d, J=5.6 Hz, 1H), 7.12 (d, J=5.6 Hz, 1H).

Synthesis of Compound 90

Compound 90 was synthesized with reference to the synthesis method of Compound 20: $^1$H-NMR (400 MHz, CDCl$_3$): δ=9.95 (s, 1H), 7.69 (s, 1H), 7.59 (s, J=5.2 Hz, 1H), 3.59 (t, 2H, J=5.60 Hz), 3.48 (t, 2H, J=5.60 Hz), 3.15 (s, 3H).

Synthesis of Molecular Rotor 64

Please refer to the synthesis of Molecular Rotor 5: $^1$H-NMR (400 MHz, CDCl$_3$): δ=7.69 (s, 1H), 7.58 (s, 1H), 7.01 (s, 1H), 3.59 (t, 2H, J=5.60 Hz), 3.48 (t, 2H, J=5.60 Hz), 3.15 (s, 3H), 1.51 (s, 9H).

Example 65

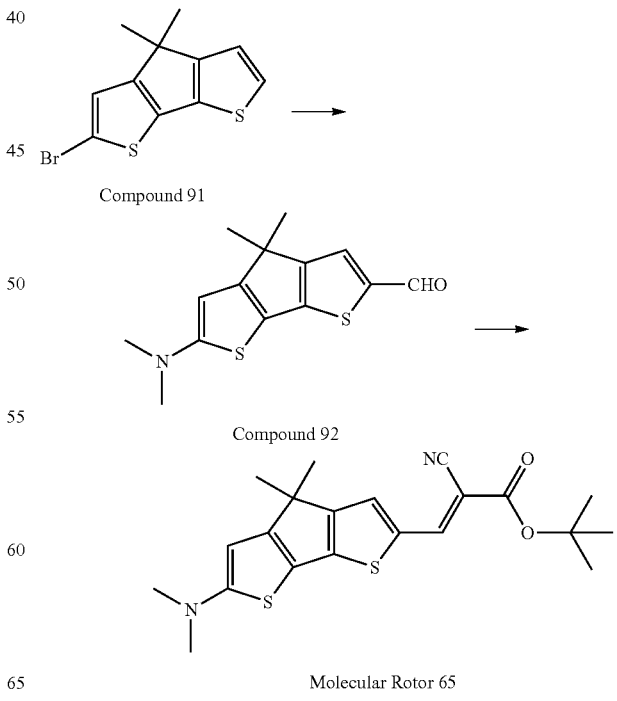

Compound 91

The synthesis was carried out by the method disclosed in the literature (Ping Yan. et al. J. Org. Chem. 2008, 73, 6587-6594). $^1$H-NMR (400 MHz, CDCl$_3$): δ=7.18 (s, 1H), 6.96 (d, 2H, J=5.6 Hz), 1.50 (s, 6H).

Compound 92

Compound 92 was synthesized according to the synthesis method of Compound 22 in a yield of 66%. $^1$H-NMR (400 MHz, CDCl$_3$): δ=9.89 (s, 1H), 7.18 (s, 1H), 6.96 (d, 2H, J=5.6 Hz), 3.10 (s, 6H), 1.50 (s, 6H).

Synthesis of Molecular Rotor 65

Molecular Rotor 65 was synthesized according to the synthesis of Molecular Rotor 1, with a yield of 98%. $^1$H-NMR (400 MHz, CDCl$_3$): δ=7.89 (s, 1H), 7.18 (s, 1H), 6.96 (d, 2H, J=5.6 Hz), 3.10 (s, 6H), 1.50 (m, 15H).

Example 66

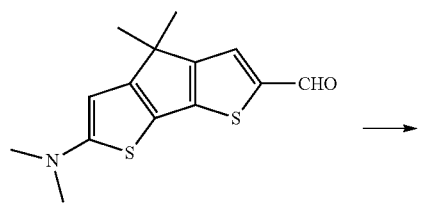

Compound 92

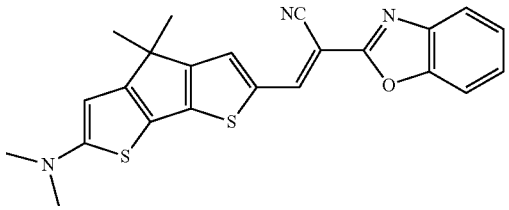

Molecular Rotor 66

Synthesis of Molecular Rotor 66

Molecular Rotor 66 was synthesized according to the synthesis of Molecular Rotor 2, with a yield of 66%. $^1$H-NMR (400 MHz, CDCl$_3$): δ=7.89 (s, 1H), 7.74 (d, 1H, J=4.0 Hz), 7.55 (d, 1H, J=4.0 Hz), 7.36-7.42 (m, 2H), 7.18 (s, 1H), 6.96 (d, 2H, J=5.6 Hz), 3.10 (s, 6H), 1.50 (s, 6H).

Example 67

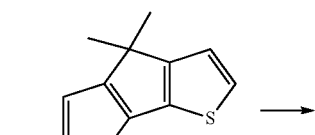

Compound 91

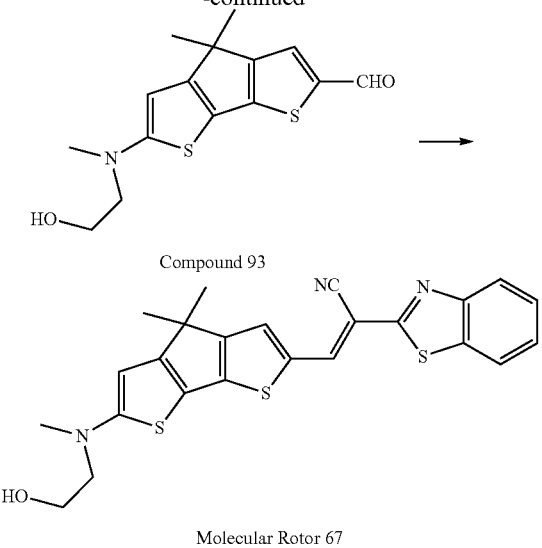

Molecular Rotor 67

Compound 93

Compound 93 was synthesized according to the synthesis method of Compound 2 in a yield of 36%. $^1$H-NMR (400 MHz, CDCl$_3$): δ=9.89 (s, 1H), 7.18 (s, 1H), 6.96 (d, 2H, J=5.6 Hz), 3.85 (t, 2H, J=5.6 Hz), 3.60 (t, 2H, J=5.6 Hz), 3.10 (s, 3H), 1.50 (s, 6H).

Synthesis of Molecular Rotor 67

Molecular Rotor 67 was synthesized according to the synthesis of Compound 1, with a yield of 98%. $^1$H-NMR (400 MHz, CDCl$_3$): δ=8.04 (d, 1H, J=8.0 Hz), 7.93 (d, 1H, J=8.0 Hz), 7.89 (s, 1H), 7.53 (t, 1H, J=8.0 Hz), 7.45 (t, 1H, J=8.0 Hz), 7.18 (s, 1H), 6.96 (d, 2H, J=5.6 Hz), 4.24 (s, 2H), 3.85 (t, 2H, J=5.6 Hz), 3.60 (t, 2H, J=5.6 Hz), 3.10 (s, 3H), 1.50 (s, 6H).

Example 68

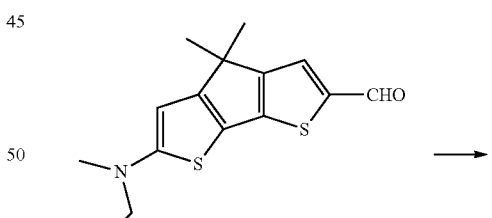

Compound 93

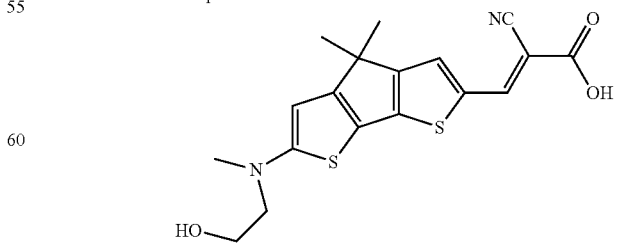

Molecular Rotor 68

Synthesis of Molecular Rotor 68

Molecular Rotor 68 was synthesized according to the synthesis of Compound 2, with a yield of 36%. $^1$H-NMR (400 MHz, CDCl$_3$): δ=7.89 (s, 1H), 7.18 (s, 1H), 6.96 (d, 2H, J=5.6 Hz), 3.10 (s, 6H), 1.50 (m, 6H).

Example 69

Synthesis of probe 1

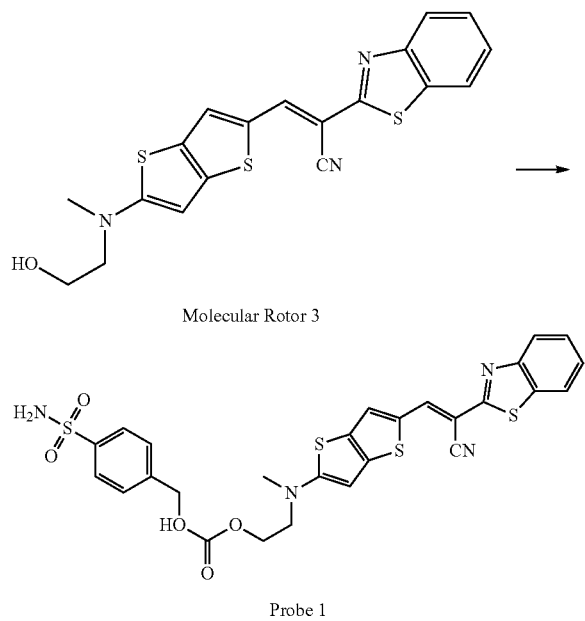

Probe 1

Molecular Rotor 3 (0.199 g, 0.5 mmol) and 4-dimethylaminopyridine (0.073 g, 0.6 mmol) were dissolved in 20 mL of anhydrous dichloromethane, to which a phenyl p-nitrochlorofou late (0.121 g, 0.6 mmol) solution in 10 mL of anhydrous dichloromethane was slowly added dropwise under Ar atmosphere, and then the mixture was stirred at room temperature for 1 h. After completion of the reaction, the resultant was dried by rotary evaporation to remove the solvent, and the residue was dissolved in 10 mL of anhydrous N,N-dimethylformamide, followed by adding a compound 4-aminomethylbenzenesulfonamide (0.11 g, 0.60 mmol) and anhydrous triethylamine (0.08 mL, 0.6 mmol) in turn. The mixture was stirred at room temperature for 30 min under argon atmosphere. After completion of the reaction, the resultant was dried by rotary evaporation to remove the solvent, and the residue undergone column separation to give a pure compound (0.225 g, 65%). $^1$H-NMR (400 MHz, DMSO-d$_6$): δ=8.45 (s, 1H), 8.17 (t, 1H, J=6.60 Hz), 8.09 (d, 1H, J=8.00 Hz), 8.07 (s, 1H), 7.94 (d, 1H, J=8.00 Hz), 7.80 (d, 1H, J=8.10 Hz), 7.51 (m, 1H), 7.41 (m, 3H), 7.30 (s, 2H), 6.45 (s, 1H), 4.92 (t, 1H, J=5.60 Hz), 4.32 (d, 1H, J=6.00 Hz), 3.67 (t, 2H, J=5.60 Hz), 3.49 (t, 2H, J=5.60 Hz), 3.13 (s, 3H).

Example 70

The fluorescent dyes (molecular rotors) prepared in Examples 1-68 were separately dissolved in dimethyl sulfoxide to prepare respectively a mother liquor having a concentration of $1×10^{-2}$ M, and each of the mother liquors was added individually to glycerin and methanol, and mixed uniformly, thereby solutions of a final concentration of $1×10^{-5}$ M were prepared individually. According to the different fluorescent dyes, the fluorescence emission spectra of the fluorescent dyes were detected with the maximum excitation wavelengths of respective fluorescent dyes successively under the same conditions. The results were shown in Table 1. It indicates that the fluorescent dyes of the present invention have long-wavelength fluorescence emission and is sensitive to viscosity changes.

TABLE 1

Emission Wavelength of Each Molecular Rotor and Its Ratio of Fluorescence Intensities in Glycerol to Methanol Solution

| Name of Compound | Maximum Emission Wavelength (nm) | Fluorescence Intensity Ratios in Glycerol/Methanol |
|---|---|---|
| Molecular Rotor 1 | 555 | 790 |
| Molecular Rotor 2 | 590 | 1183 |
| Molecular Rotor 3 | 610 | 1455 |
| Molecular Rotor 4 | 557 | 892 |
| Molecular Rotor 5 | 555 | 1980 |
| Molecular Rotor 6 | 585 | 1453 |
| Molecular Rotor 7 | 555 | 1877 |
| Molecular Rotor 8 | 570 | 456 |
| Molecular Rotor 9 | 630 | 320 |
| Molecular Rotor 10 | 520 | 851 |
| Molecular Rotor 11 | 620 | 568 |
| Molecular Rotor 12 | 655 | 655 |
| Molecular Rotor 13 | 690 | 352 |
| Molecular Rotor 14 | 620 | 681 |
| Molecular Rotor 15 | 620 | 799 |
| Molecular Rotor 16 | 620 | 951 |
| Molecular Rotor 17 | 618 | 888 |
| Molecular Rotor 18 | 630 | 678 |
| Molecular Rotor 19 | 650 | 791 |
| Molecular Rotor 20 | 690 | 536 |
| Molecular Rotor 21 | 620 | 544 |
| Molecular Rotor 22 | 570 | 989 |
| Molecular Rotor 23 | 608 | 568 |
| Molecular Rotor 24 | 608 | 912 |
| Molecular Rotor 25 | 570 | 615 |
| Molecular Rotor 26 | 610 | 712 |
| Molecular Rotor 27 | 600 | 601 |
| Molecular Rotor 28 | 650 | 569 |
| Molecular Rotor 29 | 570 | 515 |
| Molecular Rotor 30 | 520 | 513 |
| Molecular Rotor 31 | 535 | 572 |
| Molecular Rotor 32 | 570 | 612 |
| Molecular Rotor 33 | 565 | 531 |
| Molecular Rotor 34 | 626 | 1012 |
| Molecular Rotor 35 | 626 | 476 |
| Molecular Rotor 36 | 628 | 901 |
| Molecular Rotor 37 | 627 | 879 |
| Molecular Rotor 38 | 650 | 623 |
| Molecular rotor 39 | 667 | 541 |
| Molecular Rotor 40 | 659 | 652 |
| Molecular Rotor 41 | 558 | 875 |
| Molecular Rotor 42 | 558 | 924 |
| Molecular Rotor 43 | 582 | 816 |
| Molecular Rotor 44 | 603 | 631 |
| Molecular Rotor 45 | 585 | 812 |
| Molecular Rotor 46 | 563 | 712 |
| Molecular Rotor 47 | 561 | 912 |
| Molecular Rotor 48 | 562 | 608 |
| Molecular Rotor 49 | 559 | 612 |
| Molecular Rotor 50 | 587 | 777 |
| Molecular Rotor 51 | 599 | 535 |
| Molecular Rotor 52 | 578 | 680 |
| Molecular Rotor 53 | 599 | 915 |
| Molecular Rotor 54 | 563 | 722 |
| Molecular Rotor 55 | 562 | 466 |
| Molecular Rotor 56 | 655 | 591 |
| Molecular Rotor 57 | 659 | 884 |

TABLE 1-continued

Emission Wavelength of Each Molecular Rotor and Its
Ratio of Fluorescence Intensities in Glycerol to Methanol Solution

| Name of Compound | Maximum Emission Wavelength (nm) | Fluorescence Intensity Ratios in Glycerol/Methanol |
|---|---|---|
| Molecular Rotor 58 | 656 | 683 |
| Molecular Rotor 59 | 655 | 750 |
| Molecular Rotor 60 | 637 | 812 |
| Molecular Rotor 61 | 691 | 816 |
| Molecular Rotor 62 | 715 | 759 |
| Molecular Rotor 63 | 675 | 516 |
| Molecular Rotor 64 | 655 | 682 |
| Molecular Rotor 65 | 645 | 591 |
| Molecular Rotor 66 | 670 | 623 |
| Molecular Rotor 67 | 690 | 789 |
| Molecular Rotor 68 | 648 | 953 |

Example 71

Molecular Rotors 1, 2, 3, 22, 57, and 63 were added to ethylene glycol-glycerol mixed solutions having viscosities of 16.4 cp, 29.8 cp, 64.5 cp, 143.5 cp, 377.0 cp, and 946.0 cp to prepare a solution with a final concentration of $1 \times 10^{-5}$ M. The solution was excited at 480 nm. The fluorescence emission spectra at different viscosities were shown in FIGS. 1, 4, 7, 10, 13, and 16. Emission wavelengths of the molecular rotors were 555 nm, 590 nm, 610 nm, 570 nm, 559 nm, and 675 nm, respectively. The fluorescence intensities of the molecular rotors with the same concentration increase at different viscosities, which indicates that the fluorescence intensities of the molecular rotors increase with the increase in the ambient viscosity, and that the relationship between the logarithm of fluorescence intensity and the logarithm of solvent viscosity is consistent with the Huffman equation, that is, having a very good linear relationship and having a high slope (as shown in FIGS. 2, 5, 8, 11, 14, and 17). This demonstrates that the molecular rotors are sensitive to viscosity and can be used for viscosity testing of unknown samples.

Example 72

Molecular Rotors 1, 2, 3, 22, 57, 63 were added to dichloromethane and methanol respectively to prepare a solution with a final concentration of $1 \times 10^{-5}$ M. Then, the solution was excited individually by excitation wavelengths of 480 nm, 480 nm and 500 nm at 25° C. to detect their fluorescence emission intensities in two different polar solvents. As shown in FIG. 3, FIG. 6, FIG. 9, FIG. 12, FIG. 15 and FIG. 18, the fluorescence emission intensities of the molecular rotors in the solution are weak, and the fluorescence intensities do not change much in the strong polar and strong non-polar solvents, which indicates that the molecular rotors of the present invention are weak in background fluorescence of the fluorescence intensities, and insensitive to the polarity change.

Example 73

Figure 19:
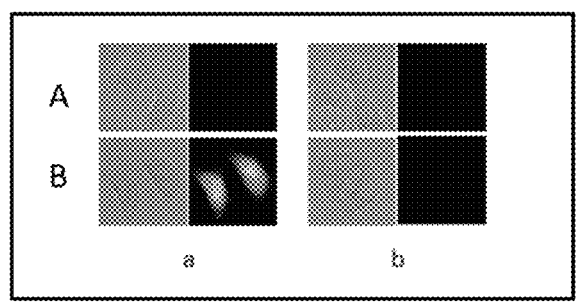
FIG. 19 shows fluorescence imaging pictures of probe 1 for intracellular carbonic anhydrase detection, wherein A is an unexpressed carbonic anhydrase cell and B is an expressed carbonic anhydrase cell.

The effect of probe 1 on the fluorescence monitoring of carbonic anhydrase was investigated by using HeLa cells as an example. HeLa cells with high expression of carbonic anhydrase and Hela-WT cells (Hela archecytes) without expression of carbonic anhydrase were planted in a 14 mm glass bottom 96-well cell culture plate and stabilized for 10 hours. Probe 1 was added to the medium with the concentration thereof set to 5 µM. The cells were incubated for 2 hours in a carbon dioxide incubator at 37° C., and the fluorescence changes of the labeled cells were imaged and detected with a Leica TPS-8 confocal microscope. The results in FIG. 19Aa show that after the addition of probe 1 to the medium, the corresponding fluorescent signal is not detected in Hela-WT cells, indicating that the probe fluorescence is not affected by the intracellular environment; however, in FIG. 19Ba, a strong fluorescent signal can be detected in the Hela cells expressing carbonic anhydrase protein, and the fluorescence signal is enhanced by nearly 300-fold in comparison with the Hela-WT cells. It is indicated that the probe of the present invention can specifically label the intracellular carbonic anhydrase protein to achieve fluorescence-specific illumination, and at the same time, the probe fluorescence is not affected by the intracellular environment. In order to prove that the increased fluorescence results from the interaction of probe 1 and carbonic anhydrase, ethoxzolamide, which is more interactive with carbonic anhydrase in comparison to probe 1, was further added, and its concentration was increased to 10 µM. The cells were placed in a carbon dioxide incubator at 37° C. again and incubated for 1 hour. The fluorescence changes of the labeled cells were imaged and detected with a Leica TPS-8 confocal microscope. The fluorescence intensity of the cells in FIG. 19Bb is only 8% of that of the cells in FIG. 19Ba, which shows that the fluorescence intensity of the cells decreases drastically, and indicates that the reason for the fluorescence illumination is that the molecular conformation is restricted after the interaction between probe 1 and carbonic anhydrase.

This example demonstrates that the fluorescent dye of the present invention is suitable for specific binding to a corresponding antibody, aptamer or amyloid, or developing a series of fluorogenic probes for the fluorescence labeling, quantification or monitoring of proteins, enzymes or nucleic acids by means of bonding a ligand or inhibitor to a protein tag or enzyme and introducing molecular rotors into the lumen of the enzyme and the like.

The invention claimed is:
1. A fluorescent dye, having a structure represented by formula (I)

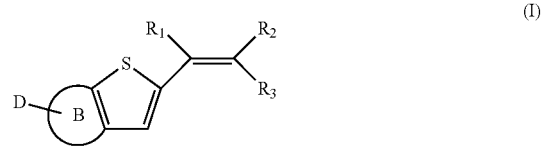

wherein,
D- is —OH or $N(X_1)(X_2)$—; $X_1$, and $X_2$ are each independently selected from the group consisting of hydrogen, an alkyl group and a first modified alkyl group; the first modified alkyl group is a group obtained by replacing any carbon atom or any carbon atom with hydrogens thereon of the alkyl group with at least one group selected from the group consisting of a halogen atom, —O—, —OH, —CO—, —CN, —SO$_2$—, —(S=O)—, a primary amino group, a secondary amino group, and a tertiary amino group, the first modified alkyl group has 1 to 11 carbon atoms, $X_1$ and $X_2$ are optionally linked to each other to form a saturated or unsaturated alicyclic heterocyclic ring; the alicyclic heterocyclic ring is selected from the group consisting of azetidine, pyrrolidine, piperidine, and morpholine;

the ring B is selected from at least one consisting of an aromatic ring and an aromatic heterocyclic ring;

in the structure of the following formula (I-2) formed by condensing the ring B with a thiophene ring, each hydrogen atom contained therein is optionally replaced independently with a substituent selected from the group consisting of an alkyl group and a methoxy group

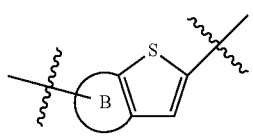

(I-2)

wherein $R_1$ is hydrogen;

$R_2$ is selected from the group consisting of cyano, carboxyl, a keto group, an ester group, an amide group, an aryl group, a heteroaryl group, and a second modified alkyl group; the second modified alkyl group is a group obtained by replacing any carbon atom or any carbon atom with hydrogens thereon of the alkyl group with at least one group selected from the group consisting of —O—, —OH, —CO—, a primary amino group, a secondary amino group, a tertiary amino group, the second modified alkyl group has 1 to 4 carbon atoms; and $R_3$ is a cyano group; or the structural moiety of the following formula (I-3) in the formula (I):

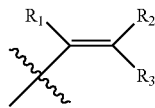

(I-3)

forms a cyclic structure of the following formulae (I-3-a) or (I-3-b):

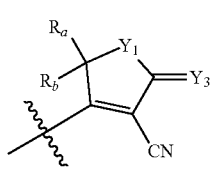

(I-3-a)

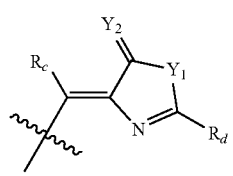

(I-3-b)

wherein, $R_a$ and $R_b$ are selected independently from the group consisting of hydrogen, and an alkyl group;

$R_c$ is hydrogen;

$R_d$ is selected independently from the group consisting of hydrogen, an alkyl group, and an aryl group;

$Y_1$ is selected from the groups consisting of —O—, —S—, —(S=O)—, and —(NR$_i$)—, wherein $R_i$ is selected from the group consisting of hydrogen and an alkyl group;

$Y_2$ is selected from the group consisting of =O and =S; and $Y_3$ is selected from the group consisting of =O and =S;

wherein, the alkyl group is a saturated aliphatic linear or branched alkyl group having 1 to 10 carbon atoms;

the aryl group is a five to ten-membered monocyclic or condensed bicyclic ring;

the heteroaryl or the aromatic heterocyclic ring is a five to ten-membered monocyclic or condensed bicyclic ring with at least one heteroatom selected from the group consisting of N, O and S on the ring; and the halogen atom is each independently selected from the group consisting of F, Cl, Br, and I.

2. The fluorescent dye according to claim 1, wherein $X_1$ and $X_2$ are independently a $C_{1-10}$ linear or branched alkyl group optionally substituted by one or more groups selected from the group consisting of hydroxyl and cyano; or a $C_{2-11}$ ether chain group having 1 to 10 oxygen atoms and optionally substituted by one or more groups selected from the group consisting of a sulfonic acid group or carboxyl.

3. The fluorescent dye according to claim 1, wherein the structure of the formula (I-2) is selected from the structures of the following formulae (I-2-1) to (I-2-13), (I-2-16), or (I-2-17):

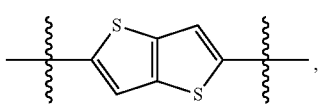

(I-2-1)

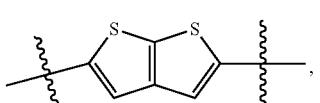

(I-2-2)

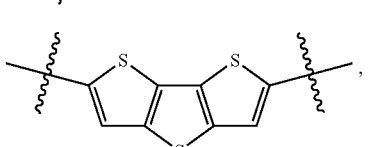

(I-2-3)

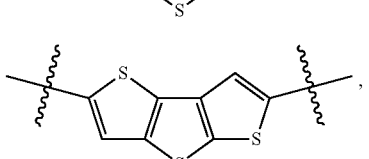

(I-2-4)

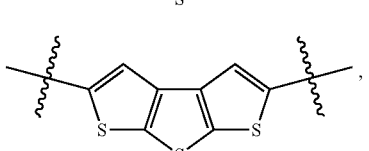

(I-2-5)

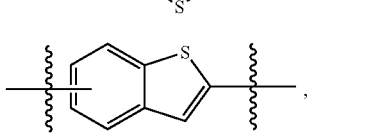

(I-2-6)

-continued (I-2-7)

(I-2-8)

(I-2-9)

(I-2-10)

(I-2-11)

(I-2-12)

(I-2-13)

(I-2-16) or (I-2-17)

4. The fluorescent dye according to claim 1, wherein the $R_2$ is a group selected from the following structures, or bicyclic or polycyclic condensed aromatic rings or condensed aromatic heterocyclic rings formed by the following structures themselves or condensed therebetween:

5. A fluorescent dye, wherein the fluorescent dye is selected from the group consisting of the compounds of the following formulae:

Molecular Rotor 1

Molecular Rotor 2

Molecular Rotor 3

Molecular Rotor 4

-continued
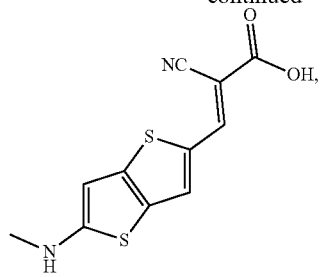
Molecular Rotor 5
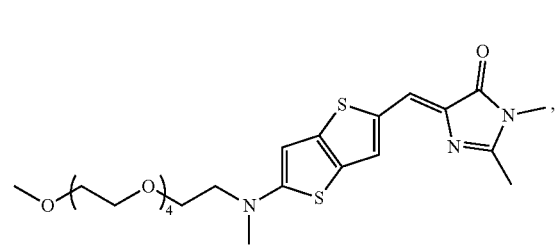
Molecular Rotor 6
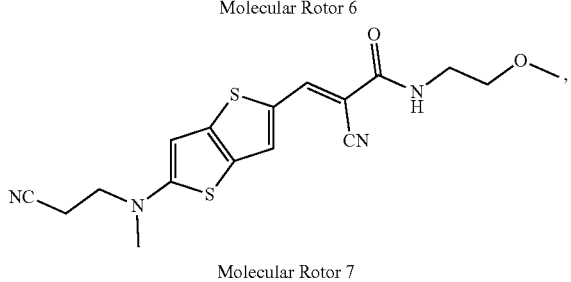
Molecular Rotor 7
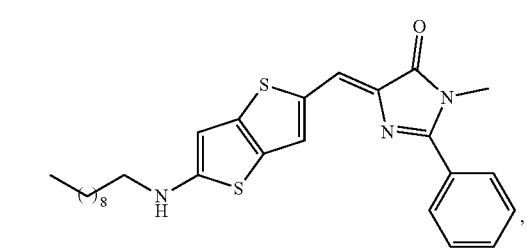
Molecular Rotor 8
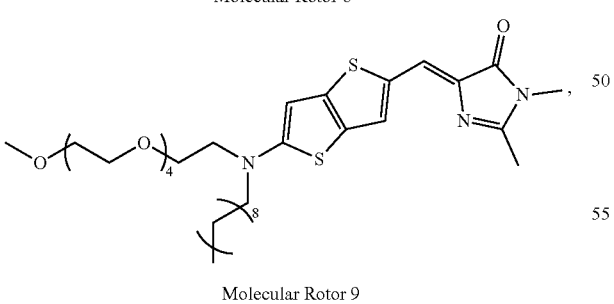
Molecular Rotor 9
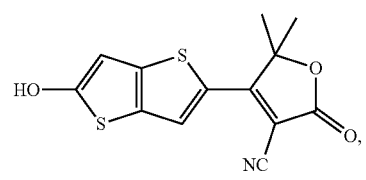
Molecular Rotor 10
-continued
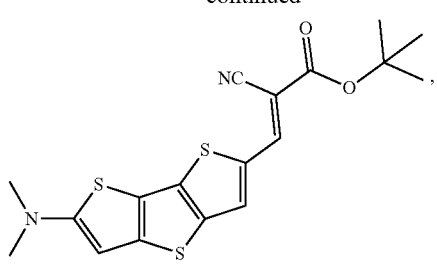
Molecular Rotor 11
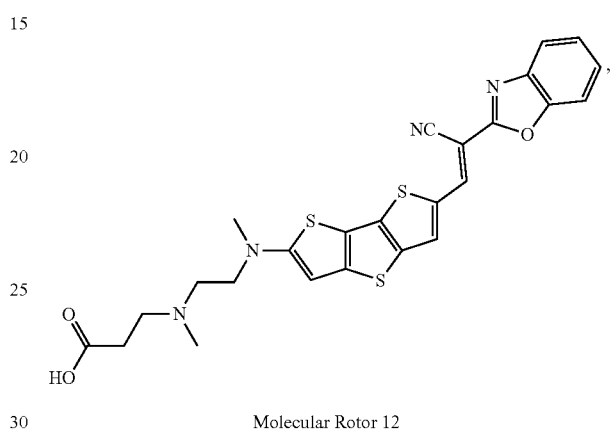
Molecular Rotor 12
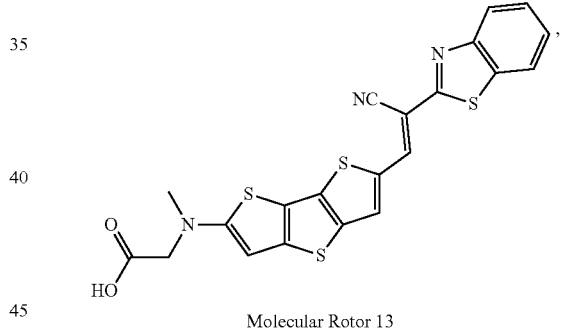
Molecular Rotor 13
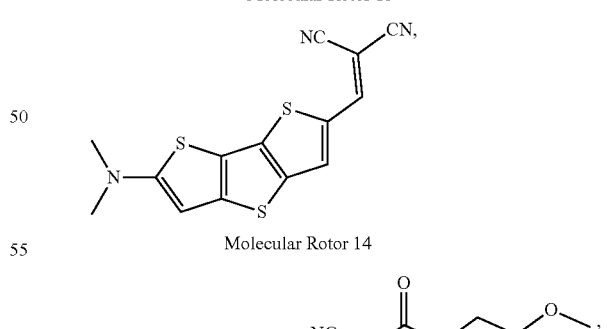
Molecular Rotor 14
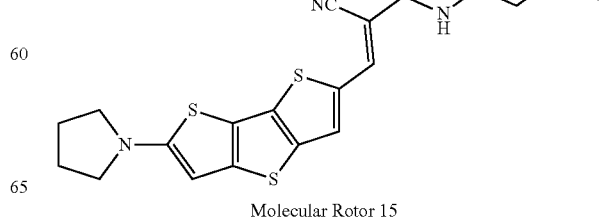
Molecular Rotor 15

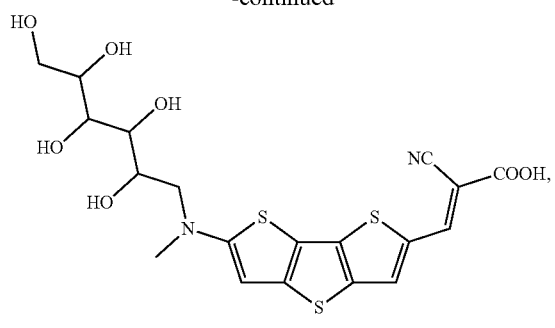
Molecular Rotor 16
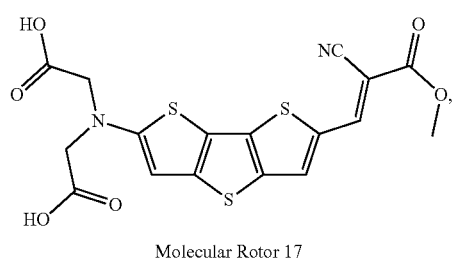
Molecular Rotor 17
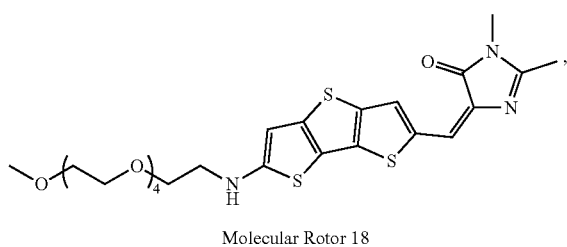
Molecular Rotor 18
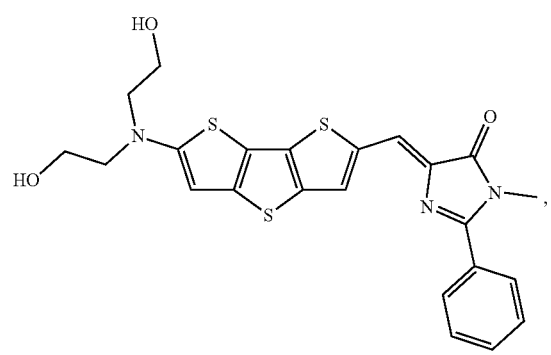
Molecular Rotor 19
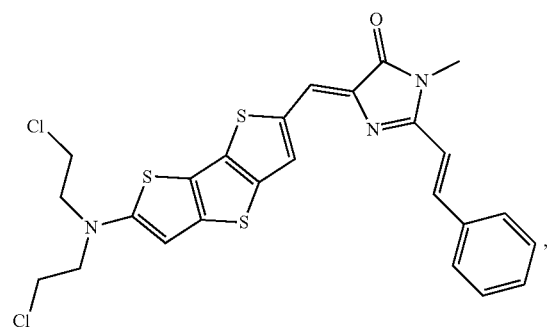
Molecular Rotor 20
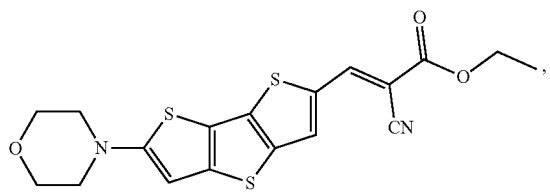
Molecular Rotor 21
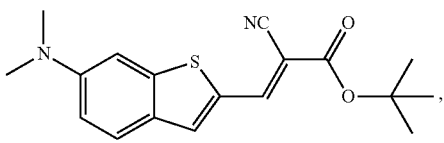
Molecular Rotor 22
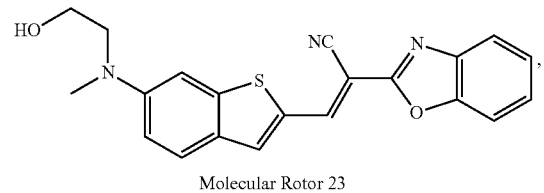
Molecular Rotor 23
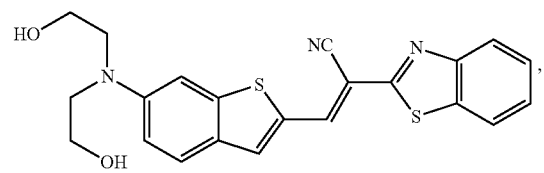
Molecular Rotor 24
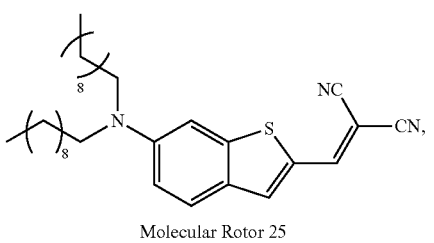
Molecular Rotor 25
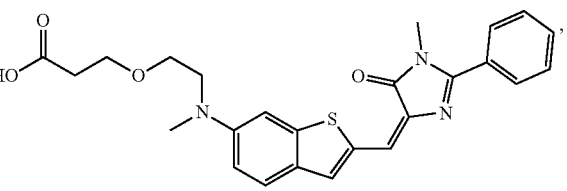
Molecular Rotor 26
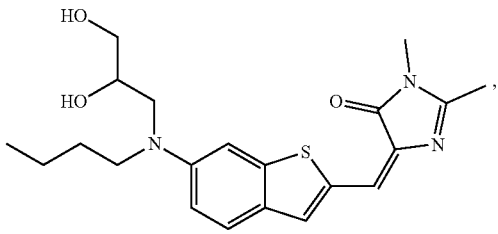
Molecular Rotor 27

Molecular Rotor 28

Molecular Rotor 29

Molecular Rotor 31

Molecular Rotor 32

Molecular Rotor 33

Molecular Rotor 34

Molecular Rotor 35

Molecular Rotor 36

Molecular Rotor 37

Molecular Rotor 38

Molecular Rotor 39

Molecular Rotor 40

Molecular Rotor 41

Molecular Rotor 42

Molecular Rotor 43

Molecular Rotor 44

Molecular Rotor 45

Molecular Rotor 46

Molecular Rotor 47

Molecular Rotor 48

Molecular Rotor 49

Molecular Rotor 50

Molecular Rotor 51

Molecular Rotor 52

Molecular Rotor 53

Molecular Rotor 54

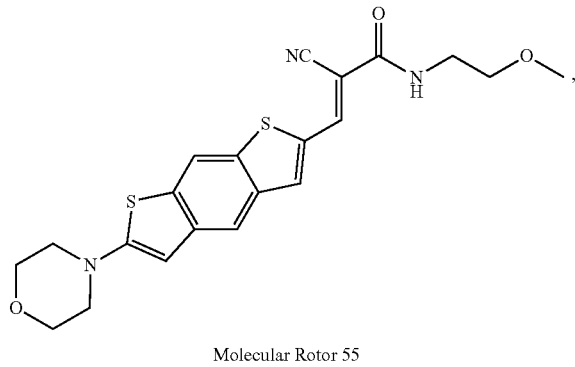

Molecular Rotor 55

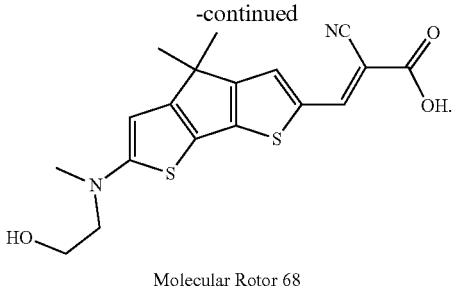

Molecular Rotor 68

6. A process for preparing the fluorescent dye according to claim 1, comprising the step of conducting an aldol condensation reaction of a compound of the formula (II) with a compound of the formula (III):

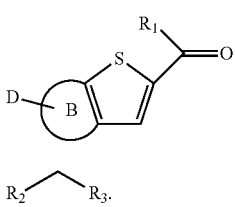

(II)

(III)

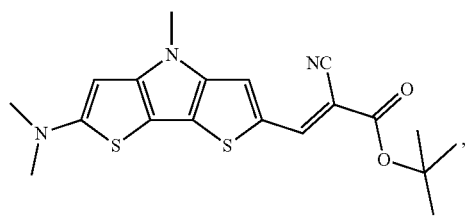

Molecular Rotor 63

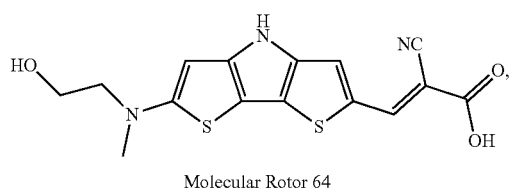

Molecular Rotor 64

7. A process comprising using the fluorescent dye according to claim 1 in viscosity testing, fluorescent labeling of a protein, fluorescent labeling of a nucleic acid, quantification or detection of a protein, or quantification or detection of a nucleic acid.

8. A fluorogenic probe, comprising the fluorescent dye according to claim 1.

9. A process comprising using the fluorogenic probe according to claim 8 in fluorescent labeling of a protein, fluorescent labeling of a nucleic acid, quantification or detection of a protein, or quantification or detection of a nucleic acid.

10. The fluorescent dye according to claim 3, wherein the $R_2$ is a group selected from the following structures, or bicyclic or polycyclic condensed aromatic rings or condensed aromatic heterocyclic rings formed by the following structures themselves or condensed therebetween:

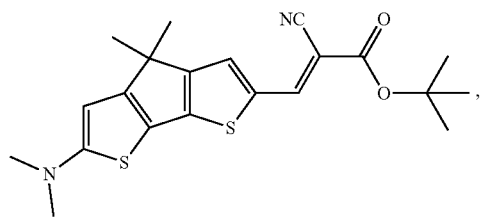

Molecular Rotor 65

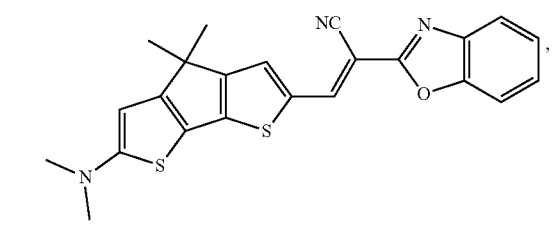

Molecular Rotor 66

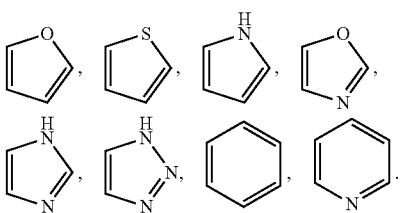

11. A process comprising using the fluorescent dye according to claim 4 in viscosity testing, fluorescent labeling of a protein, fluorescent labeling of a nucleic acid, quantification or detection of a protein, or quantification or detection of a nucleic acid.

12. A process comprising using the fluorescent dye according to claim 10 in viscosity testing, fluorescent labeling of a protein, fluorescent labeling of a nucleic acid, quantification or detection of a protein, or quantification or detection of a nucleic acid.

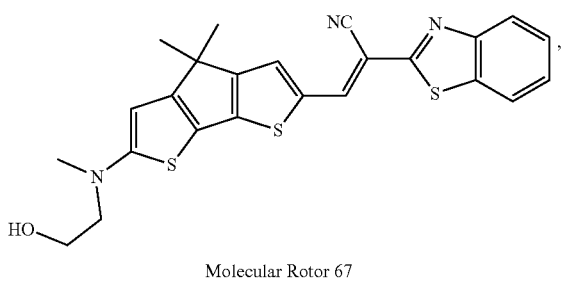

Molecular Rotor 67

13. A process comprising using the fluorescent dye according to claim 5 in viscosity testing, fluorescent labeling of a protein, fluorescent labeling of a nucleic acid, quantification or detection of a protein, or quantification or detection of a nucleic acid.

14. A fluorogenic probe, comprising the fluorescent dye according to claim 4.

15. A fluorogenic probe, comprising the fluorescent dye according to claim 10.

16. A fluorogenic probe, comprising the fluorescent dye according to claim 5.

17. A process comprising using the fluorogenic probe according to claim 14 in fluorescent labeling of a protein, fluorescent labeling of a nucleic acid, quantification or detection of a protein, or quantification or detection of a nucleic acid.

18. A process comprising using the fluorogenic probe according to claim 15 in fluorescent labeling of a protein, fluorescent labeling of a nucleic acid, quantification or detection of a protein, or quantification or detection of a nucleic acid.

19. A process comprising using the fluorogenic probe according to claim 16 in fluorescent labeling of a protein, fluorescent labeling of a nucleic acid, quantification or detection of a protein, or quantification or detection of a nucleic acid.

20. A fluorescent dye, having a structure represented by formula (I):

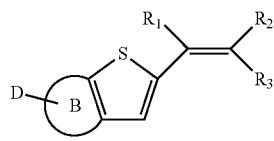

(I)

wherein,

D- is —OH or $N(X_1)(X_2)$—; $X_1$, and $X_2$ are each independently selected from the group consisting of hydrogen, an alkyl group and a first modified alkyl group; the first modified alkyl group is a group obtained by replacing any carbon atom or any carbon atom with hydrogens thereon of the alkyl group with at least one group selected from the group consisting of a halogen atom, —O—, —OH, —CO—, —CN, —SO$_2$—, —(S=O)—, a primary amino group, a secondary amino group, and a tertiary amino group, the first modified alkyl group has 1 to 11 carbon atoms, $X_1$ and $X_2$ are optionally linked to each other to form a saturated or unsaturated alicyclic heterocyclic ring; the alicyclic heterocyclic ring is selected from the group consisting of azetidine, pyrrolidine, piperidine, and morpholine;

the ring B is selected from at least one consisting of an aromatic ring and an aromatic heterocyclic ring;

in the structure of the following formula (I-2) formed by condensing the ring B with a thiophene ring, each hydrogen atom contained therein is optionally replaced independently with a substituent selected from the group consisting of an alkyl group and a methoxy group;

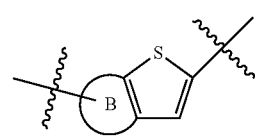

(I-2)

the structural moiety of the following formula (I-3) in the formula (I) is one of the following formulae (I-3-1) to (I-3-18):

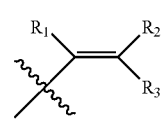

(I-3)

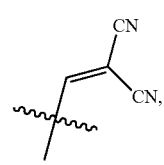

(I-3-1)

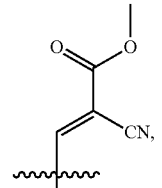

(I-3-2)

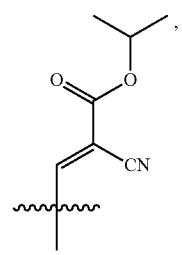

(I-3-3)

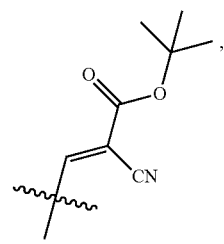

(I-3-4)

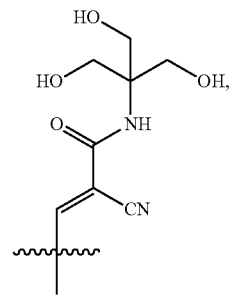

(I-3-5)

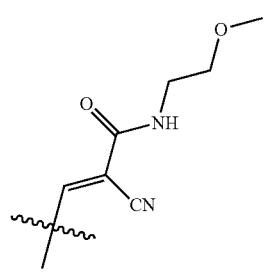
(I-3-6)
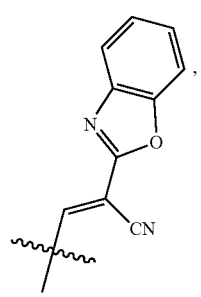
(I-3-7)
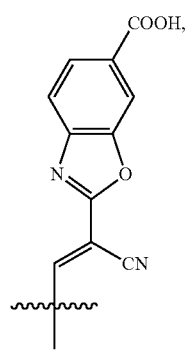
(I-3-8)
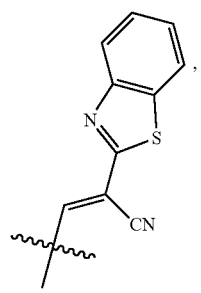
(I-3-9)
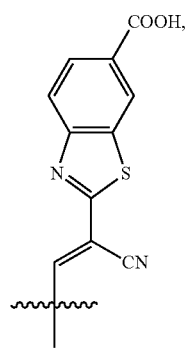
(I-3-10)
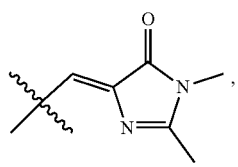
(I-3-11)
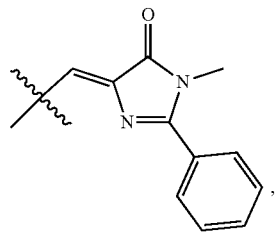
(I-3-12)
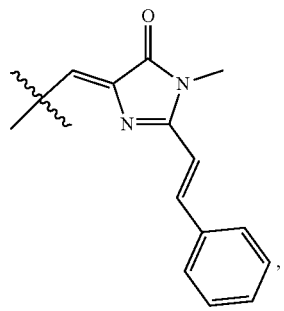
(I-3-13)
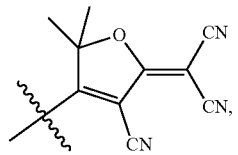
(I-3-14)
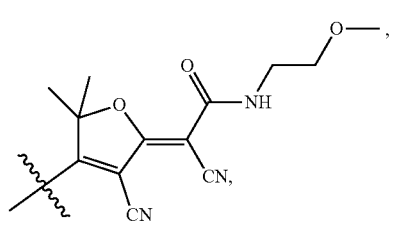
(I-3-15)

wherein, the alkyl group is a saturated aliphatic linear or branched alkyl group having 1 to 10 carbon atoms;

the aryl group is a five to ten-membered monocyclic or condensed bicyclic ring;

the heteroaryl or the aromatic heterocyclic ring is a five to ten-membered monocyclic or condensed bicyclic ring with at least one heteroatom selected from the group consisting of N, O and S on the ring; and the halogen atom is each independently selected from the group consisting of F, Cl, Br, and I.

21. The fluorescent dye according to claim 20, wherein $X_1$ and $X_2$ are independently a $C_{1-10}$ linear or branched alkyl group optionally substituted by one or more groups selected from the group consisting of hydroxyl and cyano; or a $C_{2-11}$ ether chain group having 1 to 10 oxygen atoms and optionally substituted by one or more groups selected from the group consisting of a sulfonic acid group and carboxyl.

22. The fluorescent dye according to claim 20, wherein the structure of the formula (I-2) is selected from the structures of the following formulae (I-2-1) to (I-2-13), (I-2-16), and (I-2-17):

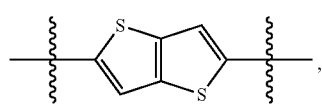 (I-2-1)

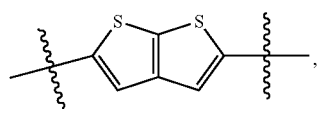 (I-2-2)

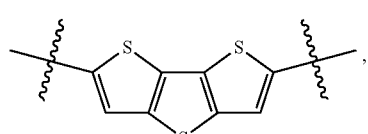 (I-2-3)

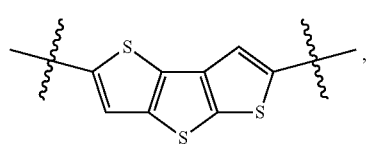 (I-2-4)

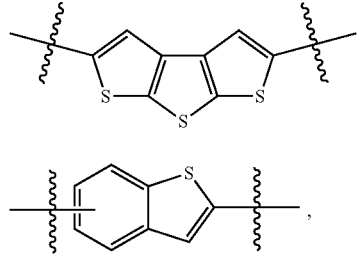 (I-2-5)

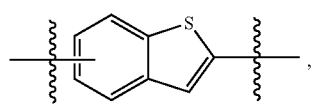 (I-2-6)

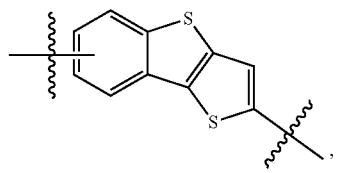 (I-2-7)

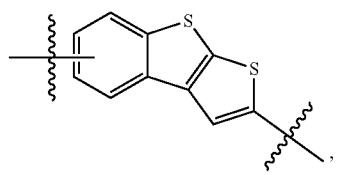 (I-2-8)

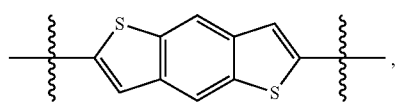 (I-2-9)

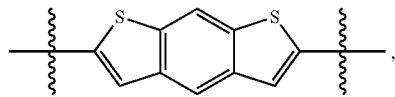 (I-2-10)

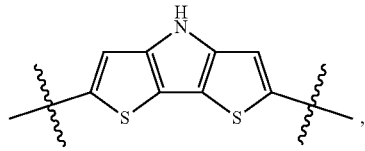 (I-2-11)

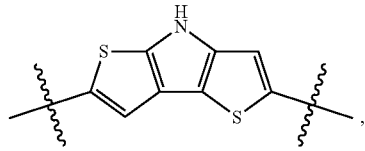 (I-2-12)

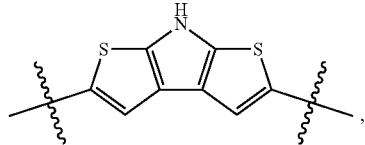 (I-2-13)

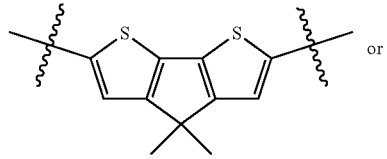 or (I-2-16)

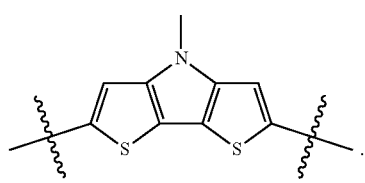 (I-2-17)

* * * * *